US011124813B2

(12) United States Patent
Haas et al.

(10) Patent No.: US 11,124,813 B2
(45) Date of Patent: Sep. 21, 2021

(54) N-ACETYL HOMOSERINE

(71) Applicant: Evonik Operations GmbH, Essen (DE)

(72) Inventors: Thomas Haas, Münster (DE); Steffen Schaffer, Herten (DE); Thomas Bülter, Duisburg (DE); Simon Beck, Münster (DE)

(73) Assignee: Evonik Operations GmbH, Essen (DE)

( * ) Notice: Subject to any disclaimer, the term of this patent is extended or adjusted under 35 U.S.C. 154(b) by 57 days.

(21) Appl. No.: 16/320,097

(22) PCT Filed: Jul. 26, 2017

(86) PCT No.: PCT/EP2017/068841
§ 371 (c)(1),
(2) Date: Jan. 24, 2019

(87) PCT Pub. No.: WO2018/019867
PCT Pub. Date: Feb. 1, 2018

(65) Prior Publication Data
US 2019/0264245 A1 Aug. 29, 2019

(30) Foreign Application Priority Data

Jul. 27, 2016 (EP) .................... 16181431

(51) Int. Cl.
*C12P 13/06* (2006.01)
*C07C 233/47* (2006.01)

(52) U.S. Cl.
CPC .......... *C12P 13/06* (2013.01); *C07C 233/47* (2013.01); *C12Y 101/01003* (2013.01); *C12Y 203/01031* (2013.01); *C12Y 203/01046* (2013.01); *C12Y 207/02004* (2013.01); *C12Y 401/0102* (2013.01)

(58) Field of Classification Search
None
See application file for complete search history.

(56) References Cited

U.S. PATENT DOCUMENTS

| | | | |
|---|---|---|---|
| 3,992,268 A | 11/1976 | Antos | |
| 4,540,772 A | 9/1985 | Pipper et al. | |
| 5,604,127 A | 2/1997 | Nisbet et al. | |
| 5,723,603 A | 3/1998 | Gilbert et al. | |
| 5,807,722 A | 9/1998 | Gaddy | |
| 6,492,541 B2 | 12/2002 | Drauz et al. | |
| 7,196,218 B2 | 3/2007 | Gaddy et al. | |
| 7,241,908 B2 | 7/2007 | Haas et al. | |
| 7,364,718 B2 | 4/2008 | Haas et al. | |
| 7,368,600 B2 | 5/2008 | Hateley et al. | |
| 8,241,881 B2 | 8/2012 | Bradin | |
| 8,535,921 B2 | 9/2013 | Kohn et al. | |
| 8,703,451 B2 | 4/2014 | Haas et al. | |
| 8,809,576 B2 | 8/2014 | Schraven et al. | |
| 8,835,691 B2 | 9/2014 | Klasovsky et al. | |
| 8,999,684 B2 | 4/2015 | Poetter et al. | |
| 9,012,227 B2 | 4/2015 | Karau et al. | |
| 9,068,202 B2 | 6/2015 | Tran et al. | |
| 9,102,958 B2 | 8/2015 | Botes et al. | |
| 9,150,890 B2 | 10/2015 | Poetter et al. | |
| 9,200,043 B2 | 12/2015 | Poetter et al. | |
| 9,249,435 B2 | 2/2016 | Gielen et al. | |
| 9,562,930 B2 | 2/2017 | Makuth et al. | |
| 9,580,732 B2 | 2/2017 | Poetter et al. | |
| 9,587,231 B2 | 3/2017 | Hom et al. | |
| 9,677,045 B2 | 6/2017 | Pharkya et al. | |

(Continued)

FOREIGN PATENT DOCUMENTS

| | | |
|---|---|---|
| CA | 2 900 293 | 8/2014 |
| EP | 2 292 783 | 3/2011 |

(Continued)

OTHER PUBLICATIONS

Kizer L et al. Application of Functional Genomics to Pathway Optimization for Increased Isoprenoid Production. Applied and Environmental Microbiology, May 2008, p. 3229-3241. vol. 74, No. 10.*

(Continued)

*Primary Examiner* — Paul J Holland
(74) *Attorney, Agent, or Firm* — Law Office of Michael A. Sanzo, LLC

(57) ABSTRACT

The present invention relates to a compound of general formula I

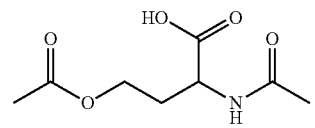

The present invention also relates to a method of producing N-acetyl homoserine and/or derivatives thereof, the method comprising contacting at least one recombinant cell in an aqueous medium with acetate wherein the recombinant cell comprises an increased activity relative to a wild type cell of (a) an enzyme $E_1$, a homoserine dehydrogenase (EC1.1.1.3) and/or an enzyme $E_5$, an aspartokinase (EC2.7.2.4); and (b) an enzyme $E_2$, a homoserine O-acetyl transferase (EC2.3.1.31)

and the acetate is maintained at a concentration of at least about 0.001 g/L in the aqueous medium.

10 Claims, No Drawings

Specification includes a Sequence Listing.

(56) References Cited

U.S. PATENT DOCUMENTS

| | | |
|---|---|---|
| 9,719,117 B2 | 8/2017 | Schaffer et al. |
| 9,765,366 B2 | 9/2017 | Schiemann et al. |
| 9,765,370 B2 | 9/2017 | Hennemann |
| 9,885,060 B2 | 2/2018 | Dennig et al. |
| 9,920,334 B2 | 3/2018 | Haas et al. |
| 10,053,713 B2 | 8/2018 | Pfeffer et al. |
| 10,329,590 B2 | 6/2019 | Haas et al. |
| 2007/0092957 A1 | 4/2007 | Donaldson et al. |
| 2007/0275447 A1 | 11/2007 | Lewis et al. |
| 2008/0057554 A1 | 3/2008 | Huhnke et al. |
| 2010/0137641 A1 | 6/2010 | Iida et al. |
| 2010/0151543 A1 | 6/2010 | Reeves |
| 2010/0324257 A1 | 12/2010 | Karau et al. |
| 2011/0111475 A1 | 5/2011 | Kuhry et al. |
| 2011/0118433 A1 | 5/2011 | Poetter et al. |
| 2011/0171702 A1 | 7/2011 | Reinecke et al. |
| 2011/0229942 A1 | 9/2011 | Campbell |
| 2012/0034665 A1 | 2/2012 | Haas et al. |
| 2012/0045807 A1 | 2/2012 | Simpson et al. |
| 2013/0189750 A1 | 7/2013 | Jin et al. |
| 2013/0203953 A1 | 8/2013 | Pereira et al. |
| 2013/0217060 A1 | 8/2013 | Bramucci |
| 2014/0011249 A1 | 1/2014 | Burgard et al. |
| 2014/0051136 A1 | 2/2014 | Liao et al. |
| 2014/0120587 A1 | 5/2014 | Haas et al. |
| 2014/0178948 A1 | 6/2014 | Schaffer et al. |
| 2014/0186905 A1 | 7/2014 | Schaffer et al. |
| 2014/0256904 A1 | 9/2014 | Schaffer et al. |
| 2014/0273123 A1 | 9/2014 | Tobey et al. |
| 2014/0308717 A1 | 10/2014 | Haas et al. |
| 2015/0010968 A1 | 1/2015 | Engel et al. |
| 2015/0044744 A1 | 2/2015 | Pfeffer et al. |
| 2015/0093798 A1 | 4/2015 | Jung et al. |
| 2015/0099282 A1 | 4/2015 | Haas et al. |
| 2015/0111253 A1 | 4/2015 | Schaffer et al. |
| 2015/0111254 A1 | 4/2015 | Hennemann et al. |
| 2015/0125912 A1 | 5/2015 | Haas et al. |
| 2015/0218600 A1 | 8/2015 | Haas et al. |
| 2015/0267231 A1 | 9/2015 | Haas et al. |
| 2015/0275245 A1 | 10/2015 | Haas et al. |
| 2015/0284747 A1 | 10/2015 | Schiemann et al. |
| 2015/0299741 A1 | 10/2015 | Engel et al. |
| 2015/0353963 A1 | 12/2015 | Haas et al. |
| 2016/0137969 A1 | 5/2016 | Haas et al. |
| 2016/0138058 A1 | 5/2016 | Wittmann et al. |
| 2016/0138061 A1 | 5/2016 | Haas et al. |
| 2016/0177259 A1 | 6/2016 | Haas et al. |
| 2016/0215302 A1 | 7/2016 | Haas et al. |
| 2016/0215304 A1 | 7/2016 | Haas et al. |
| 2016/0244790 A1 | 8/2016 | Haas et al. |
| 2016/0272950 A1 | 9/2016 | Corthals et al. |
| 2016/0326549 A1 | 11/2016 | Dennig et al. |
| 2016/0326555 A1 | 11/2016 | Engel et al. |
| 2017/0130248 A1 | 5/2017 | Reinecke |
| 2017/0145448 A1 | 5/2017 | Schaffer et al. |
| 2017/0183694 A1 | 6/2017 | Pharkya et al. |
| 2017/0204437 A1 | 7/2017 | Haas et al. |
| 2017/0260552 A1 | 9/2017 | Haas et al. |
| 2017/0260553 A1 | 9/2017 | Haas et al. |
| 2018/0127791 A1 | 5/2018 | Schaffer |
| 2018/0135085 A1 | 5/2018 | Haas |
| 2018/0142266 A1 | 5/2018 | Haas et al. |
| 2018/0155743 A1 | 6/2018 | Haas et al. |
| 2018/0208947 A1 | 7/2018 | Haas et al. |
| 2018/0371504 A1 | 12/2018 | Haas et al. |
| 2019/0127321 A1 | 5/2019 | Haas |
| 2019/0127769 A1 | 5/2019 | Haas |
| 2019/0169654 A1 | 6/2019 | Hecker |
| 2020/0231994 A1 | 7/2020 | Haas et al. |

FOREIGN PATENT DOCUMENTS

| | | |
|---|---|---|
| GB | 1009370 | 11/1965 |
| GB | 1113357 | 5/1968 |
| GB | 1563933 | 4/1980 |
| WO | WO 98/00558 | 1/1998 |
| WO | WO 00/14052 | 3/2000 |
| WO | WO 00/20566 | 4/2000 |
| WO | WO 00/68407 | 11/2000 |
| WO | WO 2007/136762 | 11/2007 |
| WO | WO 2008/119082 | 10/2008 |
| WO | WO 2008/148640 | 12/2008 |
| WO | WO 2009/078973 | 6/2009 |
| WO | WO 2009/100434 | 8/2009 |
| WO | WO 2010/115054 | 10/2010 |
| WO | WO 2010/118410 | 10/2010 |
| WO | WO 2012/091479 | 7/2012 |
| WO | WO 2012/099603 | 7/2012 |
| WO | WO 2012/177943 | 12/2012 |
| WO | WO 2014/140336 | 9/2014 |
| WO | WO 2015/110518 | 7/2015 |
| WO | WO 2015/172972 | 11/2015 |
| WO | WO 2015/173059 | 11/2015 |
| WO | WO 2016/008979 | 1/2016 |
| WO | WO 2016/131801 | 8/2016 |
| WO | WO 2016/184656 | 11/2016 |
| WO | WO 2016/184663 | 11/2016 |
| WO | WO 2017/001170 | 1/2017 |
| WO | WO 2017/102952 | 6/2017 |
| WO | WO 2017/202975 | 11/2017 |
| WO | WO 2018/018402 | 2/2018 |
| WO | WO 2018/019245 | 2/2018 |
| WO | WO 2018/019841 | 2/2018 |
| WO | WO 2018/019847 | 2/2018 |
| WO | WO 2018/115333 | 6/2018 |
| WO | WO 2018/115350 | 6/2018 |

OTHER PUBLICATIONS

Prather KLJ et al. De novo biosynthetic pathways: rational design of microbial chemical factories. Current Opinion in Biotechnology 2008, 19:468-474.*
Non Final Office Action for copending U.S. Appl. No. 16/063,256, dated Dec. 3, 2019.
Copending U.S. Appl. No. 14/367,610, filed Dec. 14, 2012, US-2015/0275245 A1, Jan. 10, 2015, Haas.
Copending U.S. Appl. No. 14/400,379, filed May 8, 2013, US-2015/0125912 A1, Oct. 8, 2015, Haas.
Copending U.S. Appl. No. 14/405,050, filed Jun. 14, 2013, US-2015/0267231 A1, Sep. 24, 2015, Haas.
Copending U.S. Appl. No. 14/435,339, filed Nov. 6, 2013, US-2015/0299741 A1, Oct. 22, 2015, Engel.
Copending U.S. Appl. No. 14/763,378, filed Jan. 10, 2014, US-2015/0353963 A1, Dec. 10, 2015, Haas.
Copending U.S. Appl. No. 14/898,417, filed May 30, 2014, US-2016/0138058 A1, May 19, 2016, Wittmann.
Copending U.S. Appl. No. 14/898,679, filed Jun. 17, 2014, US-2016/0137969 A1, May 19, 2016, Haas.
Copending U.S. Appl. No. 14/969,891, filed Dec. 15, 2015, US-2016/0177259 A1, Jun. 23, 2016, Haas.
Copending U.S. Appl. No. 15/009,425, filed Jan. 28, 2016, US-2016/0215302 A1, Jul. 28, 2016, Haas.
Copending U.S. Appl. No. 15/359,932, filed Nov. 23, 2016, US-2017/0145448 A1, May 25, 2017, Schaffer.
Copending U.S. Appl. No. 16/320,836, filed Jul. 25, 2017, US-2019/0169654 A1, Jun. 6, 2019, Hecker.
Response to Non Final Office Action filed Aug. 28, 2019 for copending U.S. Appl. No. 16/063,256.
Notice of Appeal filed Sep. 18, 2019 for copending U.S. Appl. No. 15/326,546.
Response to Non Final Office Action for copending U.S. Appl. No. 16/063,256, filed Mar. 3, 2020.
Response to Restriction Requirement for copending U.S. Appl. No. 16/304,660, filed Aug. 9, 2020.
Non Final Office Action for copending U.S. Appl. No. 16/304,660, dated Sep. 9, 2020.
Non Final Office Action for copending U.S. Appl. No. 16/063,256, dated Jun. 5, 2020.
Restriction Requirement for copending U.S. Appl. No. 16/304,660, dated Jun. 8, 2020.

(56) References Cited

OTHER PUBLICATIONS

International Search Report for PCT/ EP2017/068841 (international counterpart of U.S. Appl. No. 16/320,097), filed Jul. 26, 2017.
Written Opinion of the International Searching Authority for PCT/ EP2017/068841 (international counterpart of U.S. Appl. No. 16/320,097), filed Jul. 26, 2017.
International Preliminary Report on Patentability PCT/ EP2017/ 068841 (international counterpart of U.S. Appl. No. 16/320,097), filed Jul. 26, 2017.
European Search Report and Opinion for EP 16 18 1431(European counterpart of U.S. Appl. No. 16/320,097), filed Jul. 27, 2016.
International Search Report for PCT/EP2015/066174 (international counterpart of copending U.S. Appl. No. 15/326,546), filed Jul. 15, 2015.
Written Opinion of the International Searching Authority for PCT/ EP2015/066174 (international counterpart of copending U.S. Appl. No. 15/326,546), filed Jul. 15, 2015.
International Preliminary Report on Patentability for PCT/EP2015/ 066174 (international counterpart of copending U.S. Appl. No. 15/326,546), filed Jul. 15, 2015.
European Search Report for EP 14 17 7492 (European counterpart of copending U.S. Appl. No. 15/326,546), filed Jul. 17, 2014.
European Search Opinion for EP 14 17 7492 (European counterpart of copending U.S. Appl. No. 15/326,546), filed Jul. 17, 2014.
International Search Report for PCT/EP2016/081202 (international counterpart of copending U.S. Appl. No. 16/063,256), filed Dec. 15, 2016.
Written Opinion of the International Searching Authority for PCT/ EP2016/081202 (international counterpart of copending U.S. Appl. No. 16/063,256), filed Dec. 15, 2016.
International Preliminary Report on Patentability for PCT/EP2016/ 081202 (international counterpart of copending U.S. Appl. No. 16/063,256), filed Dec. 15, 2016.
European Search Report and Opinion for EP 15 20 0673 (European counterpart of copending U.S. Appl. No. 16/063,256), filed Jul. 27, 2016.
International Search Report for PCT/ EP2017/062642 (international counterpart of copending U.S. Appl. No. 16/304,660), filed May 24, 2017.
Written Opinion of the International Searching Authority for PCT/ EP2017/062642 (international counterpart of copending U.S. Appl. No. 16/304,660), filed May 24, 2017.
International Preliminary Report on Patentability for PCT/ EP2017/ 062642 (international counterpart of copending U.S. Appl. No. 16/304,660), filed May 24, 2017.
European Search Report and Opinion for EP 16 17 1624 (European counterpart of copending U.S. Appl. No. 16/304,660), filed May 27, 2016.
Restriction Requirement for copending U.S. Appl. No. 15/326,546, dated Jul. 28, 2017.
Response to Restriction Requirement for copending U.S. Appl. No. 15/326,546, filed Sep. 26, 2017.
Office Action for copending U.S. Appl. No. 15/326,546, dated Mar. 14, 2018.
Response to Office Action for copending U.S. Appl. No. 15/326,546, filed Jul. 7, 2018.
Final Office Action for copending U.S. Appl. No. 15/326,546, dated Oct. 23, 2018.
Response to Final Office Action for copending U.S. Appl. No. 15/326,546, filed Jan. 22, 2019.
Advisory Action for copending U.S. Appl. No. 15/326,546, dated Feb. 5, 2019.
Amendment, Response and RCE for copending U.S. Appl. No. 15/326,546, filed Mar. 10, 2019.
Restriction Requirement for copending U.S. Appl. No. 16/063,256, dated Dec. 26, 2018.
Response to Restriction Requirement for copending copending U.S. Appl. No. 16/063,256, filed Feb. 24, 2019.

Ato, et al., "Enrichment of amino acid-oxidizing acetate-reducing bacteria," *Journal of Bioscience and Bioengineering* 118(2):160-165 (2014).
Born, et al., "Enzyme-Catalyzed Acylation of Homoserine: Mechanistic Characterization of the *Haemophilus influenzae* met2-Encoded Homoserine Transacetylase," *Biochemistry* 39(29):8556-8564 (Jul. 2000).
Drake and Küsel, "Acetogenic clostridia," In: Dürre, P. (ed.), Handbook on Clostridia, pp. 719-746; CRC Press, Boca Raton, Florida (2005).
Drake, et al., "Acetogenic Prokaryotes," *Prokaryotes* 2:354-420 Chapter 1.13 (2006).
Galaction, et al., "Direct Extraction of Propionic Acid from *Propionibacterium acidipropionici* Broths with Tri-n-octylamine," *Chem. Eng. Technol.* 35(9):1657-1663 (2012).
Kandasamy, et al., "Engineering *Escherichia coli* with acrylate pathway genes for propionic acid synthesis and its impact on mixed-acid fermentation," *Appl. Microbiol. Biotechnol.* 971191-1200 (2013).
Keshav, et al., "Recovery of propionic acid from an aqueous stream by reactive extraction: effect of diluents," *Desalanation* 244 (1-3): 12-23 (2009).
Koch, "Growth Measurement" Methods for General and Molecular Biology; Chapter 11; Gerhardt (ed); pp. 248-277 (2004).
Müller, et al., "Molecular and Cellular Biology of Acetogenic Bacteria," From: Strict and Facultative Anaerobes: Medical and Environmental Aspects; Chapter 14; pp. 251-281 (2004).
Sakai, et al., "Ethanol production from $H_2$ and $CO_2$ by a newly isolated thermophilic bacterium, *Moorella* sp. HUC22-1," *Biotechnology Letters* 26(20):1607-1612 (Oct. 2004).
Stowers, et al., "Development of an industrializable fermentation process for propionic acid production," *J. Ind. Microbiol. Biotechnol.* 41:837-852 (2014).
Tholozan, et al., "*Clostridium neopropionicum* sp. nov., a strict anaerobic bacterium fermenting ethanol to propionate through acrylate pathway," *Arch. Microbiol.* 157:249-257 (1992).
Willke, "Methionine production—a critical review," *Appl. Microbiol. Biotechnol.* 98(24):9893-9914 (Nov. 2014).
Wood, et al., "Life with CO or $CO_2$ and $H_2$ as a source of carbon energy," *FASEB J* 5(2):156-163 (Feb. 1991).
Zhang, et al., "$_D$-Lactic acid biosynthesis from biomass-derived sugars via *Lactobacillus delbrueckii* fermentation," *Bioprocess Biosyst Eng* 36:1897-1904 (2013).
Copending U.S. Appl. No. 15/326,546, filed Jan. 16, 2019, US-2017/ 0204437 A1, Jul. 20, 2017, Haas.
Copending U.S. Appl. No. 16/063,256, filed Jun. 16, 2018, US-2018/ 0371504 A1, Dec. 27, 2018, Haas.
Copending U.S. Appl. No. 16/304,660, filed Nov. 26, 2018, Haas.
Non Final Office Action for copending U.S. Appl. No. 16/063,256, dated May 29, 2019.
Non Final Office Action for copending U.S. Appl. No. 15/326,546, dated Jun. 19, 2019.
Adrio, et al., "Recombinant organisms for production of industrial products," *Bioengineered Bugs* 1(2):116-131 (Mar./Apr. 2010).
Balabanova, et al., "Genetically modified proteins: functional improvement and chimeragenesis," *Bioengineered* 6(5):262-274 (Sep./Oct. 2015).
Bertsch, et al., "Bioenergetic constraints for conversion of syngas to biofuels in acetogenic bacteria," *Biotechnol Biofuels* 8(210):1-12 (2015).
Dürre, "Butanol formation from gaseous substances," *FEMS Microbiology Letters* 363:1-7 (2016).
Schiel-Bengelsdorf, et al., "Pathway engineering and synthetic biology using acetogens," *FEBS Letters* 586:2191-2198 ((2012).
Tamano, "Enhancing microbial metabolite and enzyme production: current strategies and challenges," *Frontiers in Microbiology* 5(718):1-6 (Dec. 2014).
Wiechmann, et al., "Synthesis of Acetyl-CoA from Carbon Dioxide in Acetogenic Bacteria," Handbook of Hydrocarbon and Lipid Microbiology, pp. 1-32, (2017).
Copending U.S. Appl. No. 15/565,451, filed Oct. 10, 2017, US-2018/ 0127791 A1, May 10, 2018, Schaffer.

(56) References Cited

OTHER PUBLICATIONS

Copending U.S. Appl. No. 15/574,334, filed Nov. 15, 2017, US-2018/0135085 A1, May 17, 2018, Haas.
Copending U.S. Appl. No. 16/094,334, filed Oct. 17, 2018, US-2019/0127769 A1, May 17, 2019, Haas.
Copending U.S. Appl. No. 16/095,517, filed Oct. 22, 2018, US-2019/0127321 A1, May 17, 2019, Haas.
Abrini, et al., "*Clostridium autoethanogenum*, sp. nov., an anaerobic bacterium that produces ethanol from carbon monoxide," *Arch Microbiol* 161(4):345-351 (Apr. 1994).
Anderlund, et al., "Expression of the *Escherichia coli* pntA and pntB Genes, Encoding Nicotinamide Nucleotide Transhydrogenase, in *Saccharomyces cerevisiae* and Its Effect on Product Formation during Anaerobic Glucose Fermentation," *Appl. Environ. Microbiol.* 65(6):2333-2340 (Jun. 1999).
Andreesen, et al., "Fermentation of Glucose, Fructose, and Xylose by *Clostridium thermoaceticum*: Effect of Metals on Growth Yield, Enzymes, and the Synthesis of Acetate from $CO_2$," *Journal of Bacteriology* 114(2):743-751 (May 1973).
Baba, et al., "Construction of *Escherichia coli* K-12 in-frame, single gene knockout mutants: the Keio collection," *Molecular Systems Biology* 21:1-11 (Feb. 2006).
Becker, et al., "A generic system for the *Escherichia coli* cell-surface display of lipolytic enzymes," *FEBS Letters* 575(5):1177-1182 (Feb. 2005).
Bornstein, et al., "The energy metabolism of *Clostridium kluyveri* and the synthesis of fatty acids," *J Biol Chem* 172(2):659-669 (Feb. 1948).
Byoung, et al., "In situ extractive fermentation for the production of hexanoic acid from galactitol by *Clostridium* sp. BS-1," *Enzyme and Microbial Technology* 53(3)143-151 (Aug. 2013).
Cotter, et al., "Ethanol and acetate production by *Clostridium ljungadahlii* and *Clostridium autoethanogenum* using resting cells," *Bioprocess Biosyst Eng* 32(3):369-380 (Apr. 2009).
Dar, et al., "Competition and coexistence of sulfate-reducing bacteria, acetogens and methanogens in a lab-scale anaerobic bioreactor as affected by changing substrate to sulfate ratio," *Appl Microbiol Biotechnol* 78(6):1045-1055 (Feb. 2008).
De Lorenzo, et al., "Mini-Tn5 Transposon Derivatives for Insertion Mutagenesis, Promoter Probing, and Chromosomal Insertion of Cloned DNA in Gram-Negative Eubacteria," *Journal of Bacteriology* 172(11):6568-6572 (Nov. 1990).
Demler, et al., "Reaction Engineering Analysis of Hydrogenotrophic Production of Acetic Acid by *Acetobacterium woodii*," *Biotechnology and Bioengineering* 108(2):470-474 (Feb. 2011).
Devos, et al., "Practical Limits of Function Prediction," *Proteins: Structure, Function and Genetics* 41:98-107 (2000).
Ding, et al., "Caproate formation in mixed-culture fermentative hydrogen production," *Bioresource Technology* 101(24):9550-9559 (Dec. 2010).
Fukaya, et al., "The aarC Gene Responsible for Acetic Acid Assimilation Confers Acetic Acid Resistance on *Acetobacter aceti*," *Journal of Fermentation and Bioengineering* 76(4):270-275 (Jan. 1993).
Hatefi, et al., "Dehydrogenase and transhydrogenase properties of the soluble NADH dehydrogenase of bovine heart mitochondria," *Proc. Natl. Acad. Sci. USA* 74(3):846-850 (Mar. 1977).
Kaulmann, et al., "Substrate spectrum of ω-transaminase from *Chromobacteria violaceum* DSM30191 and its potential for biocatalysis," *Enzyme and Microbial Technology* 41(5):628-637 (Oct. 2007).
Kenealy, et al., "Studies on the substrate range of *Clostridium kluyveri*; the use of propanol and succinate," *Arch Microbiol* 141(3):187-194 (Apr. 1985).
Kieun, et al., "In situ Biphasic Extractive Fermentation for Hexanoic Acid Production from Sucrose by *Megasphaera elsdenii* NCIMB 702410," *Appl Biochem Biotechnol* 171(5):1094-1107 (Nov. 2013).
Kisselev, "Polypeptide Release Factors in Prokaryotes and Eukaryotes: Same Function, Different Structure," *Structure* 10:8-9 (Jan. 2002).
Kojima, et al., "Purification and Characterization of the Lipase from *Pseudomonas fluorescens* HU380," *Journal of Bioscience and Bioengineering* 96(3):219-226 (accepted May 2003).
Levy, et al., "Biorefining of biomass to liquid fuels and organic chemicals," *Enzyme and Microbial Technology* 3(3):207-215 (Jul. 1981).
Levy, et al., "Kolbe Electrolysis of Mixtures of Aliphatic Organic Acids," *Journal of the Electrochemical Society* 131(4):773-777 (Apr. 1984).
Li, a dissertation, "Production of Acetic Acid from Synthesis Gas with Mixed Acetogenic Microorganisms," Texas A & M University, Chemical Engineering (May 2002).
Mieke, et al., "Bioelectrochemical Production of Caproate and Caprylate from Acetate by Mixed Cultures," *ACS Sustainable Chem Eng* 1(5):513-518 (May 2013).
Morinaga, et al., "The production of acetic acid from carbon dioxide and hydrogen by an anaerobic bacterium," *Journal of Biotechnology* 14(2):187-194 (May 1990).
Mullins, et al., "A Specialized Citric Acid Cycle Requiring Succinyl-Coenzyme A (CoA):Acetate CoA-Transferase (AarC) Confers Acetic Acid Resistance on the Acidophile *Acetobacter aceti*," *Journal of Bacteriology* 190(14):4933-4940 (Jul. 2008).
Overkamp, et al., "Cloning and characterization of eight cytochrome P450 cDNAs from chickpea (*Cicer arietnum* L.) cell suspension cultures," *Plant Science* 155(1):101-108 (Jun. 2000).
Panke, et al., "Engineering of a Stable Whole-Cell Biocatalyst Capable of (S)-Styrene Oxide Formation for Continuous Two-Liquid-Phase Applications," *Applied and Environmental Microbiology* 65(12):5619-5623 (Dec. 1999).
Perez, et al., "Biocatalytic Reduction of Short-Chain Carboxylic Acids Into Their Corresponding Alcohols With Syngas Fermentation," *Biotechnology and Bioengineering* 110(4):1066-1077 (Apr. 2013).
Riesenberg, et al., "High cell density fermentation of recombinant *Escherichia coli* expressing human interferon alpha 1," *Appl Microbiol Biotechnol* 34(1):77-82 (accepted Jun. 1990).
Saxena, et al., "Effect of trace metals on ehtanol production from synthesis gas by the ethanologenic acetogen, *Clostridium ragsdalei*," *J Ind Microbiol Biotechnol* 38(4):513-521 (accepted Jul. 2010).
Scheps, et al., "Regioselective ω-hydroxylation of medium-chain n-alkanes and primary alcohols by CYP153 enzymes from *Mycobacterium marinum* and *Polaromonas* sp. strain JS666," *Organic & Biomolecular Chemistry* 9:6727-6733 (Oct. 2011).
Schmidt, et al., "Production of Acetic Acid from Hydrogen and Carbon Dioxide by *Clostridium* Species ATCC 29797," *Chem Eng Commun* 45(1-6):61-73 (May 1986).
Seedorf, et al., "The genome of *Clostridium kluyveri*, a strict anaerobe with unique metabolic features," *Proc Natl Acad Sci USA* 105(6):2128-2133 (Feb. 2008).
Seedorf, et al., "*Clostridium kluyveri* DSM 555 complete genome," retrieved from GenBank, database accession No. CP0000673, (Jan. 2014).
Sim, et al., "Optimization of acetic acid production from systhesis gas by chemolithotrophic bacterium—*Clostridium aceticum* using statistical approach," *Bioresource Techn.* 99(8):2724-2735 (May 2008).
Smits, et al., "Functional Analysis of Alkane Hydroxylases from Gram-Negative and Gram-Positive Bacteria," *Journal of Bacteriology* 184(6):1733-1742 (Mar. 2002).
Stadtman, et al., "Fatty Acid Synthesis by Enzyme Preparations of *Clostridium kluyveri*," *J Biol Chem* 184(2):769-794 (Jun. 1950).
Stadtman, et al., "Tracer Experiments on the Mechanism of Synthesis of Valeric and Caproic Acids by *Clostridium kluyveri*," *J Biol Chem* 178(2):677-682 (Jun. 1948).
Stadtman, et al., "Discussion," *Federation Proceedings* 12(3):692-693 (Sep. 1953).
Stadtman, "The Coenzyme A Transphorase System in *Clostridium kluyveri*," *J. Biol. Chem.* 203(1):501-512 (Jul. 1953).
Steinbusch, et al., "Biological formation of caproate and caprylate from acetate: fuel and chemical production from low grade biomass," *Energy and Environmental Science* 4:216-224 (accepted Oct. 2010).

(56) References Cited

OTHER PUBLICATIONS

Van Beilen, et al., "Diversity of Alkane Hydroxylase Systems in the Environment," *Oil & Gas Science and Technology* 58(4):427-440 (2003).

Vaysse, et al., Chain-length selectivity of various lipases during hydrolysis, esterification and alcoholysis in biphasic aqueous medium, *Enzyme and Microbial Technology* 31(5):648-655 (Oct. 2002).

Vega, et al., "Study of Gaseous Substrate Fermentations: Carbon Monoxide Conversion to Acette. 1. Batch Culture," *Biotechnology and Bioengineering* 34(6):774-784 (Sep. 1989).

Wadhawan, et al., "Biphasic sonselectrosynthesis. A review," *Pure Appl Chem* 73(12):1947-1955 (Apr. 2001).

Whisstock, et al., "Prediction of protein function from protein sequence and structure," *Quarterly Reviews of Biophysics* 36(3):307-340 (Aug. 2003).

Witkowski, et al., "Conversion of a ß-Ketoacyl Synthase to a Malonyl Decarboxylase by Replacement of the Active-Site Cysteine with Glutamine," *Biochemisty* 38(36):11643-11650 (Sep. 1999).

Wu, et al., "Microbial composition and characterization of prevalent methanogens and acetogens isolated from syntrophic methanogenic granules," *Appl Microbiol Biotechnol* 38(2):282-290 (Nov. 1992).

Younesi, et al., "Ethanol and acetate production from synthesis gas via fermentation processes using anaerobic bacterium, *Clostridium ljungadahlii*," *Biochemical Engineering Journal* 27(2):110-119 (Dec. 2005).

Zhang, et al., "Fatty acids production from hydrogen and carbon dioxide by mixed culture in the biofilm reactor," *Water Research* 47(16):6122-6129 (available online Jul. 2013).

Amendment & Response to Office Action for copending U.S. Appl. No. 16/063,256, filed Oct. 8, 2020.

Non Final Office Action for copending U.S. Appl. No. 16/063,256, dated Jan. 8, 2021; See especially pp. 9-13, sequences and accompanying text.

Amendment & Response to Office Action for copending U.S. Appl. No. 16/304,660, filed Jan. 11, 2021.

Non Final Office for copending U.S. Appl. No. 16/304,660, dated Feb. 4, 2021.

Amendment & Response to Office Action for copending U.S. Appl. No. 16/063,256, filed May 2, 2021.

Amendment & Response to Office Action for copending U.S. Appl. No. 16/304,660, filed May 13, 2021.

Final Office Action for copending U.S. Appl. No. 16/304,660, dated May 21, 2021.

Notice of Allowance for copending U.S. Appl. No. 16/063,256, dated Jul. 12, 2021.

\* cited by examiner

N-ACETYL HOMOSERINE

CROSS REFERENCE TO RELATED APPLICATIONS

The present application is US national stage of international application PCT/EP2017/068841, which had an international filing date of Jul. 26, 2017, and which was published in English on Feb. 1, 2018. Priority is claimed to European application 16181431.4, filed on Jul. 27, 2016. The contents of these prior applications is hereby incorporated by reference in their entirety.

FIELD OF THE INVENTION

The present invention relates to a biotechnological method for producing N-acetyl homoserine and derivatives thereof. In particular, N-acetyl homoserine and derivatives thereof may be used as a precursor for producing methionine.

BACKGROUND OF THE INVENTION

Amino acids are especially useful as additives in animal feed and as nutritional supplements for human beings. They can also be used in infusion solutions and may function as synthetic intermediates for the manufacture of pharmaceuticals and agricultural chemicals. Compounds such as cysteine, homocysteine, methionine and S-adenosylmethionine are usually industrially produced to be used as food or feed additives and also in pharmaceuticals. In particular, methionine, an essential amino acid, which cannot be synthesized by animals, plays an important role in many body functions. D,L-methionine is presently being produced by chemical synthesis from hydrogen cyanide, acrolein and methyl mercaptan. These petroleum based starting materials such as acrolein and methyl mercaptan are obtained by cracking gasoline or petroleum which is bad for the environment. Also, since the costs for these starting materials will be linked to the price of petroleum, with the expected increase in petroleum prices in the future, prices of methionine will also increase relative to the increase in the petroleum prices.

There are several chemical means of producing methionine. In one example, 3-methylthiopropanal is used as a raw material with hydrocyanic acid in the presence of a base. The reaction results in ammonium carbonate, which is then hydrolysed. In this method, carbon dioxide is introduced into the reaction liquid after hydrolysis, whereby crystallization occurs and methionine is separated as a crystal. Carbon dioxide and hydrogen are used as raw materials for producing methionine using this method. However, a large amount of hydrogen is left over, making this method inefficient.

Methionine may also include N-acetyl methionine. Normally, N-acetyl methionine may be formed chemically using acetylating compounds like acetanhydride. This is an additional step and forms a by-product like acetate. With acetic acid release, the N-acetyl methionine partly absorbs the scent of acetate. The methionine produced using this method thus has a trace of acetate.

With the increasing methionine demand, thus microbial production of all types of methionine, including N-acetyl methionine is always an attractive alternative. Accordingly, there is a need in the art for a cheaper and more efficient biotechnological means of producing N-acetyl methionine.

DESCRIPTION OF THE INVENTION

The present invention relates to a new N-acetyl homoserine derivative and a means of producing this compound and other related compounds. In particular, the new N-acetyl homoserine derivative may be O-acetyl-N-acetamido-DL-homoserine. The present invention also relates to a means of producing N-acetamido-DL-homoserine. N-acetyl homoserine and derivatives thereof may be produced using a biotechnological method that comprises the use of a recombinant cell that has been genetically modified to increase the activity of an enzyme $E_1$, homoserine dehydrogenase (EC1.1.1.3) and/or an enzyme $E_5$, an aspartokinase (EC2.7.2.4); and an enzyme $E_2$, a homoserine O-acetyl transferase (EC2.3.1.31). These N-acetyl homoserine and derivatives thereof may then be used as the precursor for the production of methionine.

According to one aspect of the present invention, there is provided a compound of general formula I

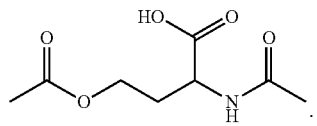

The compound according to any aspect of the present invention may be O-acetyl-N-acetamido-L-homoserine or O-acetyl-N-acetamido-D-homoserine. O-acetyl-N-acetamido-DL-homoserine may be used as a precursor for the production of methionine. Depending on whether the D- or L-O-acetyl-N-acetamido-homoserine is formed, the compound will be used for the production of D or L-methionine respectively.

According to another aspect of the present invention, there is provided a method of producing N-acetyl homoserine and/or derivatives thereof, the method comprising
  contacting at least one recombinant cell with a carbon source in an aqueous medium wherein the recombinant cell comprises an increased activity relative to a wild type cell of
    (a) an enzyme $E_1$, a homoserine dehydrogenase (EC1.1.1.3); and/or an enzyme $E_5$, an aspartokinase (EC2.7.2.4); and
    (b) an enzyme $E_2$, a homoserine O-acetyl transferase (EC2.3.1.31).

The carbon source may comprise free acetate or a substrate that can be converted to acetate. For example, the aqueous medium comprises at least one carbon source for fermentation of the cells according to any aspect of the present invention to produce N-acetyl homoserine and/or derivatives thereof. The aqueous medium additionally comprises free acetate. In one example, the aqueous medium comprises at least one carbon source for fermentation of the cells according to any aspect of the present invention to produce N-acetyl homoserine and/or derivatives thereof and free acetate.

Carbon sources for fermentation of the cells according to any aspect of the present invention may include any carbohydrate such as glucose, sucrose, lactose, fructose, maltose, starch, cellulose; fat such as soybean oil, sunflower oil, castor oil and coconut oil; fatty acid such as palmitic acid, stearic acid, and linoleic acid; alcohol such as glycerol and ethanol; and organic acid such as acetic acid. One of these compounds or a mixture thereof can be used as a carbon source. Carbon source may also include acetate. In one example, the carbon source is acetate only.

The term "acetate" as used herein, refers to both acetic acid and salts thereof ($CH_3$—COO—), which results inevitably, because as known in the art, since the microorganisms work in an aqueous environment, and there is always a balance between salt and acid present. The ratio of molecular acetic acid to acetate is dependent upon the pH of the system, i.e., at a constant "acetate" concentration, the lower the pH, the higher the molecular acetic acid concentration relative to acetate salt.

The acetate may be exogenously produced. This means that the recombinant cell used according to any aspect of the present invention may not produce acetate on its own. Acetate may thus be exogenously produced and introduced to the aqueous medium prior to contacting the cell with the carbon source. In particular, the aqueous medium comprising the recombinant cell already comprises acetate before the recombinant cell begins to produce N-acetyl homoserine and/or derivatives thereof.

More in particular, the acetate may be used as the starting material in the presence of a carbon source such as carbon dioxide and/or carbon monoxide by the recombinant cell to produce N-acetyl homoserine and/or derivatives thereof further in the presence of acetate. The acetate may not be used up in the production of N-acetyl homoserine and/or derivatives thereof. In particular, the acetate may be used to improve the selectivity of production of N-acetyl homoserine and/or derivatives thereof by the recombinant cell. The presence of the acetate in the reaction mixture may thus be maintained to encourage the production N-acetyl homoserine and/or derivatives thereof and not the by-products.

Rather than waiting for the cell to produce endogenous acetate, exogenously produced acetate may be present initially in the aqueous medium. In particular, the term "exogenously produced" acetate, as used herein, refers to acetate of ethanol produced or purified in a separate reaction vessel prior to contacting the recombinant cell, by contrast to acetate produced by the cell. In another example, the term "exogenously produced" acetate comprises acetate produced by an acetogenic bacterial cell prior to contact with the recombinant cell according to any aspect of the present invention. In one example, the acetate is removed from the reaction vessel and then brought into contact with the recombinant in a second reaction vessel. In another example, the recombinant cells and acetogenic cells are in the same reaction vessel. The acetate may be produced by the acetogenic cell brought into contact with at least one carbon source. In the presence of this exogenous acetate, the recombinant cell may convert the exogenously produced acetate to N-acetyl homoserine and/or derivatives thereof. More in particular, the concentration of exogenously produced acetate may be maintained in the aqueous medium at the value or range of values present initially as long as the reaction catalysed by the recombinant cell continues. Even more in particular, the acetate in the aqueous medium as whole is regarded as exogenous as long as more than 80, particularly more than 90% of the total acetate present in the aqueous medium is accounted for by exogenously produced acetate.

The concentration of the acetate in the aqueous medium according to any aspect of the present invention may be a crucial aspect. The concentration of the acetate in the aqueous medium used according to any aspect of the present invention may be maintained at the specific concentrations mentioned. In particular, the concentration of acetate may be at least about 1 ppm (i.e. 0.001 g/L) in the aqueous medium. This concentration may be maintained in the aqueous medium. In one example, the concentration of acetate may at least substantially maintained at the concentration mentioned above, for example at least above 0.0 g/L and equal to or above about 0.001 g/L, 0.002 g/L, 0.003 g/L, 0.004 g/L, 0.005 g/L, 0.01 g/L, 0.015 g/L, 0.02 g/L, 0.025 g/L, 0.030 g/L, 0.050 g/L, and the like. The aqueous medium comprises at least 0.001 g/L acetate. In particular, the acetate concentration may be maintained between 0.01 g/L to 10 g/L in the aqueous medium. More in particular, the acetate concentration is maintained between 0.01/L to 7 g/L in the aqueous medium. Even more in particular, the acetate concentration may be maintained at about 2 g/L in the aqueous medium. A skilled person would be capable of maintaining the concentration of acetate by consistently checking the concentration of acetate in the aqueous medium and feeding acetate when the concentration goes below the required concentration or stopping the feeding when the concentration of acetate is above the desired concentration.

In one example, the concentration of acetate may be 34-100% of the total carbon source in the aqueous medium. In particular, the concentration of acetate may be about 35, 40, 45, 50, 55, 60, 65, 70, 75, 80, 85, 90, 95 or 100% of the total carbon source in the aqueous medium. More in particular, the concentration of acetate may be about 35-100, 40-100, 45-100, 50-100, 35-90, 40-90 or 45-90% of the total carbon source in the aqueous medium.

The term 'about' as used herein refers to a variation within 20 percent. In particular, the term "about" as used herein refers to +/−20%, more in particular, +/−10%, even more in particular, +/−5% of a given measurement or value.

A skilled person would be capable of maintaining the concentration acetate at the desired level by methods known in the art. In particular, the skilled person would regularly measure the concentration of acetate in the aqueous medium and adjust the concentration of acetate accordingly by adding a higher or lower concentration of acetate into the medium. In one example, the acetate may be measured using NMR. In particular, the concentration of acetate may be measured using semi-quantitative $^1$H-NMR spectroscopy. As an internal quantification standard sodium trimethylsilylpropionate (T(M)SP) may be used. In another example, the concentration of acetate may be measured using an enzyme kit (Article number: 10148261035) from R-Biopharm following the manufacturer's instructions. In one example, the acetate may be added to the aqueous medium in in a continuous flow separately from the continuous feed of the aqueous medium. In another example, acetate may be part of the culture medium that is being topped up. In particular, acetate may be fed to the aqueous medium as part of the nutrient feed or separately. Whichever route is taken to feed acetate to the aqueous medium, a skilled person would understand the means to maintain the concentration of acetate in the aqueous medium. In one example, the acetate concentration in the medium may be maintained by topping up the acetate every about 20 hours of fermentation. In another example, the top up of acetate in the medium may take place every about 5, 10, 15, 20, 25, 30 hours from the beginning of the culturing and/or fermentation process. In another example, the acetate may not necessarily be needed to be topped up as acetate may not be used in the method of producing N-acetyl homoserine and/or derivatives thereof.

In one example, the concentration of acetate in the aqueous medium is maintained at any of the concentrations used according to any aspect of the present invention for 80% of the reaction period. In another example, the concentration of acetate may be maintained for 50%, 55%, 60%, 65%, 70%, 75%, 85%, 90%, 95% or 100% of the reaction time. In this regard, 'reaction time' refers to the period during with a process takes place. In particular, reaction time refers to the period of time from when a reaction starts to when the reaction ends and/or is completed, i.e. where the substrate is used up. In one example, the substrate may be acetate, and the reaction is completed when the acetate in the fermenter is used up and the reaction stops and no further acetate is fed into the fermenter. Therefore, the reaction time refers to the period from which the fermentation starts (i.e. when the acetate first comes into contact with at least one recombinant cell in a fermenter in suitable fermentation conditions) to when the fermentation ends (i.e. when there is no more acetate in the fermenter and/or when there is another limiting factor in the fermenter that stops the reaction from continuing). In one example, the reaction period may be for 24 hr, 42 hr, 72 hr, 96 hr and the like. In another example, the reaction period may be for 90, 91, 92, 93, 94, 95, 97 and the like hours.

The acetate from the method according to any aspect of the present invention may be recycled. In particular, this means that the N-acetyl homoserine and/or derivatives thereof formed according to any aspect of the present invention may be allowed to accumulate and then separated by means known in the art. The acetate may thus be maintained in the reaction mixture and recycled. The N-acetyl homoserine and/or derivatives thereof formed may be removed in a batch-wise mode or in a continuous mode. In the latter case, the N-acetyl homoserine and/or derivatives thereof formed are removed continuously by a separation step known in the art.

The method according to any aspect of the present invention may comprise a step of
    extracting N-acetyl homoserine and/or derivatives thereof from the aqueous medium.

It may be easier to isolate N-acetyl homoserine and/or derivatives thereof relative to the respective O-acetyl compounds because it is less polar and the end product N-acetyl methionine is known to have positive performance properties.

N-acetyl homoserine and/or derivatives thereof may be used in the formation of N-acetyl methionine. Normally N-acetylmethionine is formed chemically using acetylating compounds like acetic anhydride. This is an additional step and forms a by-product like acetate.

Means of extracting N-acetyl homoserine and/or derivatives thereof may include any method of extraction known in the art. The method of extracting may include an aqueous two-phase system for example comprising polyethylene glycol, or amines, capillary electrolysis, chromatography and the like. In one example, when chromatography is used as the means of extraction, ion exchange columns may be used. In another example, N-acetyl homoserine and/or derivatives thereof may be precipitated using pH shifts. N-acetyl homoserine and/or derivatives thereof may be considered to behave like a carboxylic acid. Therefore, any method known in the art to extract carboxylic acids can be used to extract N-acetyl homoserine and/or derivatives thereof. A skilled person may easily identify the most suitable means of extracting N-acetyl homoserine and/or derivatives thereof by simple trial and error.

The phrase "wild type" as used herein in conjunction with a cell or microorganism may denote a cell with a genome make-up that is in a form as seen naturally in the wild. The term may be applicable for both the whole cell and for individual genes. The term 'wild type' may thus also include cells which have been genetically modified in other aspects (i.e. with regard to one or more genes) but not in relation to the genes of interest. The term "wild type" therefore does not include such cells where the gene sequences of the specific genes of interest have been altered at least partially by man using recombinant methods. A wild type cell according to any aspect of the present invention thus refers to a cell that has no genetic mutation with respect to the whole genome and/or a particular gene brought about by human means. Therefore, in one example, a wild type cell with respect to enzyme $E_1$ may refer to a cell that has the natural/non-altered expression of the enzyme $E_1$ in the cell. The wild type cell with respect to enzyme $E_2$, $E_3$, $E_4$, $E_5$, etc. may be interpreted the same way and may refer to a cell that has the natural/non-altered expression of the enzyme $E_2$, $E_3$, $E_4$, $E_5$, etc. respectively in the cell.

Any of the enzymes used according to any aspect of the present invention, may be an isolated enzyme. In particular, the enzymes used according to any aspect of the present invention may be used in an active state and in the presence of all cofactors, substrates, auxiliary and/or activating polypeptides or factors essential for its activity. The term "isolated", as used herein, means that the enzyme of interest is enriched compared to the cell in which it occurs naturally. The enzyme may be enriched by SDS polyacrylamide electrophoresis and/or activity assays. For example, the enzyme of interest may constitute more than 5, 10, 20, 50, 75, 80, 85, 90, 95 or 99 percent of all the polypeptides present in the preparation as judged by visual inspection of a polyacrylamide gel following staining with Coomassie blue dye.

The enzyme used according to any aspect of the present invention may be recombinant. The term "recombinant" as used herein, refers to a molecule or is encoded by such a molecule, particularly a polypeptide or nucleic acid that, as such, does not occur naturally but is the result of genetic engineering or refers to a cell that comprises a recombinant molecule. For example, a nucleic acid molecule is recombinant if it comprises a promoter functionally linked to a sequence encoding a catalytically active polypeptide and the promoter has been engineered such that the catalytically active polypeptide is overexpressed relative to the level of the polypeptide in the corresponding wild type cell that comprises the original unaltered nucleic acid molecule. Similarly, "a recombinant cell" as used herein refers to a prokaryotic or eukaryotic microorganism strain that has been genetically modified to be genetically different from the wild type cell or microorganism. In particular, the recombinant cell according to any aspect of the present invention, may be genetically modified to comprise increased expression relative to the wild type cell of at least enzymes $E_1$ and $E_2$. In another example, the recombinant cell according to any aspect of the present invention, may be genetically modified to comprise increased activity relative to the wild type cell of at least enzymes $E_1$ and $E_2$. This increase in activity of the enzymes $E_1$ and $E_2$ may be a result of mutations in the enzymes found in the cell that result in enzymes $E_1$ and $E_2$ being more effective in catalysing specific reactions in the cells.

A skilled person would be able to use any method known in the art to genetically modify a cell or microorganism. According to any aspect of the present invention, the genetically modified cell may be genetically modified so that in a defined time interval, within 2 hours, in particular within 8 hours or 24 hours, it forms at least once or twice, especially at least 10 times, at least 100 times, at least 1000 times or at least 10000 times more N-acetyl homoserine and derivatives thereof than the wild-type cell.

The increase in product formation can be determined for example by cultivating the cell according to any aspect of the present invention and the wild-type cell each separately under the same conditions (same cell density, same nutrient medium, same culture conditions) for a specified time interval in a suitable nutrient medium and then determining the amount of target product N-acetyl homoserine and derivatives thereof) in the nutrient medium.

The genetically modified cell or microorganism may be genetically different from the wild type cell or microorganism. The genetic difference between the genetically modified microorganism according to any aspect of the present invention and the wild type microorganism may be in the presence of a complete gene, amino acid, nucleotide etc. in the genetically modified microorganism that may be absent in the wild type microorganism. In one example, the genetically modified microorganism according to any aspect of the present invention may comprise enzymes that enable the microorganism to produce N-acetyl homoserine and derivatives thereof compared to the wild type cells. The wild type microorganism relative to the genetically modified microorganism of the present invention may have none or no detectable activity of the enzymes that enable the genetically modified microorganism to produce N-acetyl homoserine and derivatives thereof. As used herein, the term 'genetically modified microorganism' may be used interchangeably with the term 'genetically modified cell'. The genetic modification according to any aspect of the present invention is carried out on the cell of the microorganism.

The cells according to any aspect of the present invention are genetically transformed according to any method known in the art.

The phrase 'the genetically modified cell has an increased activity, in comparison with its wild type, in enzymes' as used herein refers to the activity of the respective enzyme that is increased by a factor of at least 2, in particular of at least 10, more in particular of at least 100, yet more in particular of at least 1000 and even more in particular of at least 10000.

The phrase "increased activity of an enzyme", as used herein is to be understood as increased intracellular activity. Basically, an increase in enzymatic activity can be achieved by by selective mutation resulting in an amino acid exchange which results in increased specific activity or in an enzyme with alleviated inhibition or feedback inhibition by certain metabolites, increasing the copy number of the gene sequence or gene sequences that code for the enzyme, using a strong promoter or employing a gene or allele that codes for a corresponding enzyme with increased activity, altering the codon utilization of the gene, increasing the half-life of the mRNA or of the enzyme in various ways, modifying the regulation of the expression of the gene and optionally by combining these measures. Genetically modified cells used according to any aspect of the present invention are for example produced by transformation, transduction, conjugation or a combination of these methods with a vector that contains the desired gene, an allele of this gene or parts thereof and a vector that makes expression of the gene possible. Heterologous expression is in particular achieved by integration of the gene or of the alleles in the chromosome of the cell or an extrachromosomally replicating vector In the same context, the phrase "decreased activity of an enzyme Ex" used with reference to any aspect of the present invention may be understood as meaning an activity decreased by a factor of at least 0.5, particularly of at least 0.1, more particularly of at least 0.01, even more particularly of at least 0.001 and most particularly of at least 0.0001. The phrase "decreased activity" also comprises no detectable activity ("activity of zero"). The decrease in the activity of a certain enzyme can be effected, for example, by selective mutation or by other measures known to the person skilled in the art for decreasing the activity of a certain enzyme. In particular, the person skilled in the art finds instructions for the modification and decrease of protein expression and concomitant lowering of enzyme activity by means of interrupting specific genes, for example at least in Dubeau et al. 2009. Singh & ROhm. 2008., Lee et al., 2009 and the like. The decrease in the enzymatic activity in a cell according to any aspect of the present invention may be achieved by modification of a gene comprising one of the nucleic acid sequences, wherein the modification is selected from the group comprising, consisting of, insertion of foreign DNA in the gene, deletion of at least parts of the gene, point mutations in the gene sequence, RNA interference (siRNA), antisense RNA or modification (insertion, deletion or point mutations) of regulatory sequences, such as, for example, promoters and terminators or of ribosome binding sites, which flank the gene. To achieve a decrease in expression of a target gene, for example, expression of the gene or the catalytic properties of the enzyme proteins can be reduced or eliminated. The two measures can optionally be combined.

Foreign DNA is to be understood in this connection as meaning any DNA sequence which is "foreign" to the gene (and not to the organism), i.e. endogenous DNA sequences can also function in this connection as "foreign DNA". In this connection, it is particularly preferred that the gene is interrupted by insertion of a selection marker gene, thus the foreign DNA is a selection marker gene, wherein preferably the insertion was effected by homologous recombination in the gene locus.

The cell according to any aspect of the present invention may have increased expression of $E_2$ that may enable increase in production of methionine precursor. The enzyme $E_2$ may be homoserine O-acetyltransferase (metA and/or metX). In particular, the enzyme $E_2$ may be capable of producing at least one methionine precursor, for example N-acetylhomoserine and/or derivatives thereof in the presence of acetyl-CoA. In one example, the cell according to any aspect of the present invention may be modified to knock-out authentic or endogenous metA and/or metX genes involved in the synthesis of methionine precursor in the cells and introduce foreign or exogenous metX gene and/or metA gene free from a feed-back system. The metA, metB, metC, and metE or metH gene involved in the methionine synthesis is repressed by feed-back regulation system. Expressing foreign metA and/or metX gene in the cell according to any aspect of the present invention thus enables the expression of this gene (metA and/or metX) independent of the feed-back regulation system. This may thus increase the expression of enzyme $E_2$ relative to the wild type cell thus increasing the production of N-acetylhomoserine and/or derivatives thereof.

In one example, to allow the cell to have an increase in expression of enzyme $E_2$, the transcription regulator of methionine synthetic pathway may be deleted or weakened. In particular, metJ gene, a typical transcriptor regulator gene in *E. coli*, may be eliminated in the cell where the expression of metA and/or metX gene may be increased. In this example where metJ gene is eliminated and the metA and/or metX gene is overexpressed, methionine precursor expression may also increase.

In a further example, the gene in itself of rnetX and/or metA which encode homoserine O-acetyltransferase may be introduced into the cell by basic methods of genetic modification known in the art to increase synthesis of N-acetyl-homoserine or derivatives thereof, methionine precursor.

In one example, the enzyme $E_2$ may be metA. Homoserine O-acetyltransferase in some specific microorganisms may be designated metA. In particular, the enzyme $E_2$ may be metA from *Methanosarcina acetivorans*.

The metX is a common designation of gene encoding the protein having activity of homoserine O-acetyltransferase. MetX may be obtained from various microorganism species. For example, the homoserine O-acetyltransferase peptide may be encoded by the genes from *Corynebacterium* sp., *Leptospira* sp., *Deinococcus* sp., *Pseudomonas* sp., or *Mycobacterium* sp. In particular, the enzyme $E_2$, homoserine O-acetyltransferase peptide may be encoded by the genes derived from *Corynebacterium giutamicum, Leptospira meyeri, Deinococcus radiodurans, Pseudomonas aeruginosa*, or *Mycobacterium smegmatis*. More in particular, the enzyme $E_2$ may be homoserine O-acetyltransferase from *Corynebacterium glutamicum* ATCC13032 or variants thereof. Even more in particular, the enzyme $E_2$ comprises amino acid sequence SEQ ID NO: 1 or variant thereof.

Any method known in the art may be used to introduce and/or enhance the expression of metX and/or metA in the cell according to any aspect of the present invention. In one example, introduction of the gene in the cell by recombinant methods may be used. In particular, the expression of enzyme $E_2$ may be increased in the recombinant cell by introduction of SEQ ID NO:2 or variant thereof. In another example, modification of a promoter region of the gene and the nucleotide sequence of 5'-UTR or by introducing the mutation in the ORF region of the target gene may be carried out. A combination of any of these methods may be carried out to increase and/or enhance the expression of enzyme $E_2$ in the cell. The enhancement of metX gene expression may result in the increase of methionine precursor synthesis. In particular, the enhancement of metX gene expression may result in the increase of N-acetylhomoserine and/or derivatives thereof synthesis.

The cell according to any aspect of the present invention may also comprise an increased activity relative to a wild type cell of (a) an enzyme $E_1$, a homoserine dehydrogenase (1.1.1.3). The increase in activity of enzyme $E_1$ may increase synthesis of homoserine which is the precursor of N-acetyl homoserine and/or derivatives thereof. $E_1$ may be bifunctional asparokinase/homroserine dehydrogenase 1. In one example, the increase in activity of enzyme $E_1$ may be a result of at least one point mutation in homoserine dehydrogenase ($E_1$) and/or aspartokinase ($E_5$). In particular, the enzyme $E_1$ may be thrA gene that comprises an amino acid sequence of SEQ ID NO:3 that comprises a mutation at amino acid position 345 (Ser345Phe) compared to the wild type protein encoded by the gene from Uniprot database No: P00561. More in particular, the gene encoding enzyme $E_1$ has a point mutation at base pair position 1034 where C is replaced by T to encode peptide with SEQ ID NO:3. Even more in particular, the nucleotide sequence encoding enzyme $E_1$ comprises SEQ ID NO:5. The mutated enzyme $E_1$ may be referred to as 'mutated $E_1$' herein.

In another example, the enzyme $E_5$ may be an aspartokinase. In particular, the enzyme $E_5$ may be lysC gene that comprises an amino acid sequence of SEQ ID NO:4 that comprises a mutation at amino acid position 342 (Thr342Ile) compared to the wild type protein encoded by the gene from Uniprot database No:P08660. More in particular, the gene encoding enzyme $E_5$ has a point mutation at base pair position 1055 where C is replaced by T to encode peptide with SEQ ID NO:4. Even more in particular, the nucleotide sequence encoding enzyme $E_5$ comprises SEQ ID NO:6. The mutated enzyme $E_5$ may be referred to as 'mutated $E_5$' herein. Enhancement of the thrA and/or lysC activity may be performed by introducing the mutation in the thrA gene and/or lysC or by further introducing the target gene on the chromosome or by further introducing processed plasmid. In particular, the activity of enzymes $E_1$ and/or $E_5$ may be increased in the recombinant cell by introduction of SEQ ID NO:5 and SEQ ID NO:6 respectively.

In a further example, the increase in activity of enzyme $E_1$ may be brought about by a point mutation in enzyme $E_1$ and/or a point mutation in enzyme $E_5$, wherein the enzymes $E_1$ and $E_5$ may be expressed naturally (i.e. without the specific mutations) in the wild type cell. The point mutation in enzyme $E_1$ may prevent feedback inhibition by threonine. The point mutation in enzyme $E_5$ may prevent feedback inhibition by lysine. In one example, the cell may express only mutated $E_1$. In another example, the cell may express only mutated $E_5$. In a further example, the cell may express both the mutated $E_1$ and $E_5$. The increase in activity of $E_1$ may thus be brought about by the mutations of $E_1$ and/or $E_5$.

In one example, the cell used according to any aspect of the present invention may not express $E_1$ and $E_5$ in the wild type cell. The mutated $E_1$ and/or $E_5$ may have to be introduced into the cell to bring about the increase in activity of $E_1$.

The recombinant cell according to any aspect of the present invention may comprise increased activity of enzymes $E_1$, $E_5$ and $E_2$ relative to the wild type cell.

The teachings of the present invention may not only be carried out using biological macromolecules having the exact amino acid or nucleic acid sequences referred to in this application explicitly, for example by name or accession number, or implicitly, but also using variants of such sequences. The term "variant", as used herein, comprises amino acid or nucleic acid sequences, respectively, that are at least 70, 75, 80, 85, 90, 92, 94, 95, 96, 97, 98 or 99% identical to the reference amino acid or nucleic acid sequence, wherein preferably amino acids other than those essential for the function, for example the catalytic activity of a protein, or the fold or structure of a molecule are deleted, substituted or replaced by insertions or essential amino acids are replaced in a conservative manner to the effect that the biological activity of the reference sequence or a molecule derived therefrom is preserved. The state of the art comprises algorithms that may be used to align two given nucleic acid or amino acid sequences and to calculate the degree of identity, see Arthur Lesk (2008), Thompson et al., 1994, and Katoh et al., 2005. The term "variant" is used synonymously and interchangeably with the term "homologue". Such variants may be prepared by introducing deletions, insertions or substitutions in amino acid or nucleic acid sequences as well as fusions comprising such macromolecules or variants thereof. In one example, the term "variant", with regard to amino acid sequence, comprises, in addition to the above sequence identity, amino acid sequences that comprise one or more conservative amino acid changes with respect to the respective reference or wild type sequence or comprises nucleic acid sequences encoding amino acid sequences that comprise one or more conservative amino acid changes. In one example, the term "variant" of an amino acid sequence or nucleic acid sequence comprises, in addition to the above degree of sequence identity, any active portion and/or fragment of the amino acid sequence or nucleic acid sequence, respectively, or any nucleic acid sequence encoding an active portion and/or fragment of an amino acid sequence. The term "active portion", as used herein, refers to an amino acid sequence or a nucleic acid sequence, which is less than the full length amino acid sequence or codes for less than the full length amino acid sequence, respectively, wherein the amino acid sequence or the amino acid sequence encoded, respectively retains at least some of its essential biological activity. For example an active portion and/or fragment of a protease may be capable of hydrolysing peptide bonds in polypeptides. The phrase "retains at least some of its essential biological activity", as used herein, means that the amino acid sequence in question has a biological activity exceeding and distinct from the background activity and the kinetic parameters characterising said activity, more specifically $k_{cat}$ and $K_M$, are preferably within 3, 2, or 1 order of magnitude of the values displayed by the reference molecule with respect to a specific substrate. Similarly, the term "variant" of a nucleic acid comprises nucleic acids the complementary strand of which hybridises, preferably under stringent conditions, to the reference or wild type nucleic acid. A skilled person would be able to easily determine the sequences of enzymes that will be capable of carrying out the functions as disclosed.

Stringency of hybridisation reactions is readily determinable by one ordinary skilled in the art, and generally is an empirical calculation dependent on probe length, washing temperature and salt concentration. In general, longer probes require higher temperatures for proper annealing, while shorter probes need lower temperatures. Hybridisation generally depends on the ability of denatured DNA to reanneal to complementary strands when present in an environment below their melting temperature. The higher the degree of desired homology between the probe and hybridisable sequence, the higher the relative temperature which may be used. As a result it follows that higher relative temperatures would tend to make the reaction conditions more stringent, while lower temperature less so. For additional details and explanation of stringency of hybridisation reactions, see F. M. Ausubel (1995). The person skilled in the art may follow the instructions given in the manual "The DIG System Users Guide for Filter Hybridization", Boehringer Mannheim GmbH, Mannheim, Germany, 1993 and in Liebl et al., 1991 on how to identify DNA sequences by means of hybridisation. In one example, stringent conditions are applied for any hybridisation, i.e. hybridisation occurs only if the probe is 70% or more identical to the target sequence. Probes having a lower degree of identity with respect to the target sequence may hybridise, but such hybrids are unstable and will be removed in a washing step under stringent conditions, for example by lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC.

Polynucleotide fragments having a degree of identity with respect to the reference or wild type sequence of at least 70, 80, 90, 91, 92, 93, 94, 95, 96, 97, 98, 99% may be isolated. The term "homologue" of a nucleic acid sequence, as used herein, refers to any nucleic acid sequence that encodes the same amino acid sequence as the reference nucleic acid sequence, in line with the degeneracy of the genetic code.

The cell according to any aspect of the present invention may be selected from a wide range of microbial cells. In particular, the cell may be a prokaryotic or a lower eukaryotic cell. In one example the cell is selected from the group consisting of *Acinetobacter* sp., *Bacillus* sp., *Brevibacterium* sp., *Burkholderia* sp., *Chlorella* sp., *Corynebacterium* sp., *Cyanobacterien, Erwinia* sp., *Escherichia* sp., *Klebsiella* sp., *Serratia* sp., *Providencia* sp., *Pseudomonas* sp., *Rhizobium* sp. *Salmonella* sp., and *Nostoc* sp. The cell may be selected from the group consisting of *Corynebacterium glutamicum* and *E. coli*. In one example, the cell may be *Escherichia coli*. In another example, the cell may be *Corynebacterium glutamicum*. In yet another example, the cell may be a lower eukaryote, such as a fungus from the group comprising *Saccharomyces, Candida, Pichia, Schizosaccharomyces* and *Yarrowia*, particularly, *Saccharomyces cerevisiae*. The cell may be an isolated cell, in other words a pure culture of a single strain, or may comprise a mixture of at least two strains. Biotechnologically relevant cells are commercially available, for example from the American Type Culture Collection (ATCC) or the German Collection of Microorganisms and Cell Cultures (DSMZ). Particles for keeping and modifying cells are available from the prior art, for example Sambrook/Fritsch/Maniatis (1989).

In one example, the recombinant cell further comprises a decreased expression relative to the wild type cell of:
(a) an enzyme $E_3$, an diaminopimelate decarboxylase (EC4.1.1.20); and
(b) an enzyme $E_4$, a homoserine O-transsuccinylase (EC2.3.1.46).

In particular, the activity of enzymes $E_3$ and $E_4$ may be reduced or inhibited by methods known in the art. In one example, enzyme $E_3$ may comprise amino acid sequence SEQ ID NO:7. This enzyme may be inactivated by deleting a base pair from the wild type sequence in the recombinant cell according to any aspect of the present invention. In one example, the inactive $E_3$ is encoded by gene lysA with SEQ ID NO:8 that has deletion of bp 4 to 1239 of the wild type lysA sequence.

In another example, the enzyme $E_4$ also referred to as homoserine O-succinyl transferase may comprise amino acid sequence SEQ ID NO:9. This enzyme may be inactivated by deleting a base pair from the wild type sequence in the recombinant cell according to any aspect of the present invention. In one example, the inactive $E_4$ is encoded by gene metA with SEQ ID NO:10 that has deletion of bp 4 to 909 of the wild type metA sequence. The metA referred to as enzyme $E_4$ is distinct from the metA referred to as enzyme $E_2$. A skilled person would understand that although they share the same gene nomenclature (i.e. MetA), they have different functions and unique EC classification numbers. The MetA that falls within the definition of enzyme $E_2$ according to any aspect of the present invention has EC2.3.1.31. The MetA that falls within the definition of enzyme $E_4$ according to any aspect of the present invention has EC2.3.1.46. Inactivation of $E_4$ particularly allows for enzyme $E_2$ to carry out its function without any interference from the feedback regulated system found in a wild type cell.

In a further example, the cell according to any aspect of the present invention comprises an increased activity relative to a wild type cell of enzymes $E_1$ (mutated $E_1$), $E_5$ (mutated $E_5$) and $E_2$ and a decreased expression relative to a wild type cell of enzymes $E_3$ and $E_4$. In one example, the cell according to any aspect of the present invention comprises an increased activity relative to a wild type cell of enzymes $E_1$ (mutated $E_1$) and $E_2$ and a decreased expression relative to a wild type cell of enzymes $E_3$ and $E_4$. In yet another example, the cell according to any aspect of the present invention comprises an increased expression relative to a wild type cell of enzymes $E_5$ (mutated $E_5$) and $E_2$ and a decreased expression relative to a wild type cell of enzymes $E_3$ and $E_4$.

The N-acetyl homoserine and/or derivatives thereof may be have an L or D stereochemistry. In particular, N-acetyl homoserine and/or derivatives thereof may be selected from the group consisting of O-acetyl-N-acetamido-L-homoserine, O-acetyl-N-acetamido-D-homoserine, N-acetamido-L-homoserine and N-acetamido-D-homoserine.

The term "contacting", as used herein, means bringing about direct contact between the cell according to any aspect of the present invention and the medium comprising the carbon source in the method according to any aspect of the present invention. The contact may be a direct contact between the cell and the aqueous medium with the carbon source. In one example, the cell, and the medium comprising the carbon source may be in different compartments. In particular, the carbon source may be in a gaseous state and added to the medium comprising the cells according to any aspect of the present invention.

The term "an aqueous solution" or "medium" comprises any solution comprising water, mainly water as solvent that may be used to keep the cell according to any aspect of the present invention, at least temporarily, in a metabolically active and/or viable state and comprises, if such is necessary, any additional substrates. The person skilled in the art is familiar with the preparation of numerous aqueous solutions, usually referred to as media that may be used to keep the cells according to any aspect of the present invention, for example LB medium in the case of *E. coli*, and/or *Corynebacterium glutamicum*. It is advantageous to use as an aqueous solution a minimal medium, i.e. a medium of reasonably simple composition that comprises only the minimal set of salts and nutrients indispensable for keeping the cell in a metabolically active and/or viable state, by contrast to complex mediums, to avoid dispensable contamination of the products with unwanted side products. For example, M9 medium may be used as a minimal medium. The cells are incubated with the carbon source sufficiently long enough to produce the desired product, N-acetyl homoserine and/or derivatives thereof and variants thereof. For example for at least 1, 2, 4, 5, 10 or 20 hours. The temperature chosen must be such that the cells according to any aspect of the present invention remains catalytically competent and/or metabolically active, for example 10 to 42° C., preferably 30 to 40° C., in particular, 32 to 38° C. in case the cell is a *E. coli* or *Corynebacterium glutamicum*.

A skilled person would understand the other conditions necessary to carry out the method according to any aspect of the present invention. In particular, the conditions in the container (e.g. fermenter) may be varied depending on the first, second and third microorganisms used. The varying of the conditions to be suitable for the optimal functioning of the microorganisms is within the knowledge of a skilled person.

In one example, the method according to any aspect of the present invention may be carried out in an aqueous medium with a pH between 5 and 8, 5.5 and 7. The pressure may be between 1 and 10 bar. According to another aspect of the present invention, there is provided a use of at least one recombinant cell to produce N-acetyl homoserine and/or derivatives thereof from a carbon source, wherein the recombinant cell comprises an increasedactivity relative to a wild type cell of
(a) an enzyme $E_1$, homoserine dehydrogenase (EC1.1.1.3) and/or an enzyme $E_5$, an aspartokinase (EC2.7.2.4); and (b) an enzyme $E_2$, a homoserine O-acetyl transferase (EC2.3.1.31).

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

Formation of O-acetyl-N-acetamido-DL-homoserine from acetic acid with *Escherichia coli* For the biotransformation of acetate to O-acetyl-N-acetamido-DL-homoserine the genetically modified strain *Escherichia coli* W3110 ΔlysA lysCfbr thrAfbr ΔmetA pCDF{Ptac}[thrA_fbrEc]{Placuv5}[metX_Cg] was used. This strain harbours the following characteristics:
  i. Deletion of the *E. coli* W3110 lysA gene (SEQ ID NO: 8), encoding diaminopimelate decarboxylase
  ii. Deletion of the *E. coli* W3110 metA gene (SEQ ID NO: 10), encoding homoserine O-transsuccinylase
  iii. Expression of an allele of *E. coli* W3110 lysC gene (SEQ ID NO: 6), encoding a feedback-resistant variant of aspartokinase 3
  iv. Expression of an allele of *E. coli* W3110 thrA gene (SEQ ID NO: 5), encoding a feedback-resistant variant of bifunctional aspartokinase 1/homoserine dehydrogenase 1
  v. Expression of the *C. glutamicum* ATCC 13032 metX-gene (SEQ ID NO: 2), encoding homoserine O-acetyl transferase.

These characteristics were brought about by:
  i. Inactivation of the *E. coli* W3110 lysA gene (deletion of bp 4 to 1239) with pKO3 derivative HM-p-6 (SEQ ID NO: 12)
  ii. Inactivation of the *E. coli* W3110 metA gene (deletion of bp 4 to 909) with pKO3 derivative pGR-3-46 (SEQ ID NO: 13)
  iii. Replacement of *E. coli* W3110 lysC gene by another allele of lysC, encoding a feedbackresistant variant of lysC (point mutation at bp 1055 from C to T, Thr342Ile, SEQ ID NO:6) with pKO3 derivative pJAG-4-47 (SEQ ID NO: 14)
  iv. Replacement of *E. coli* W3110 thrA gene by another allele of thrA, encoding a feedbackresistant variant of thrA (point mutation at bp 1034 from C to T, Ser345Phe, SEQ ID NO: 5) with pKO3 derivative 4-49 (SEQ ID NO: 15)
  v. Introduction of plasmid pCDF{Ptac}[thrA_fbr_Ec]{Placuv5}[metX_Cg] (SEQ ID: 11)

For construction of pKO3 derivates for gene deletion and allelic replacement homologous sequences up- and downstream of the target genes were amplified by PCR from genomic DNA of *Escherichia coli* W3110 using the following primers. Homologue ends for assembly cloning were introduced within the primers.

| | metA homologue sequence 1 | |
|---|---|---|
| metA_up_fp | CTGGTCTCGGTACCCGGGGATCGCG GCCGCCCAACCGCCTGCTCATTTTG | SEQ ID No. 16 |

| | | |
|---|---|---|
| metA_up_rp | GCGTTGGATTCACCTCGAGCATAACCTGATTACCTCACTACATAC | SEQ ID No. 17 |
| metA_down_fp | metA homologue sequence 2 TATGCTCGAGGTGAATCCAACGCTGGATTAATCTTC | SEQ ID No. 18 |
| metA_up_rp | CGCCACCGGTCGACTCTAGAGGATCGCGGCCGCAATCAGCATCGCGAATGGAAG | SEQ ID No. 19 |
| MW_15_62_fw | lysA homologue sequence 1 TCTCGGTACCCGGGGATCGCTTTAAGCTGACATCGGGATAAC | SEQ ID No. 20 |
| MW_15_63_rv | CATAACAAACTCCAGATAAGTGCTTTTTTATG | SEQ ID No. 21 |
| MW_15_64_fw | lysA homologue sequence 2 CTTATCTGGAGTTTGTTATGCTCGAGGAATTGCTTTAACTGCGGTTAGTC | SEQ ID No. 22 |
| MW_15_65_rv | GGTCGACTCTAGAGGATCGCATACCCGCATTGGTTATCTGTG | SEQ ID No. 23 |
| MW_15_66_fw | lysCfbr homologue sequence 1 TCTCGGTACCCGGGGATCGCTCACCCAGGGATTTATCGGTAG | SEQ ID No. 24 |
| MW_15_67_rv | CAAGGATTAATGCCACGCTCAC | SEQ ID No. 25 |
| MW_15_68_fw | lysCfbr homologue sequence 2 GTGAGCGTGGCATTAATCCTTG | SEQ ID No. 26 |
| MW_15_69_rv | GGTCGACTCTAGAGGATCGCGGAATTCGTTTGCGAGCAGAAC | SEQ ID No. 27 |
| JC-15-009_fw | thrAfbr homologue sequence 1 GCTGGTCTCGGTACCCGGGGATCGCCATTCCGGCTGATCACATGG | SEQ ID No. 28 |
| JC-15-006_rv | GTAATCAGCACCACGAAAATACGGG | SEQ ID No. 29 |
| JC-15-007_fw | thrAfbr homologue sequence 2 CCCGTATTTTCGTGGTGCTGATTAC | SEQ ID No. 30 |
| JC-15-010_rv | CCACCGGTCGACTCTAGAGGATCGCTTGCGCCAGTTCTTCCTGCC | SEQ ID No. 31 |

The PCR was performed with the Phusion® High-Fidelity Master Mix according to the manufacturer (New England Biolabs, Ipswich, Mass., USA). The thermal cycle profile was 3 min at 98° C. for initial denaturation, 35 cycles: 10 sec at 98° C., 30 sec at 60° C. to 68° C. (gradient), 20 sec at 72° C. and a final 10 min hold step at 72° C. Purification of PCR products was performed by gel extraction or PCR purification according to the manufacturer of purification kits (Qia-Quick PCR Purification Kit and QiaQuick Gel extraction Kit; Qiagen, Hilden, Germany). Purified PCR products were assembled into NotI restricted pKO3 plasmid using the NEBuilder® HiFi DNA Assembly Master Mix according to the manufacturers manual (New England Biolabs, Ipswich Mass., USA). Transformation of *E. coli* DH10β was performed according to the manufacturer of competent cells (NEB 10-beta electrocompetent *E. coli*, New England Biolabs, Ipswich Mass., USA). The final plasmids were verified by restriction analysis and DNA sequencing.

For construction of an *E. coli* expression vector for thrA, encoding a feedbackresistant variant of the aspartate kinase thrA from *Escherichia coli* W3110 and metX, encoding a homoserine acetyl transferase from *Corynebacterium glutamicum* ATCC13032, both genes were amplified by PCR from genomic DNA of the donor organism. The point mutation of thrA that lead to a feedbackresistant variant was implemented within the forward primer. The gene thrA was cloned downstream of a tac-promoter (SEQ ID NO. 32) which was also amplified by PCR from another vector. Following primers were used for amplification.

| | | |
|---|---|---|
| JC-15-001 | metX_Cg GGATCTAGGAACCAAGGAGAGTGGCATGCCCACCCTCGCGCCTTC | SEQ ID NO. 33 |
| JC-15-002 | CAATTGGATCCGTTTATCCGGAGGGTTGCCTGTG | SEQ ID NO. 34 |
| JC-15-003 | Ptac ACCCTCCGGATAAACGGATCCAATTGTGAGCGGATAAC | SEQ ID NO. 35 |
| JC-15-004 | ACACTCGCATATGTTTTACCTCCTGTTAAAC | SEQ ID NO. 36 |
| JC-15-005 | thrA part 1 CAGGAGGTAAAACATATGCGAGTGTTGAAGTTCGG | SEQ ID NO. 37 |
| JC-15-006 | GTAATCAGCACCACGAAAATACGGG | SEQ ID NO. 38 |
| JC-15-007 | thrA part 2 CCCGTATTTTCGTGGTGCTGATTAC | SEQ ID NO. 39 |
| JC-15-008 | GGTGCGCCAGGAGAGTTGTTGATTTATCAGACTCCTAACTTCCATGAGAG | SEQ ID NO. 40 |

PCR was performed with the Phusion® High-Fidelity Master Mix according to the manufacturer (New England Biolabs, Ipswich, Mass., USA). The thermal cycle profile was 3 min at 98° C. for initial denaturation, 35 cycles: 10 sec at 98° C., 30 sec at 60° C. to 70° C. (gradient), 45 sec at 72° C. and a final 10 min hold step at 72° C. Purification of PCR products was performed by gel extraction or PCR purification according to the manufacturer of purification kits (Qia-Quick PCR Purification Kit and QiaQuick Gel extraction Kit; Qiagen, Hilden, Germany). Purified PCR products were assembled into NdeI and XbaI restricted high copy vector pJ281_Placuv5 (SEQ ID NO. 41) using the NEBuilder® HiFi DNA Assembly Master Mix according to the manufacturers manual (New England Biolabs, Ipswich Mass., USA). Transformation of *E. coli* DH1013 was performed according to the manufacturer of competent cells (Electro-MAX DH10B, Thermo Fisher Scientific, Waltham, Mass., USA). The final plasmid pJAG-4-48 (SEQ ID NO.42) was verified by restriction analysis and DNA sequencing. Further the genes thrA and metX were subcloned into a NdeI and XhoI restricted pCDF derivate (pCDF_Ptac; SEQ ID NO. 43), which already contains a tac promoter sequence. For subcloning the target genes were amplified by PCR using the following primers with homologous sequences for assembly cloning.

| | thrA | |
|---|---|---|
| thrAfbr_fw | GTTTAACAGGAGGTAAAACATATGC | SEQ ID NO. 44 |
| thrAfbr_rev | GCTCACTGCCTTATCAGACTCCTAACTTCCATG | SEQ ID NO. 45 |
| | Placuv5-metX | |
| Placuv5_fw | AGTCTGATAAGGCAGTGAGCGCAACGCAATTAATG | SEQ ID NO. 46 |
| metX_rev | CAGCGGTTTCTTTACCAGACCTATTAGATGTAGAACTCGATGTAGGTC | SEQ ID NO. 47 |

PCR was performed with the Phusion® High-Fidelity Master Mix according to the manufacturer (New England Biolabs, Ipswich, Mass., USA). The thermal cycle profile was 3 min at 98° C. for initial denaturation, 35 cycles: 10 sec at 98° C., 20 sec at 60° C. to 68° C. (gradient), 45 sec at 72° C. and a final 10 min hold step at 72° C. Purification of PCR products was performed by gel extraction according to the manufacturer of the purification kit (QiaQuick Gel extraction Kit; Qiagen, Hilden, Germany).

Purified PCR products were assembled into NdeI and XhoI restricted vector pCDF_Ptac (SEQ ID NO) using the NEBuilder® HiFi DNA Assembly Master Mix according to the manufacturers manual (New England Biolabs, Ipswich Mass., USA). Transformation of *E. coli* DH1013 was performed according to the manufacturer of competent cells (NEB 10-beta electrocompetent *E. coli*, New England Biolabs, Ipswich Mass., USA). The final plasmid pJAG-4-50 (SEQ ID NO. 48) was verified by restriction analysis and DNA sequencing.

Gene deletion and allelic replacement was performed by using plasmid pKO3 and methods described previously (Link A J, Phillips D, Church G M. Methods for generating precise deletions and insertions in the genome of wild-type *Escherichia coli*: application to open reading frame characterization. J Bacteriol. 179(20):6228-37). Transformation of *E. coli* W3110 was performed via electroporation as known in the art.

*E. coli* was cultivated on LB agar plates (15 g/L agar, 5 g/L yeast extract, 10 g/L tryptone, 10 g/L NaCl, pH 7.0, with additional 100 mg/L spectinomycine sulfate) for 24 h at 37° C.

For the first preculture 3×5 ml of LB medium (5 g/L yeast extract, 10 g/L tryptone, 10 g/L NaCl, pH 7.0, with additional 100 mg/L spectinomycine sulfate) in a 100 ml shaking flask were inoculated with a single colony from a fresh incubated agar plate and cultivated at 37° C. and 200 rpm for 7 h to an $OD_{600nm}$>3.0.

For the second preculture 8×50 ml of M9 medium (pH 7.40, $Na_2HPO_4$×12 $H_2O$ 13.68 g/L, $KH_2PO_4$ 3.00 g/L, NaCl 0.50 g/L, $NH_4Cl$ 2.00 g/L, $NH_4$acetate 5.00 g/L, $MgSO_4$×7$H_2O$ 0.49 g/L, HCl (25%) 0.13 ml/L, $MnCl_2$×7 $H_2O$ 1.91 mg/L, $ZnSO_4$×7 $H_2O$ 1.87 mg/L, Na-EDTA×2$H_2O$ 0.84 mg/L, $H_3BO_3$ 0.30 mg/L, $Na_2MoO_4$×2 $H_2O$ 0.25 mg/L, $CaCl_2$×2 $H_2O$ 4.70 mg/L, $FeSO_4$×7 $H_2O$ 17.80 mg/L, $CuCl_2$×2 $H_2O$ 0.15 mg/L, with additional 100 mg/L spectinomycine sulfate, 3 mM methionine and 3 mM lysine) in a 500 ml shaking flask were inoculated with 0.5 ml cell suspension each from the pooled first precultures and cultivated at 37° C. and 200 rpm for 18 h to an $OD_{600nm}$>1.5.

Then the cell suspension was centrifuged, washed with fresh M9 medium and centrifuged again. For the main culture 200 ml of fresh M9 medium (without methionine and lysine) in a 500 mL glass bottle were inoculated with centrifuged and washed cells from the preculture to an $OD_{600nm}$ of 1.0. The cultivation was carried out in a pressure-resistant glass bottle that can be closed airtight with a butyl rubber stopper. The culture was incubated in an open water bath shaker at 30° C., 150 rpm and a ventilation rate of 4 L/h with synthetic air (79.5% $N_2$, 20.5% $O_2$) for 119 h. The air was discharged into the medium through a sparger with a pore size of 10 µm, which was mounted in the center of the reactors. The pH was hold at 7.3 by automatic addition of 25% acetic acid. After 4 h 1 mM IPTG was added for induction. At the start and during the culturing period, samples were taken. These were tested for optical density, pH and the different analytes (tested by NMR and LC-MS). HR-ESI-LCMS was measured on a Surveyor HPLC 1250 with LTQ-Orbitrap Elite equipped with 150×2 mm Accucore aq C18 (R138) column. Gradient elution was 0% B(3)-9-60% B-0.1-80% B(5) at 0.2 mL/min flow rate and 40° C. O-acetyl-N-acetamido-DL-homoserin was quantified relative to O-acetyl-L-homoserine.

During the cultivation phase the concentration of O-acetyl-L-homoserine increased from 0 to 180 mg/L and for N-acetyl-L-homoserine from 0 to 708 mg/L. 6.9 mg/L O-acetyl-N-acetamido-DL-homoserine were produced. During this time 8.7 g/L acetate was consumed.

Example 2

Formation of O-Acetyl-N-Acetamido-DL-Homoserine from Acetic Acid with *Corynebacterium glutamicum*

For the biotransformation of acetate to O-acetyl-N-acetamido-DL-homoserine the genetically modified strain *Corynebacterium glutamicum* MH20-22B hom_fbr pECXC99E-{Ptrc}[metX_Cg] was used. The strain *C. glutamicum* MH20-22B is a chemical mutant which is described by Schrumpf et al. (Appl Microbiol Biotechnol (1992) 37:566-571) and expresses a feedback-resistant aspartate kinase. The strain was modified by Sahm et al. (Ann N Y Acad Sci. 1996 May 15; 782:25-39) to strain *C. glutamicum* MH20-22B hom_fbr, which expresses additionally a feedback-resistant homoserine dehydrogenase. Additionally, this strain was transformed with the plasmid pECXC99E-{Ptrc}[metX_Cg] (SEQ ID NO. 49), which encodes for a homoserine O-acetyltransferase (MetX) from *Corynebacterium glutamicum* ATCC13032.

For construction of the *C. glutamicum* expression vector for metX, the gene was amplified by PCR from genomic DNA of the donor organism with the following primers.

| MW_15_50_fw | ATTCGAGCTCGGTACCCGGGATCCTAGTCTTGTCCACCCAGAACAG | SEQ ID NO. 50 |
|---|---|---|
| MW_15_51_rv | AACAGCCAAGCTTGCATGCCTGCAGTTGGTTTATCCGGAGGGTTG | SEQ ID NO. 51 |

The PCR was performed with the Phusion® High-Fidelity Master Mix according to the manufacturer (New England Biolabs, Ipswich, Mass., USA). The thermal cycle profile was 5 min at 98° C. for initial denaturation, 35 cycles: 10 sec at 98° C., 20 sec at 60° C., 39 sec at 72° C. and a final 10 min hold step at 72° C.

Purification of PCR products was performed by PCR purification according to the manufacturer of purification kit (QiaQuick PCR Purification Kit; Qiagen, Hilden, Germany). The purified PCR product was assembled into BamHI and PstI restricted vector pECXC99E (SEQ ID NO. 52) using the NEBuilder® HiFi DNA Assembly Master Mix according to the manufacturers manual (New England Biolabs, Ipswich Mass., USA). Transformation of *E. coli* DH1013 was performed according to the manufacturer of competent cells (NEB 10-beta; New England Biolabs, Ipswich, Mass., USA). The final plasmid pECXC99E-{Ptrc}[metX_Cg] (SEQ ID NO. 49) was verified by restriction analysis and DNA sequencing.

Transformation of *Corynebacterium glutamicum* ATCC13032 was performed as described previously, e.g. by van der Rest M E, Lange C, Molenaar D. A heat shock following electroporation induces highly efficient transformation of *Corynebacterium glutamicum* with xenogeneic plasmid DNA. Appl Microbiol Biotechnol. 1999. 52(4):541-5.

*Corynebacterium glutamicum* MH20-22B hom_fbr pECXC99E-{Ptrc}[metX_Cg] was cultivated on BHI agar plates (7.8 g/L brain extract, 2.0 g/L glucose, 2.0 g/L $Na_2HPO_4$, 9.7 g/L heart extract, 10.0 g/L pepton, 5.0 g/L NaCl, 15.0 g/L agar, pH 7.4, with additional 7.5 mg/L chloramphenicol) for 72 h at 30° C.

For the preculture 4×50 ml of LB medium (5 g/L yeast extract, 10 g/L tryptone, 10 g/L NaCl, pH 7.0, with additional 17.95 g/L potassium acetate and 7.5 mg/L chloramphenicol) in a 500 ml shaking flask were inoculated with a full loop of cells from a fresh incubated agar plate and cultivated at 30° C. and 120 rpm for 22 h to an $OD_{600nm}$>3.0. Then the cell suspension was centrifuged, washed with fresh CGF1 medium and centrifuged again.

For the main culture 200 ml of fresh CGF1 medium (pH=7.2, 2 g/L $(NH_4)_2SO_4$, 1 g/L $KH_2PO_4$, 1 g/L $K_2HPO_4$, 10 mg/L $FeSO_4×7\ H_2O$, 7.6 mg/L $MnSO_4×1\ H_2O$, 0.246 g/L $MgSO_4×7\ H_2O$, 10.8 g/L ammonium acetate, 0.1 g/L L-leucine, with additional 7.5 mg/L chloramphenicol) in a 500 mL glass bottle were inoculated with centrifuged and washed cells from the preculture to an $OD_{600nm}$ of 1.0. The cultivation was carried out in a pressure-resistant glass bottle that can be closed airtight with a butyl rubber stopper. The culture was incubated in an open water bath shaker at 30° C., 120 rpm and a ventilation rate of 4 L/h with synthetic air (79.5% $N_2$, 20.5% $O_2$) for 137 h. The air was discharged into the medium through a sparger with a pore size of 10 μm, which was mounted in the center of the reactors. The pH was hold at 7.2 by automatic addition of 25% acetic acid. After 21 h 1 mM IPTG was added for induction. At the start and during the culturing period, samples were taken. These were tested for optical density, pH and the different analytes (tested by NMR and LC-MS). HR-ESI-LCMS was measured on a Surveyor HPLC 1250 with LTQ-Orbitrap Elite equipped with 150×2 mm Accucore aq C18 (R138) column. Gradient elution was 0% B(3)-9-60% B-0.1-80% B(5) at 0.2 mL/min flow rate and 40° C. O-acetyl-N-acetamido-DL-homoserin was quantified relative to O-acetyl-L-homoserin. During the cultivation phase the concentration of O-acetyl-L-homoserine increased from 0 to 230 mg/L, for N-acetyl-L-homoserine from 0 to 306 mg/L, 8.3 mg/L O-acetyl-N-acetamido-DL-homoserine were produced. During this time 35.2 g/L acetate were consumed.

Example 3

No Formation of O-Acetyl-N-Acetamido-DL-Homoserine from Acetic Acid with *Corynebacterium glutamicum*

For the biotransformation of acetate to L-homoserine the genetically modified strain *Corynebacterium glutamicum* MH20-22B was used. The strain *C. glutamicum* MH20-22B is a chemical mutant which is described by Schrumpf et al. (Appl Microbiol Biotechnol (1992) 37:566-571) and expresses a feedback-resistant aspartate kinase. The strain was modified by Sahm et al. (Ann N Y Acad Sci. 1996 May 15; 782:25-39) to strain *C. glutamicum* MH20-22B hom_fbr, which expresses additionally a feedback-resistant homoserine dehydrogenase.

*Corynebacterium glutamicum* MH20-22B hom_fbr was cultivated on *Corynebacterium* agar plates (pH 7.3, 10 g/L caseine peptone tryptical digest, 5 g/L yeast extract, 5 g/L glucose, 5 g/L NaCl, 15 g/L agar) for 72 h at 30° C.

For the preculture 2×50 ml of CGS1 medium (pH 7.00, 10 g/L peptone, 5 g/L beef extract, 2.5 g/L NaCl, with additional 17.95 g/L potassium acetate) in a 500 ml shaking flask were inoculated with a full loop of cells from a fresh incubated agar plate and cultivated at 30° C. and 120 rpm for 28 h to an $OD_{600nm}$>1.0. After the cultivation the cell suspension was centrifuged, washed with fresh CGF1 medium (pH=7.2, 2 g/L $(NH_4)_2SO_4$, 1 g/L $KH_2PO_4$, 1 g/L $K_2HPO_4$, 10 mg/L $FeSO_4×7\ H_2O$, 7.6 mg/L $MnSO_4×1\ H_2O$, 0.246 g/L $MgSO_4×7\ H_2O$) and centrifuged again.

For the main culture 30 ml of fresh CGXmedium (pH=7.40, 20 g/L $(NH_4)_2SO_4$, 0.5 g/L $KH_2PO_4$, 0.5 g/L $K_2HPO_4$, 0.25 g/L $MgSO_4×7\ H_2O$, 10 mg/L $FeSO_4×7\ H_2O$, 10 mg/L $MnSO_4×H_2O$, 1 mg/L $ZnSO_4×7\ H_2O$, 0.3 mg/L $CuSO_4×5\ H_2O$, 0.037 mg/L $NiCl_2×6\ H_2O$, 0.2 mg/L biotin, 20 g/L $CaCO_3$, 40 g/L glucose, 0.05 g/L L-leucine) in a 250 mL shaking flask were inoculated with centrifuged and washed cells from the preculture to an $OD_{600nm}$ of 0.2. The culture was incubated at 30° C. and 150 rpm for 142 h. At the start and during the culturing period, samples were taken. These were tested for optical density, pH and the different analytes (tested by NMR).

During the cultivation phase the concentration L-homoserine increased from 0 to 535 mg/L, for L-lysine from 0 to 888 mg/L and for L-alanine from 0 to 350 mg/L. No O-Acetyl-L-homoserine, N-acetyl-L-homoserine or O-acetyl-N-acetamido-DL-homoserine were produced.

Example 4

No Formation of O-Acetyl-N-Acetamido-L-Homoserine from Glucose with *Escherichia coli*

For this example the genetically modified strain *Escherichia coli* W3110 ΔlysA lysCfbr thrAfbr ΔmetA was used. This strain harbours the following characteristics:

i. Deletion of the *E. coli* W3110 lysA gene (SEQ ID NO: 8), encoding diaminopimelate decarboxylase ii. Deletion of the *E. coli* W3110 metA gene (SEQ ID NO: 10), encoding homoserine O-transsuccinylase iii. Expression of an allele of *E. coli* W3110 lysC gene (SEQ ID NO: 6), encoding a feedback-resistant variant of aspartokinase 3 iv. Expression of an allele of *E. coli* W3110 thrA gene (SEQ ID NO: 5), encoding a feedback-resistant variant of bifunctional aspartokinase 1/homoserine dehydrogenase 1

These characteristics were brought about by:

i. Inactivation of the *E. coli* W3110 lysA gene (deletion of bp 4 to 1239) with pKO3 derivative HM-p-6 (SEQ ID NO: 12)

ii. Inactivation of the *E. coli* W3110 metA gene (deletion of bp 4 to 909) with pKO3 derivative pGR-3-46 (SEQ ID NO: 13)

iii. Replacement of *E. coli* W3110 lysC gene by another allele of lysC, encoding a feedbackresistant variant of lysC (point mutation at bp 1055 from C to T, Thr342Ile, SEQ ID NO:6) with pKO3 derivative pJAG-4-47 (SEQ ID NO: 14)

iv. Replacement of *E. coli* W3110 thrA gene by another allele of thrA, encoding a feedback resistant variant of thrA (point mutation at bp 1034 from C to T, Ser345Phe, SEQ ID NO: 5) with pKO3 derivative 4-49 (SEQ ID NO: 15)

Construction of pKO3 derivates were performed as described in Example 1.

Gene deletion and allelic replacement was performed by using plasmid pKO3 and methods described previously (Link A J, Phillips D, Church G M. Methods for generating precise deletions and insertions in the genome of wild-type *Escherichia coli*: application to open reading frame characterization. J Bacteriol. 179(20):6228-37). Transformation of *E. coli* W3110 was performed via electroporation as known in the art. *E. coli* was cultivated on LB agar plates (15 g/L agar, 5 g/L yeast extract, 10 g/L tryptone, 10 g/L NaCl, pH 7.0 for 24 h at 37° C.

5 ml of LB medium (5 g/L yeast extract, 10 g/L tryptone, 10 g/L NaCl, pH 7.0, in a culture tube were inoculated with a single colony from a fresh incubated agar plate and cultivated at 37° C. and 200 rpm for 6 h. 20 mL of M9-glucose medium (pH 7.40, $Na_2HPO_4 \times 12\ H_2O$ 13.68 g/L, $KH_2PO_4$ 3.00 g/L, NaCl 0.50 g/L, $NH_4Cl$ 2.00 g/L, glucose 20.00 g/L, $MgSO_4 \times 7H_2O$ 0.49 g/L, HCl (25%) 0.13 ml/L, $MnCl_2 \times 7\ H_2O$ 1.91 mg/L, $ZnSO_4 \times 7\ H_2O$ 1.87 mg/L, Na-EDTA$\times 2H_2O$ 0.84 mg/L, $H_3BO_3$ 0.30 mg/L, $Na_2MoO_4 \times 2\ H_2O$ 0.25 mg/L, $CaCl_2) \times 2H_2O$ 4.70 mg/L, $FeSO_4 \times 7\ H_2O$ 17.80 mg/L, $CuCl_2 \times 2\ H_2O$ 0.15 mg/L), with 3 mM methionine and 3 mM lysine in a 250 mL baffled shake flask were inoculated with 0.5 mL of the cell suspension. The culture was incubated at 37° C. and 200 rpm overnight to an $OD_{600nm}$ of 12.3. The cell suspension was used to inoculate 50 mL M9-glucose medium with 3 mM methionine and 3 mM lysine in a 250 ml baffled shaking flask to an $OD_{600nm}$ of 0.2. The culture was incubated at 30° C. and 200 rpm for 4.5 h to an $OD_{600nm}$ 1.39. IPTG was added to the culture to a concentration of 1 mM and the culture was incubated for 23.5 h at 30° C. and 200 rpm. Samples were taken throughout the 28 h cultivation and were analyzed by NMR.

Between 0 and 28 h of the cultivation no O-acetyl-L-homoserine and no O-acetyl-N-acetamido-L-homoserine was detected.

Example 5

Detection of O-acetyl-N-Acetamido-DL-Homoserine in a Fermentation Sample

*Escherichia coli* W3110 ΔlysA lysCfbr thrAfbr ΔmetA pCDF{Ptac}[thrA_fbr_Ec] {Placuv5}[metX_Cg] was cultivated on LB agar plates (15 g/L agar, 5 g/L yeast extract, 10 g/L tryptone, 10 g/L NaCl, pH 7.0, with additional 100 mg/L spectinomycine sulfate) for 24 h at 37° C.

For the first preculture 3×5 ml of LB medium (5 g/L yeast extract, 10 g/L tryptone, 10 g/L NaCl, pH 7.0, with additional 100 mg/L spectinomycine sulfate) in a 100 ml shaking flask were inoculated with a single colony from a fresh incubated agar plate and cultivated at 37° C. and 200 rpm for 7 h to an $OD_{600nm}$>3.0.

For the second preculture 8×50 ml of M9 medium (pH 7.40, $Na_2HPO_4 \times 12\ H_2O$ 13.68 g/L, $KH_2PO_4$ 3.00 g/L, NaCl 0.50 g/L, $NH_4Cl$ 2.00 g/L, $NH_4$acetate 5.00 g/L, $MgSO_4 \times 7H_2O$ 0.49 g/L, HCl (25%) 0.13 ml/L, $MnCl_2 \times 7\ H_2O$ 1.91 mg/L, $ZnSO_4 \times 7\ H_2O$ 1.87 mg/L, Na-EDTA$\times 2H_2O$ 0.84 mg/L, $H_3BO_3$ 0.30 mg/L, $Na_2MoO_4 \times 2\ H_2O$ 0.25 mg/L, $CaCl_2 \times 2\ H_2O$ 4.70 mg/L, $FeSO_4 \times 7\ H_2O$ 17.80 mg/L, $CuCl_2 \times 2\ H_2O$ 0.15 mg/L, with additional 100 mg/L spectinomycine sulfate, 3 mM methionine and 3 mM lysine) in a 500 ml shaking flask were inoculated with 0.5 ml cell suspension each from the pooled first precultures and cultivated at 37° C. and 200 rpm for 18 h to an $OD_{600nm}$>1.5.

Then the cell suspension was centrifuged, washed with fresh M9 medium and centrifuged again. For the main culture 200 mL of fresh M9 medium (without methionine and lysine) in a 500 mL glass bottle were inoculated with centrifuged and washed cells from the preculture to an $OD_{600nm}$ of 1.0. The cultivation was carried out in a pressure-resistant glass bottle that can be closed airtight with a butyl rubber stopper. The culture was incubated in an open water bath shaker at 30° C., 150 rpm and a ventilation rate of 4 L/h with synthetic air (79.5% $N_2$, 20.5% $O_2$) for 119 h. The air was discharged into the medium through a sparger with a pore size of 10 μm, which was mounted in the center of the reactors. The pH was hold at 7.3 by automatic addition of 25% acetic acid. After 4 h 1 mM IPTG was added for induction. A sample was taken from the fermentation after 119 h and analyzed using LC-MS. HR-LCMS was measured on an Accela 1250 with LTQ-Orbitrap Elite equipped with 150×2 mm Accucore aq C18 (R138) column. Gradient elution was 0% B(1)-19-80% B(15) at 0.2 mL/min flow rate and 40° C. Eluent A was water with 0.05% perfluorbutyric acid and Eluent B was methanol with 0.05% perfluorbutyric acid. A peak eluting at 6.68 minutes with m/z $[M+H]^+$ 204.0868 was identified as O-acetyl-N-acetamido-DL-homoserine.

The invention claimed is:

1. A compound of general formula I:

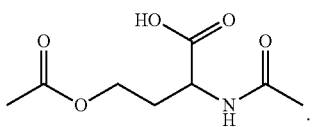

(I)

2. The compound of claim 1, wherein the compound is O-acetyl-N-acetamido-L-homoserine or O-acetyl-N-acetamido-D-homoserine.

3. A method of producing N-acetyl homoserine and/or derivatives thereof, the method comprising contacting at least one recombinant *Escherichia coli* cell in an aqueous medium with acetate wherein the recombinant *Escherichia coli* cell comprises an increased activity relative to a wild type cell of:
   (a) a homoserine dehydrogenase (EC 1.1.1.3) comprising the amino acid sequence SEQ ID NO: 3 and an aspartokinase (EC2.7.2.4) comprising the acid sequence of SEQ ID NO: 4; and
   (b) a homoserine O-acetyl transferase (EC2.3.1.31) comprising the amino acid sequence of SEQ ID NO: 1;
   wherein the recombinant cell further comprises inactivated genes coding for:
   (c) a diaminopimelate decarboxylase (EC4.1.1.20); and
   (d) a homoserine O-transsuccinylase (EC2.3.1.46);
   thereby producing the N-acetyl homoserine and/or derivatives thereof
   and wherein the acetate is maintained at a concentration of at least 0.001 g/L in the aqueous medium.

4. The method of claim 3, wherein the acetate is exogenously produced.

5. The method of claim 3, wherein the method further comprises extracting the N-acetyl homoserine and derivatives thereof from the aqueous medium.

6. The method of claim 3, wherein the N-acetyl homoserine and/or derivatives thereof is selected from the group consisting of: O-acetyl-N-acetamido-L-homoserine; O-acetyl-N-acetamido-D-homoserine; N-acetamido-L-homoserine; and N-acetamido-D-homoserine.

7. A method of producing N-acetyl homoserine and/or derivatives thereof, the method comprising contacting at least one recombinant *Corynebacterium glutamicum* cell in an aqueous medium with acetate wherein the recombinant *Corynebacterium glutamicum* cell comprises an increased activity relative to a wild type cell of:
   (a) a feedback-resistant homoserine dehydrogenase (EC 1.1.1.3) Hom and a feedback-resistant aspartokinase (EC2.7.2.4) LysC comprising the acid sequence SEQ ID NO: 4; and
   (b) a homoserine 0-acetyl transferase (EC2.3.1.31) MetX;
   thereby producing the N-acetyl homoserine and/or derivatives thereof
   and wherein the acetate is maintained at a concentration of at least 0.001 g/L in the aqueous medium.

8. The method of claim 7, wherein the acetate is exogenously produced.

9. The method of claim 7, wherein the method further comprises extracting the N-acetyl homoserine and derivatives thereof from the aqueous medium.

10. The method of claim 7, wherein the N-acetyl homoserine and/or derivatives thereof is selected from the group consisting of: O-acetyl-N-acetamido-L-homoserine; O-acetyl-N-acetamido-D-homoserine; N-acetamido-L-homoserine; and N-acetamido-D-homoserine.

\* \* \* \* \*

SEQUENCE LISTING

```
<160> NUMBER OF SEQ ID NOS: 52

<210> SEQ ID NO 1
<211> LENGTH: 377
<212> TYPE: PRT
<213> ORGANISM: Corynebacterium glutamicum

<400> SEQUENCE: 1

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
            20                  25                  30
```

Tyr His Arg Trp Gly Glu Tyr Arg Val Asp Lys Glu Gly Arg Ser Asn
                35                  40                  45

Val Val Leu Ile Glu His Ala Leu Thr Gly Asp Ser Asn Ala Ala Asp
 50                  55                  60

Trp Trp Ala Asp Leu Leu Gly Pro Gly Lys Ala Ile Asn Thr Asp Ile
 65                  70                  75                  80

Tyr Cys Val Ile Cys Thr Asn Val Ile Gly Cys Asn Gly Ser Thr
                 85                  90                  95

Gly Pro Gly Ser Met His Pro Asp Gly Asn Phe Trp Gly Asn Arg Phe
                100                 105                 110

Pro Ala Thr Ser Ile Arg Asp Gln Val Asn Ala Glu Lys Gln Phe Leu
                115                 120                 125

Asp Ala Leu Gly Ile Thr Thr Val Ala Ala Val Leu Gly Gly Ser Met
                130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
                180                 185                 190

Trp His Glu Gly Asn Tyr Tyr Glu Ser Gly Cys Asn Pro Ala Thr Gly
                195                 200                 205

Leu Gly Ala Ala Arg Arg Ile Ala His Leu Thr Tyr Arg Gly Glu Leu
                210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
                260                 265                 270

Tyr Val Leu Leu Thr Asp Ala Leu Asn Arg His Asp Ile Gly Arg Asp
                275                 280                 285

Arg Gly Gly Leu Asn Lys Ala Leu Glu Ser Ile Lys Val Pro Val Leu
                290                 295                 300

Val Ala Gly Val Asp Thr Asp Ile Leu Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
                340                 345                 350

Arg Ile Val Arg Asn Phe Phe Ser Leu Ile Ser Pro Asp Glu Asp Asn
                355                 360                 365

Pro Ser Thr Tyr Ile Glu Phe Tyr Ile
                370                 375

<210> SEQ ID NO 2
<211> LENGTH: 1134
<212> TYPE: DNA
<213> ORGANISM: Corynebacterium glutamicum

<400> SEQUENCE: 2
atgcccaccc tcgcgccttc aggtcaactt gaaatccaag cgatcggtga tgtctccacc      60
gaagccggag caatcattac aaacgctgaa atcgcctatc accgctgggg tgaataccgc     120
gtagataaag aaggacgcag caatgtcgtt ctcatcgaac acgccctcac tggagattcc     180

```
aacgcagccg attggtgggc tgacttgctc ggtcccggca aagccatcaa cactgatatt    240
tactgcgtga tctgtaccaa cgtcatcggt ggttgcaacg gttccaccgg acctggctcc    300
atgcatccag atggaaattt ctggggtaat cgcttccccg ccacgtccat tcgtgatcag    360
gtaaacgccg aaaaacaatt cctcgacgca ctcggcatca ccacggtcgc cgcagtactt    420
ggtggttcca tgggtggtgc ccgcacccta gagtgggccg caatgtaccc agaaactgtt    480
ggcgcagctg ctgttcttgc agtttctgca cgcgccagcg cctggcaaat cggcattcaa    540
tccgcccaaa ttaaggcgat tgaaaacgac caccactggc acgaaggcaa ctactacgaa    600
tccggctgca acccagccac cggactcggc gccgcccgac gcatcgccca cctcacctac    660
cgtggcgaac tagaaatcga cgaacgcttc ggcaccaaag cccaaaagaa cgaaaaccca    720
ctcggtccct accgcaagcc cgaccagcgc ttcgccgtgg aatcctactt ggactaccaa    780
gcagacaagc tagtacagcg tttcgacgcc ggctcctacg tcttgctcac cgacgccctc    840
aaccgccacg acattggtcg cgaccgcgga ggcctcaaca aggcactcga atccatcaaa    900
gttccagtcc ttgtcgcagg cgtagatacc gatattttgt accccctacca ccagcaagaa    960 cacctctcca gaaacctggg aaatctactg gcaatggcaa aaatcgtatc ccctgtcggc   1020
cacgatgctt tcctcaccga aagccgccaa atggatcgca tcgtgaggaa cttcttcagc   1080
ctcatctccc cagacgaaga caaccctttcg acctacatcg agttctacat ctaa        1134
```

<210> SEQ ID NO 3
<211> LENGTH: 820
<212> TYPE: PRT
<213> ORGANISM: Escherichia coli

<400> SEQUENCE: 3

```
Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
    130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205
```

```
Tyr Ser Ala Ala Val Leu Ala Ala Cys Leu Arg Ala Asp Cys Cys Glu
    210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
                260                 265                 270

Ile Ala Gln Phe Gln Ile Pro Cys Leu Ile Lys Asn Thr Gly Asn Pro
                275                 280                 285

Gln Ala Pro Gly Thr Leu Ile Gly Ala Ser Arg Asp Glu Asp Glu Leu
    290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Phe Val Val Leu Ile Thr Gln Ser
                340                 345                 350

Ser Ser Glu Tyr Ser Ile Ser Phe Cys Val Pro Gln Ser Asp Cys Val
    355                 360                 365

Arg Ala Glu Arg Ala Met Gln Glu Glu Phe Tyr Leu Glu Leu Lys Glu
370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
                420                 425                 430

Gly Ser Ser Glu Arg Ser Ile Ser Val Val Val Asn Asn Asp Asp Ala
    435                 440                 445

Thr Thr Gly Val Arg Val Thr His Gln Met Leu Phe Asn Thr Asp Gln
    450                 455                 460

Val Ile Glu Val Phe Val Ile Gly Val Gly Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
                500                 505                 510

Val His Gly Leu Asn Leu Glu Asn Trp Gln Glu Glu Leu Ala Gln Ala
    515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
                580                 585                 590

Arg Tyr Ala Ala Glu Lys Ser Arg Arg Lys Phe Leu Tyr Asp Thr Asn
    595                 600                 605

Val Gly Ala Gly Leu Pro Val Ile Glu Asn Leu Gln Asn Leu Leu Asn
    610                 615                 620
```

-continued

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
            645                 650                 655

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
            675                 680                 685

Glu Thr Gly Arg Glu Leu Glu Leu Ala Asp Ile Glu Ile Glu Pro Val
            690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
            725                 730                 735

Arg Asp Glu Gly Lys Val Leu Arg Tyr Val Gly Asn Ile Asp Glu Asp
            740                 745                 750

Gly Val Cys Arg Val Lys Ile Ala Glu Val Asp Gly Asn Asp Pro Leu
            755                 760                 765

Phe Lys Val Lys Asn Gly Glu Asn Ala Leu Ala Phe Tyr Ser His Tyr
770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
            805                 810                 815

Lys Leu Gly Val
            820

<210> SEQ ID NO 4
<211> LENGTH: 449
<212> TYPE: PRT
<213> ORGANISM: Escherichia coli

<400> SEQUENCE: 4

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
            115                 120                 125

Ile Leu Arg Glu Arg Asp Val Gln Ala Gln Trp Phe Asp Val Arg Lys
130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
                180                 185                 190

Thr Thr Thr Leu Gly Arg Gly Gly Ser Asp Tyr Thr Ala Ala Leu Leu
            195                 200                 205

Ala Glu Ala Leu His Ala Ser Arg Val Asp Ile Trp Thr Asp Val Pro
210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
                260                 265                 270

Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
        290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Ile
                340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
        370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
            435                 440                 445

Glu

<210> SEQ ID NO 5
<211> LENGTH: 2463
<212> TYPE: DNA
<213> ORGANISM: Escherichia coli

<400> SEQUENCE: 5
atgcgagtgt tgaagttcgg cggtacatca gtggcaaatg cagaacgttt tctgcgtgtt     60
gccgatattc tggaaagcaa tgccaggcag gggcaggtgg ccaccgtcct ctctgccccc    120
gccaaaatca ccaaccacct ggtggcgatg attgaaaaaa ccattagcgg ccaggatgct    180
ttacccaata tcagcgatgc cgaacgtatt tttgccgaac ttttgacggg actcgccgcc    240
gcccagccgg ggttcccgct ggcgcaattg aaaactttcg tcgatcagga atttgcccaa    300
ataaaacatg tcctgcatgg cattagtttg ttggggcagt gccggatag catcaacgct    360 gcgctgattt gcgtggcga gaaaatgtcg atcgccatta tggccggcgt attagaagcg    420
cgcggtcaca cgttactgt tatcgatccg gtcgaaaaac tgctggcagt ggggcattac    480
ctcgaatcta ccgtcgatat tgctgagtcc acccgccgta ttgcggcaag ccgcattccg    540

| | | | |
|---|---|---|---|
| gctgatcaca tggtgctgat ggcaggtttc accgccggta atgaaaaagg cgaactggtg | 600 |
| gtgcttggac gcaacggttc cgactactct gctgcggtgc tggctgcctg tttacgcgcc | 660 |
| gattgttgcg agatttggac ggacgttgac ggggtctata cctgcgaccc gcgtcaggtg | 720 |
| cccgatgcga ggttgttgaa gtcgatgtcc taccaggaag cgatggagct ttcctacttc | 780 |
| ggcgctaaag ttcttcaccc ccgcaccatt accccatcg cccagttcca gatcccttgc | 840 |
| ctgattaaaa ataccggaaa tcctcaagca ccaggtacgc tcattggtgc cagccgtgat | 900 |
| gaagacgaat taccggtcaa gggcatttcc aatctgaata acatggcaat gttcagcgtt | 960 |
| tctggtccgg ggatgaaagg gatggtcggc atggcggcgc gcgtctttgc agcgatgtca | 1020 |
| cgcgcccgta ttttcgtggt gctgattacg caatcatctt ccgaatacag catcagtttc | 1080 |
| tgcgttccac aaagcgactg tgtgcgagct gaacgggcaa tgcaggaaga gttctacctg | 1140 |
| gaactgaaag aaggcttact ggagccgctg gcagtgacgg aacggctggc cattatctcg | 1200 |
| gtggtaggtg atggtatgcg caccttgcgt gggatctcgg cgaaattctt tgccgcactg | 1260 |
| gcccgcgcca atatcaacat tgtcgccatt gctcagggat cttctgaacg ctcaatctct | 1320 |
| gtcgtggtaa ataacgatga tgcgaccact ggcgtgcgcg ttactcatca gatgctgttc | 1380 |
| aataccgatc aggttatcga agtgtttgtg attggcgtcg gtggcgttgg cggtgcgctg | 1440 |
| ctggagcaac tgaagcgtca gcaaagctgg ctgaagaata acatatcga cttacgtgtc | 1500 |
| tgcggtgttg ccaactcgaa ggctctgctc accaatgtac atggccttaa tctggaaaac | 1560 |
| tggcaggaag aactggcgca agccaaagag ccgtttaatc tcgggcgctt aattcgcctc | 1620 |
| gtgaaagaat atcatctgct gaacccggtc attgttgact gcacttccag ccaggcagtg | 1680 |
| gcggatcaat atgccgactt cctgcgcgaa ggtttccacg ttgtcacgcc gaacaaaaag | 1740 |
| gccaacacct cgtcgatgga ttactaccat cagttgcgtt atgcggcgga aaaatcgcgg | 1800 |
| cgtaaattcc tctatgacac caacgttggg gctggattac cggttattga aacctgcaa | 1860 |
| aatctgctca atgcaggtga tgaattgatg aagttctccg gcattctttc tggttcgctt | 1920 |
| tcttatatct tcggcaagtt agacgaaggc atgagttct ccgaggcgac cacgctggcg | 1980 |
| cgggaaatgg gttataccga accggacccg cgagatgatc tttctggtat ggatgtggcg | 2040 |
| cgtaaactat tgattctcgc tcgtgaaacg ggacgtgaac tggagctggc ggatattgaa | 2100 |
| attgaacctg tgctgcccgc agagtttaac gccgagggtg atgttgccgc ttttatggcg | 2160 |
| aatctgtcac aactcgacga tctctttgcc gcgcgcgtgg cgaaggcccg tgatgaagga | 2220 |
| aaagttttgc gctatgttgg caatattgat gaagatggc tctgccgcgt gaagattgcc | 2280 |
| gaagtggatg gtaatgatcc gctgttcaaa gtgaaaaatg gcgaaaacgc cctggccttc | 2340 |
| tatagccact attatcagcc gctgccgttg gtactgcgcg atatggtgc gggcaatgac | 2400 |
| gttacagctg ccggtgtctt tgctgatctg ctacgtaccc tctcatggaa gttaggagtc | 2460 |
| tga | 2463 |

<210> SEQ ID NO 6
<211> LENGTH: 1350
<212> TYPE: DNA
<213> ORGANISM: Escherichia coli

<400> SEQUENCE: 6

| | |
|---|---|
| atgtctgaaa ttgttgtctc caaatttggc ggtaccagcg tagctgattt tgacgccatg | 60 |
| aaccgcagcg ctgatattgt gctttctgat gccaacgtgc gtttagttgt cctctcggct | 120 |

-continued

```
tctgctggta tcactaatct gctggtcgct ttagctgaag gactggaacc tggcgagcga      180
ttcgaaaaac tcgacgctat ccgcaacatc cagtttgcca ttctggaacg tctgcgttac      240
ccgaacgtta tccgtgaaga gattgaacgt ctgctggaga acattactgt tctggcagaa      300
gcggcggcgc tggcaacgtc tccggcgctg acagatgagc tggtcagcca cggcgagctg      360
atgtcgaccc tgctgtttgt tgagatcctg cgcgaacgcg atgttcaggc acagtggttt      420
gatgtacgta aagtgatgcg taccaacgac cgatttggtc gtgcagagcc agatatagcc      480
gcgctggcgg aactggccgc gctgcagctg ctcccacgtc tcaatgaagg cttagtgatc      540
acccagggat ttatcggtag cgaaaataaa ggtcgtacaa cgacgcttgg ccgtggaggc      600
agcgattata cggcagcctt gctggcggag gctttacacg catctcgtgt tgatatctgg      660
accgacgtcc cgggcatcta caccaccgat ccacgcgtag tttccgcagc aaaacgcatt      720
gatgaaatcg cgtttgccga agcggcagag atggcaactt tggtgcaaa agtactgcat      780 ccggcaacgt tgctacccgc agtacgcagc gatatcccgg tctttgtcgg ctccagcaaa      840
gacccacgcg caggtggtac gctggtgtgc aataaaactg aaaatccgcc gctgttccgc      900
gctctggcgc ttcgtcgcaa tcagactctg ctcactttgc acagcctgaa tatgctgcat      960
tctcgcggtt tcctcgcgga agttttcggc atcctcgcgc ggcataatat tcggtagac     1020 ttaatcacca cgtcagaagt gagcgtggca ttaatccttg ataccaccgg ttcaacctcc     1080
actggcgata cgttgctgac gcaatctctg ctgatggagc tttccgcact gtgtcgggtg     1140
gaggtggaag aaggtctggc gctggtcgcg ttgattggca atgacctgtc aaaagcctgc     1200
ggcgttggca agaggtatt cggcgtactg gaaccgttca acattcgcat gatttgttat      1260
ggcgcatcca gccataacct gtgcttcctg gtgcccggcg aagatgccga gcaggtggtg     1320
caaaaactgc atagtaattt gtttgagtaa                                     1350
```

<210> SEQ ID NO 7
<211> LENGTH: 420
<212> TYPE: PRT
<213> ORGANISM: Escherichia coli

<400> SEQUENCE: 7

```
Met Pro His Ser Leu Phe Ser Thr Asp Thr Asp Leu Thr Ala Glu Asn
1               5                   10                  15

Leu Leu Arg Leu Pro Ala Glu Phe Gly Cys Pro Val Trp Val Tyr Asp
            20                  25                  30

Ala Gln Ile Ile Arg Arg Gln Ile Ala Ala Leu Lys Gln Phe Asp Val
        35                  40                  45

Val Arg Phe Ala Gln Lys Ala Cys Ser Asn Ile His Ile Leu Arg Leu
    50                  55                  60

Met Arg Glu Gln Gly Val Lys Val Asp Ser Val Ser Leu Gly Glu Ile
65                  70                  75                  80

Glu Arg Ala Leu Ala Ala Gly Tyr Asn Pro Gln Thr His Pro Asp Asp
                85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
        115                 120                 125

Gln Leu Gly Gln Val Ser Pro Gly His Arg Val Trp Leu Arg Val Asn
    130                 135                 140

Pro Gly Phe Gly His Gly His Ser Gln Lys Thr Asn Thr Gly Gly Glu
145                 150                 155                 160
```

```
Asn Ser Lys His Gly Ile Trp Tyr Thr Asp Leu Pro Ala Ala Leu Asp
            165                 170                 175

Val Ile Gln Arg His His Leu Gln Leu Val Gly Ile His Met His Ile
        180                 185                 190

Gly Ser Gly Val Asp Tyr Ala His Leu Glu Gln Val Cys Gly Ala Met
    195                 200                 205

Val Arg Gln Val Ile Glu Phe Gly Gln Asp Leu Gln Ala Ile Ser Ala
210                 215                 220

Gly Gly Gly Leu Ser Val Pro Tyr Gln Gln Gly Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
        275                 280                 285

Gln Met Gly Ser Arg His Phe Val Leu Val Asp Ala Gly Phe Asn Asp
    290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
        355                 360                 365

Tyr Leu Val Leu His Asp Thr Gly Ala Tyr Gly Ala Ser Met Ser Ser
    370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Arg Gln Thr Ile Glu Glu Leu Leu Ala
                405                 410                 415

Leu Glu Leu Leu
            420

<210> SEQ ID NO 8
<211> LENGTH: 1263
<212> TYPE: DNA
<213> ORGANISM: Escherichia coli

<400> SEQUENCE: 8
atgccacatt tactgttcag caccgatacc gatctcaccg ccgaaaatct gctgcgtttg      60
cccgctgaat ttggctgccc ggtgtgggtc tacgatgcgc aaattattcg tcggcagatt     120
gcagcgctga acagtttga tgtggtgcgc tttgcacaga agcctgttc caatattcat       180 attttgcgct taatgcgtga gcagggcgtg aaagtggatt ccgtctcgtt aggcgaaata     240
gagcgtgcgt tggcggcggg ttacaatccg caaacgcacc ccgatgatat tgtttttacg     300
gcagatgtta tcgatcaggc gacgcttgaa cgcgtcagtg aattgcaaat tccggtgaat     360
gcgggttctg ttgatatgct cgaccaactg ggccaggttt cgccagggca tcgggtatgg     420
ctgcgcgtta atccgggggtt tggtcacgga catagccaaa aaccaatac cggtggcgaa     480 aacagcaagc acggtatctg gtacaccgat ctgcccgccg cactggacgt gatcaaacgt     540
catcatctgc agctggtcgg cattcacatg cacattggtt ctggcgttga ttatgcccat     600
```

```
ctggaacagg tgtgtggtgc tatggtgcgt caggtcatcg aattcggtca ggatttacag    660
gctatttctg cgggcggtgg gctttctgtt cctatcaac agggtgaaga ggcggttgat    720
accgaacatt attatggtct gtggaatgcc gcgcgtgagc aaatcgcccg ccatttgggc    780
caccctgtga aactgaaaat tgaaccgggt cgcttcctgg tagcgcagtc tggcgtatta    840
attactcagg tgcggagcgt caaacaaatg gggagccgcc actttgtgct ggttgatgcc    900
gggttcaacg atctgatgcg cccggcaatg tacggtagtt accaccatat cagtgccctg    960
gcagctgatg gtcgttctct ggaacacgcg ccaacggtgg aaaccgtcgt cgccggaccg    1020
ttatgtgaat cgggcgatgt ctttacccag caggaagggg gaaatgttga acccgcgcc    1080 ttgccggaag tgaaggcagg tgattatctg gtactgcatg atacaggggc atatggcgca    1140
tcaatgtcat ccaactacaa tagccgtccg ctgttaccag aagttctgtt tgataatggt    1200
caggcgcggt tgattcgccg tcgccagacc atcgaagaat tactggcgct ggaattgctt    1260
taa                                                                 1263
```

<210> SEQ ID NO 9
<211> LENGTH: 309
<212> TYPE: PRT
<213> ORGANISM: Escherichia coli

<400> SEQUENCE: 9

```
Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
```

```
            245                 250                 255
Pro Asp Val Pro Tyr Asn Tyr Phe Pro His Asn Asp Pro Gln Asn Thr
        260                 265                 270

Pro Arg Ala Ser Trp Arg Ser His Gly Asn Leu Leu Phe Thr Asn Trp
    275                 280                 285

Leu Asn Tyr Tyr Val Tyr Gln Ile Thr Pro Tyr Asp Leu Arg His Met
290                 295                 300

Asn Pro Thr Leu Asp
305

<210> SEQ ID NO 10
<211> LENGTH: 930
<212> TYPE: DNA
<213> ORGANISM: Escherichia coli

<400> SEQUENCE: 10
atgccgattc gtgtgccgga cgagctaccc gccgtcaatt tcttgcgtga agaaaacgtc    60
tttgtgatga caacttctcg tgcgtctggt caggaaattc gtccacttaa ggttctgatc   120
cttaacctga tgccgaagaa gattgaaact gaaaatcagt ttctgcgcct gctttcaaac   180
tcacctttgc aggtcgatat tcagctgttg cgcatcgatt cccgtgaatc gcgcaacacg   240
cccgcagagc atctgaacaa cttctactgt aactttgaag atattcagga tcagaacttt   300
gacggtttga ttgtaactgg tgcgccgctg ggcctggtgg agtttaatga tgtcgcttac   360
tggccgcaga tcaaacaggt gctggagtgg tcgaaagatc acgtcacctc gacgctgttt   420
gtctgctggg cggtacaggc cgcgctcaat atcctctacg cattcctaa gcaaactcgc    480 accgaaaaac tctctggcgt ttacgagcat catattctcc atcctcatgc gcttctgacg   540
cgtggctttg atgattcatt cctggcaccg cattcgcgct atgctgactt ccggcagcg    600 ttgattcgtg attacaccga tctggaaatt ctggcagaga cggaagaagg ggatgcatat   660
ctgtttgcca gtaaagataa gcgcattgcc tttgtgacgg gccatcccga atatgatgcg   720
caaacgctgg cgcaggaatt tttccgcgat gtggaagccg actagaccc ggatgtaccg    780 tataactatt tcccgcacaa tgatccgcaa aataccgcg agcgagctg gcgtagtcac     840 ggtaatttac tgtttaccaa ctggctcaac tattacgtct accagatcac gccatacgat   900
ctacggcaca tgaatccaac gctggattaa                                    930

<210> SEQ ID NO 11
<211> LENGTH: 7734
<212> TYPE: DNA
<213> ORGANISM: Artificial Sequence
<220> FEATURE:
<223> OTHER INFORMATION: Plasmid

<400> SEQUENCE: 11
cgggatctcg acgctctccc ttatgcgact cctgcgttta gggaaagagc atttgtcaga    60
atatttaagg gcgcctgtca ctttgcttga tatatgagaa ttatttaacc ttataaatga   120
gaaaaaagca acgcacttta ataagatac gttgcttttt cgattgatga acacctataa    180
ttaaactatt catctattat ttatgatttt ttgtatatac aatatttcta gtttgttaaa   240
gagaattaag aaaataaatc tcgaaaataa taagggaaa atcagttttt gatatcaaaa    300
ttatacatgt caacgataat acaaaatata atacaaacta agatgttta tcagtattta    360 ttatgcattt agaataccctt ttgtgtcgcc cttattcgac tccctataga agttcctatt   420
ctctagaaag tataggaact tcccttcatt ttggatccaa ttgtgagcgg ataacaatta   480
```

```
cgagcttcat gcacagtgat cgacgctgtt gacaattaat catcggctcg tataatgtgt      540
ggatgtggaa ttgtgagcgc tcacaattcc acaacggttt ccctctagaa ataattttgt      600
ttaacaggag gtaaaacata tgcgagtgtt gaagttcggc ggtacatcag tggcaaatgc      660
agaacgtttt ctgcgtgttg ccgatattct ggaaagcaat gccaggcagg ggcaggtggc      720
caccgtcctc tctgccccg ccaaaatcac caaccacctg gtggcgatga ttgaaaaaac      780
cattagcggc caggatgctt tacccaatat cagcgatgcc gaacgtattt ttgccgaact      840
tttgacggga ctcgccgccg cccagccggg gttcccgctg gcgcaattga aaactttcgt      900
cgatcaggaa tttgcccaaa taaaacatgt cctgcatggc attagtttgt tggggcagtg      960
cccggatagc atcaacgctg cgctgatttg ccgtggcgag aaaatgtcga tcgccattat     1020
ggccggcgta ttagaagcgc gcggtcacaa cgttactgtt atcgatccgg tcgaaaaact     1080
gctggcagtg gggcattacc tcgaatctac cgtcgatatt gctgagtcca cccgccgtat     1140
tgcggcaagc cgcattccgg ctgatcacat ggtgctgatg caggtttca ccgccggtaa      1200 tgaaaaaggc gaactggtgg tgcttggacg caacggttcc gactactctg ctgcggtgct     1260
ggctgcctgt ttacgcgccg attgttgcga gatttggacg gacgttgacg ggtctatac      1320 ctgcgacccg cgtcaggtgc cgatgcgag gttgttgaag tcgatgtcct accaggaagc      1380
gatggagctt cctacttcg gcgctaaagt tcttcacccc cgcaccatta ccccatcgc      1440 ccagttccag atcccttgcc tgattaaaaa taccggaaat cctcaagcac caggtacgct     1500
cattggtgcc agccgtgatg aagacgaatt accggtcaag gcatttcca atctgaataa      1560 catggcaatg ttcagcgttt ctggtccggg gatgaaaggg atggtcggca tggcggcgcg     1620 cgtcttttgca gcgatgtcac gcgcccgtat tttcgtggtg ctgattacgc aatcatcttc     1680
cgaatacagc atcagtttct gcgttccaca aagcgactgt gtgcgagctg aacgggcaat     1740
gcaggaagag ttctacctgg aactgaaaga aggcttactg gagccgctgg cagtgacgga     1800
acggctggcc attatctcgg tggtaggtga tggtatgcgc accttgcgtg ggatctcggc     1860
gaaattcttt gccgcactgg cccgcgccaa tatcaacatt gtcgccattg ctcagggatc     1920
ttctgaacgc tcaatctctg tcgtggtaaa taacgatgat gcgaccactg gcgtgcgcgt     1980
tactcatcag atgctgttca ataccgatca ggttatcgaa gtgtttgtga ttggcgtcgg     2040
tggcgttggc ggtgcgctgc tggagcaact gaagcgtcag caaagctggc tgaagaataa     2100
acatatcgac ttacgtgtct gcggtgttgc caactcgaag gctctgctca ccaatgtaca     2160
tggccttaat ctggaaaact ggcaggaaga actggcgcaa gccaaagagc cgtttaatct     2220
cgggcgctta attcgcctcg tgaaagaata tcatctgctg aacccggtca ttgttgactg     2280
cacttccagc caggcagtgg cggatcaata tgccgacttc ctgcgcgaag gtttccacgt     2340
tgtcacgccg aacaaaaagg ccaacacctc gtcgatggat tactaccatc agttgcgtta     2400
tgcggcggaa aaatcgcggc gtaaattcct ctatgacacc aacgttgggg ctggattacc     2460
ggttattgag aacctgcaaa atctgctcaa tgcaggtgat gaattgatga agttctccgg     2520 cattcttttct ggttcgcttt cttatatctt cggcaagtta gacgaaggca tgagtttctc     2580
cgaggcgacc acgctggcgc gggaaatggg ttataccgaa ccggaccgc gagatgatct      2640 ttctggtatg gatgtggcgc gtaaactatt gattctcgct cgtgaaacgg acgtgaact      2700 ggagctggcg gatattgaaa ttgaacctgt gctgccgca gagtttaacg ccgagggtga      2760
tgttgccgct tttatggcga atctgtcaca actcgacgat ctctttgccg cgcgcgtggc     2820
```

```
gaaggcccgt gatgaaggaa aagttttgcg ctatgttggc aatattgatg aagatggcgt    2880
ctgccgcgtg aagattgccg aagtggatgg taatgatccg ctgttcaaag tgaaaaatgg    2940
cgaaaacgcc ctggccttct atagccacta ttatcagccg ctgccgttgg tactgcgcgg    3000
atatggtgcg ggcaatgacg ttacagctgc cggtgtcttt gctgatctgc tacgtaccct    3060
ctcatggaag ttaggagtct gataaggcag tgagcgcaac gcaattaatg taagttagct    3120
cactcattag cacccccagg cttgacactt tatgcttccg gctcgtataa tgtgtggaat    3180
tgtgagcgga taacaataac aatttcacac aggatctagg aaccaaggag agtggcatgc    3240
ccaccctcgc gccttcaggt caacttgaaa tccaagcgat cggtgatgtc tccaccgaag    3300
ccggagcaat cattacaaac gctgaaatcg cctatcaccg ctggggtgaa taccgcgtag    3360
ataaagaagg acgcagcaat gtcgttctca tcgaacacgc cctcactgga gattccaacg    3420
cagccgattg gtgggctgac ttgctcggtc ccggcaaagc catcaacact gatatttact    3480
gcgtgatctg taccaacgtc atcggtggtt gcaacggttc caccggacct ggctccatgc    3540
atccagatgg aaatttctgg ggtaatcgct tccccgccac gtccattcgt gatcaggtaa    3600
acgccgaaaa acaattcctc gacgcactcg gcatcaccac ggtcgccgca gtacttggtg    3660
gttccatggg tggtgcccgc accctagagt gggccgcaat gtaccagaaa actgttggcg    3720
cagctgctgt tcttgcagtt tctgcacgcg ccagcgcctg gcaaatcggc attcaatccg    3780
cccaaattaa ggcgattgaa aacgaccacc actggcacga aggcaactac tacgaatccg    3840
gctgcaaccc agccaccgga ctcggcgccg cccgacgcat cgcccacctc acctaccgtg    3900
gcgaactaga aatcgacgaa cgcttcggca ccaaagccca aaagaacgaa acccactcg    3960 gtccctaccg caagcccgac cagcgcttcg ccgtggaatc ctacttggac taccaagcag    4020
acaagctagt cagcgtttc gacgccggct cctacgtctt gctcaccgac gccctcaacc    4080
gccacgacat tggtcgcgac cgcggaggcc tcaacaaggc actcgaatcc atcaaagttc    4140
cagtccttgt cgcaggcgta gataccgata ttttgtaccc ctaccaccag caagaacacc    4200
tctccagaaa cctgggaaat ctactggcaa tggcaaaaat cgtatcccct gtcggccacg    4260
atgctttcct caccgaaagc cgccaaatgg atcgcatcgt gaggaacttc ttcagcctca    4320
tctccccaga cgaagacaac ccttcgacct acatcgagtt ctacatctaa taggtctggt    4380
aaagaaaccg ctgctgcgaa atttgaacgc cagcacatgg actcgtctac tagcgcagct    4440
taattaacct aggctgctgc caccgctgag caataactag cataaccct tggggcctct    4500 aaacgggtct tgaggggttt tttgctgaaa cctcaggcat ttgagaagca cacggtcaca    4560
ctgcttccgg tagtcaataa accggtaaac cagcaataga cataagcggc tatttaacga    4620
ccctgccctg aaccgacgac cgggtcatcg tggccggatc ttgcggcccc tcggcttgaa    4680
cgaattgtta gacattattt gccgactacc ttggtgatct cgccttttcac gtagtggaca    4740 aattcttcca actgatctgc gcgcgaggcc aagcgatctt cttcttgtcc aagataagcc    4800
tgtctagctt caagtatgac gggctgatac tgggccggca ggcgctccat tgcccagtcg    4860
gcagcgacat ccttcggcgc gattttgccg gttactgcgc tgtaccaaat gcgggacaac    4920
gtaagcacta catttcgctc atcgccagcc cagtcgggcg gcgagttcca tagcgttaag    4980
gtttcattta gcgcctcaaa tagatcctgt tcaggaaccg gatcaaagag ttcctccgcc    5040
gctggaccta ccaaggcaac gctatgttct cttgcttttg tcagcaagat agccagatca    5100
atgtcgatct tggctggctc gaagataact gcaagaatgt cattgcgctg ccattctcca    5160
aattgcagtt cgcgcttagc tggataacgc cacggaatga tgtcgtcgtg cacaacaatg    5220
```

```
gtgacttcta cagcgcggag aatctcgctc tctccagggg aagccgaagt tccaaaagg    5280 tcgttgatca aagctcgccg cgttgtttca tcaagcctta cggtcaccgt aaccagcaaa    5340
tcaatatcac tgtgtggctt caggccgcca tccactgcgg agccgtacaa atgtacggcc    5400
agcaacgtcg gttcgagatg gcgctcgatg acgccaacta cctctgatag ttgagtcgat    5460
acttcggcga tcaccgcttc cctcatactc ttccttttc aatattattg aagcatttat     5520
cagggttatt gtctcatgag cggatacata tttgaatgta tttagaaaaa taaacaaata    5580
gctagctcac tcggtcgcta cgctccgggc gtgagactgc ggcgggcgct gcggacacat    5640
acaaagttac ccacagattc cgtggataag caggggacta acatgtgagg caaaacagca    5700
gggccgcgcc ggtggcgttt ttccataggc tccgccctcc tgccagagtt cacataaaca    5760 gacgctttc cggtgcatct gtgggagccg tgaggctcaa ccatgaatct gacagtacgg     5820
gcgaaacccg acaggactta agatcccca ccgtttccgg cgggtcgctc cctcttgcgc     5880
tctcctgttc cgaccctgcc gtttaccgga tacctgttcc gcctttctcc cttacgggaa    5940
gtgtggcgct ttctcatagc tcacacactg gtatctcggc tcggtgtagg tcgttcgctc    6000
caagctgggc tgtaagcaag aactcccgt tcagcccgac tgctgcgcct tatccggtaa     6060
ctgttcactt gagtccaacc cggaaaagca cggtaaaacg ccactggcag cagccattgg    6120
taactgggag ttcgcagagg atttgtttag ctaaacacgc ggttgctctt gaagtgtgcg    6180
ccaaagtccg gctacactgg aaggacagat ttggttgctg tgctctgcga agccagtta    6240 ccacggttaa gcagttcccc aactgactta accttcgatc aaaccacctc cccaggtggt    6300
tttttcgttt acagggcaaa agattacgcg cagaaaaaaa ggatctcaag aagatccttt    6360
gatcttttct actgaaccgc tctagatttc agtgcaattt atctcttcaa atgtagcacc    6420
tgaagtcagc cccatacgat ataagttgta attctcatgt tagtcatgcc ccgcgcccac    6480
cggaaggagc tgactgggtt gaaggctctc aagggcatcg gtcgagatcc cggtgcctaa    6540
tgagtgagct aacttacatt aattgcgttg cgctcactgc ccgctttcca gtcgggaaac    6600
ctgtcgtgcc agctgcatta atgaatcggc caacgcgcgg ggagaggcgg tttgcgtatt    6660
gggcgccagg gtggtttttc ttttcaccag tgagacgggc aacagctgat tgcccttcac    6720
cgcctggccc tgagagagtt gcagcaagcg gtccacgctg gtttgcccca gcaggcgaaa    6780
atcctgtttg atggtggtta acggcgggat ataacatgag ctgtcttcgg tatcgtcgta    6840
tcccactacc gagatgtccg caccaacgcg cagcccggac tcggtaatgg cgcgcattgc    6900
gcccagcgcc atctgatcgt tggcaaccag catcgcagtg gaacgatgc cctcattcag     6960 catttgcatg gtttgttgaa aaccggacat ggcactccag tcgccttccc gttccgctat    7020
cggctgaatt tgattgcgag tgagatattt atgccagcca gcagacgca gacgcgccga     7080 gacagaactt aatgggcccg ctaacagcgc gatttgctgg tgacccaatg cgaccagatg    7140
ctccacgccc agtcgcgtac cgtcttcatg ggagaaaata atactgttga tgggtgtctg    7200
gtcagagaca tcaagaaata cgccggaac attagtgcag gcagcttcca cagcaatggc     7260
atcctggtca tccagcggat agttaatgat cagcccactg acgcgttgcg cgagaagatt    7320
gtgcaccgcc gctttacagg cttcgacgcc gcttcgttct accatcgaca ccaccacgct    7380
ggcacccagt tgatcggcgc gagatttaat cgccgcgaca atttgcgacg gcgcgtgcag    7440
ggccagactg gaggtggcaa cgccaatcag caacgactgt ttgcccgcca gttgttgtgc    7500
cacgcggttg ggaatgtaat tcagctccgc catcgccgct tccactttt cccgcgtttt     7560
```

| | |
|---|---|
| cgcagaaacg tggctggcct ggttcaccac gcgggaaacg gtctgataag agacaccggc | 7620 |
| atactctgcg acatcgtata acgttactgg tttcacattc accaccctga attgactctc | 7680 |
| ttccgggcgc tatcatgcca taccgcgaaa ggttttgcgc cattcgatgg tgtc | 7734 |

<210> SEQ ID NO 12
<211> LENGTH: 6655
<212> TYPE: DNA
<213> ORGANISM: Artificial Sequence
<220> FEATURE:
<223> OTHER INFORMATION: pKO3 derivative HM-p-6

<400> SEQUENCE: 12

| | |
|---|---|
| cctttcgtct tcgaataaat acctgtgacg gaagatcact tcgcagaata aataaatcct | 60 |
| ggtgtccctg ttgataccgg gaagccctgg gccaacttttt ggcgaaaatg agacgttgat | 120 |
| cggcacgtaa gaggttccaa cttttcaccat aatgaaataa gatcactacc gggcgtattt | 180 |
| tttgagttat cgagatttttc aggagctaag gaagctaaaa tggagaaaaa aatcactgga | 240 |
| tataccaccg ttgatatatc ccaatggcat cgtaaagaac attttgaggc atttcagtca | 300 |
| gttgctcaat gtacctataa ccagaccgtt cagctggata ttacggcctt tttaaagacc | 360 |
| gtaaagaaaa ataagcacaa gttttatccg gcctttattc acattcttgc ccgcctgatg | 420 |
| aatgctcatc cggaattccg tatggcaatg aaagacggtg agctggtgat atgggatagt | 480 |
| gttcacccct tgttacaccgt tttccatgag caaactgaaa cgttttcatc gctctggagt | 540 |
| gaataccacg acgatttccg gcagtttcta cacatatatt cgcaagatgt ggcgtgttac | 600 |
| ggtgaaaacc tggcctattt ccctaaaggg tttattgaga atatgttttt cgtctcagcc | 660 |
| aatccctggg tgagtttcac cagttttgat ttaaacgtgg ccaatatgga caacttcttc | 720 |
| gccccccgttt tcaccatggg caaatattat acgcaaggcg acaaggtgct gatgccgctg | 780 |
| gcgattcagg ttcatcatgc cgtttgtgat ggcttccatg tcggcagaat gcttaatgaa | 840 |
| ttacaacagt actgcgatga gtggcagggc ggggcgtaat ttttttaagg cagttattgg | 900 |
| tgcccttaaa cgcctggttg ctacgcctga ataagtgata ataagcggat gaatggcaga | 960 |
| aattcgaaag caaattcgac ccggtcgtcg gttcagggca gggtcgttaa atagccgctt | 1020 |
| atgtctattg ctggtctcgg tacccgggga tcgcggccct atttctgacg ccgaagatcg | 1080 |
| tctgcaaggg tattacgatg cccttgctga aagtggtatt gcggccaatg accgctggt | 1140 |
| gacatttggc gaaccagacg aaagcggcgg cgaacaggca atgaccgagc ttttgggacg | 1200 |
| aggaagaaat ttcactgcgg tagcctgtta taacgattca atggcggcgg gtgcgatggg | 1260 |
| cgttctcaat gataatggta ttgatgtacc gggtgagatt tcgttaattg ctttgatga | 1320 |
| tgtgctggtg tcacgctatg tgcgtccgcg cctgaccacc gtgcgttacc caatcgtgac | 1380 |
| gatggcgacc caggctgccg aactggcttt ggcgctggcg ataatcgcc ctctcccgga | 1440 |
| aatcactaat gtctttagtc cgacgctggt acgtcgtcat tcagtgtcaa ctccgtcgct | 1500 |
| ggaggcaagt catcatgcaa ccagcgacta accgcagtta aagcaattcc agcgccagca | 1560 |
| taacaaactc cagataagtg cttttttatg attacgccac atcataaaaa gaataaaaaa | 1620 |
| tatcgattta tgtcgagtct atgcaaaaat gatatggatt accggattgc gagagagcgc | 1680 |
| taatggccgc cgttaactta cgtcatattg aaatttttca tgcggtaatg accgccggaa | 1740 |
| gcctgactga ggcggcacac ctgctacaca cctcacagcc aaccgtcagc cgcgaacttg | 1800 |
| cgcgctttga gaaggtgatc gggctgaaat tgtttgagcg cgtacgtggg cgattacatc | 1860 |
| ctaccgtgca aggactgcgt ctgtttgaag aagtgcaacg atcctggtac ggactggatc | 1920 |

-continued

```
gcattgtcag cgccgcagaa agtctgcgcg agtttcgcca gggagaactg tctattgcct    1980
gcctgccggt cttttcgcaa tcttttttac cgcagctcct gcaacccttt ctggcacgtt    2040
atcccgatgt cagcttaaat atcgtgcggc cgcgatcctc tagagtcgac cggtggcgaa    2100
tgggacgcgc cctgtagcgg cgcattaagc gcggcgggtg tggtggttac gcgcagcgtg    2160
accgctacac ttgccagcgc cctagcgccc gctcctttcg ctttcttccc ttcctttctc    2220
gccacgttcg ccggctttcc ccgtcaagct ctaaatcggg ggctcccttt agggttccga    2280
tttagtgctt tacggcacct cgaccccaaa aaacttgatt agggtgatgg ttcacgtagt    2340
gggccatcgc cctgatagac ggttttttcgc cctttgacgt tggagtccac gttctttaat    2400
agtggactct tgttccaaac tggaacaaca ctcaaccctat tctcggtcta ttcttttgat    2460
ttataaggga ttttgccgat tcggcctat tggttaaaaa atgagctgat ttaacaaaaa    2520
tttaacgcga attttaacaa atattaacg cttacaattt aggtggcact tttcggggaa    2580
atgtgcgcgg aacccctatt tgtttatttt tctaaataca ttcaaatatg tatccgctca    2640
ccgcgatcct ttttaaccca tcacatatac ctgccgttca ctattattta gtgaaatgag    2700
atattatgat attttctgaa ttgtgattaa aaaggcaact ttatgcccat gcaacagaaa    2760
ctataaaaaa tacagagaat gaaaagaaac agatagattt tttagttctt taggcccgta    2820
gtctgcaaat cctttatga ttttctatca aacaaaagag gaaaatagac cagttgcaat    2880
ccaaacgaga gtctaataga atgaggtcga aaagtaaatc gcgcgggttt gttactgata    2940
aagcaggcaa gacctaaaat gtgtaaaggg caaagtgtat actttggcgt caccccttac    3000
atatttagg tctttttta ttgtgcgtaa ctaacttgcc atcttcaaac aggagggctg    3060
gaagaagcag accgctaaca cagtacataa aaaggagac atgaacgatg aacatcaaaa    3120
agtttgcaaa acaagcaaca gtattaacct ttactaccgc actgctggca ggaggcgcaa    3180
ctcaagcgtt tgcgaaagaa acgaaccaaa agccatataa ggaaacatac ggcatttccc    3240
atattacacg ccatgatatg ctgcaaatcc ctgaacagca aaaaaatgaa aaatatcaag    3300
ttcctgagtt cgattcgtcc acaattaaaa atatctcttc tgcaaaaggc ctggacgttt    3360
gggacagctg gccattacaa aacgctgacg gcactgtcgc aaactatcac ggctaccaca    3420
tcgtctttgc attagccgga gatcctaaaa atgcggatga cacatcgatt tacatgttct    3480
atcaaaaagt cggcgaaact tctattgaca gctggaaaaa cgctggccgc gtctttaaag    3540
acagcgacaa attcgatgca aatgattcta tcctaaaaga ccaaacacaa gaatggtcag    3600
gttcagccac atttacatct gacgaaaaa tccgtttatt ctacactgat ttctccggta    3660
aacattacgg caaacaaaca ctgacaactg cacaagttaa cgtatcagca tcagacagct    3720
ctttgaacat caacggtgta gaggattata atcaatcttt tgacggtgac ggaaaaacgt    3780
atcaaaatgt acagcagttc atcgatgaag gcaactacag ctcaggcgac aaccatacgc    3840
tgagagatcc tcactacgta gaagataaag gccacaaata cttagtatt gaagcaaaca    3900
ctggaactga agatggctac caaggcgaag aatctttatt taacaaagca tactatggca    3960
aaagcacatc attcttccgt caagaaagtc aaaaacttct gcaaagcgat aaaaaacgca    4020
cggctgagtt agcaaacggc gctctcggta tgattgagct aaacgatgat tacacactga    4080
aaaaagtgat gaaccgctg attgcatcta acacagtaac agatgaaatt gaacgcgcga    4140
acgtctttaa aatgaacggc aaatggtacc tgttcactga ctcccgcgga tcaaaaatga    4200
cgattgacgg cattacgtct aacgatattt acatgcttgg ttatgtttct aattctttaa    4260
```

```
ctggcccata caagccgctg aacaaaactg gccttgtgtt aaaaatggat cttgatccta    4320
acgatgtaac ctttacttac tcacacttcg ctgtacctca agcgaaagga aacaatgtcg    4380
tgattacaag ctatatgaca acagaggat tctacgcaga caaacaatca acgtttgcgc    4440
caagcttcct gctgaacatc aaaggcaaga aaacatctgt tgtcaaagac agcatccttg    4500
aacaaggaca attaacagtt aacaaataaa aacgcaaaag aaaatgccga tattgactac    4560
cggaagcagt gtgaccgtgt gcttctcaaa tgcctgattc aggctgtcta tgtgtgactg    4620
ttgagctgta acaagttgtc tcaggtgttc aatttcatgt tctagttgct ttgttttact    4680
ggtttcacct gttctattag gtgttacatg ctgttcatct gttacattgt cgatctgttc    4740
atggtgaaca gctttaaatg caccaaaaac tcgtaaaagc tctgatgtat ctatcttttt    4800
tacaccgttt tcatctgtgc atatggacag ttttcccttt gatatgtaac ggtgaacagt    4860
tgttctactt ttgtttgtta gtcttgatgc ttcactgata gatacaagag ccataagaac    4920
ctcagatcct tccgtattta gccagtatgt tctctagtgt ggttcgttgt ttttgcgtga    4980
gccatgagaa cgaaccattg agatcatact tactttgcat gtcactcaaa aattttgcct    5040
caaaactggt gagctgaatt tttgcagtta aagcatcgtg tagtgttttt cttagtccgt    5100
tatgtaggta ggaatctgat gtaatggttg ttggtatttt gtcaccattc atttttatct    5160
ggttgttctc aagttcggtt acgagatcca tttgtctatc tagttcaact tggaaaatca    5220
acgtatcagt cgggcggcct cgcttatcaa ccaccaattt catattgctg taagtgttta    5280
aatctttact tattggtttc aaaacccatt ggttaagcct tttaaactca tggtagttat    5340
tttcaagcat taacatgaac ttaaattcat caaggctaat ctctatattt gccttgtgag    5400
ttttcttttg tgttagttct tttaataacc actcataaat cctcatagag tatttgtttt    5460
caaaagactt aacatgttcc agattatatt ttatgaattt ttttaactgg aaaagataag    5520
gcaatatctc ttcactaaaa actaattcta atttttcgct tgagaacttg gcatagtttg    5580
tccactggaa aatctcaaag cctttaaccc aaggattcct gatttccaca gttctcgtca    5640
tcagctctct ggttgcttta gctaatacac cataagcatt ttccctactg atgttcatca    5700
tctgaacgta ttggttataa gtgaacgata ccgtccgttc tttccttgta gggttttcaa    5760
tcgtggggtt gagtagtgcc acacagcata aaattagctt ggtttcatgc tccgttaagt    5820
catagcgact aatcgctagt tcatttgctt tgaaaacaac taattcagac atacatctca    5880
attggtctag gtgattttaa tcactatacc aattgagatg ggctagtcaa tgataattac    5940
tagtcctttt cctttgagtt gtgggtatct gtaaattctg ctagacccctt gctggaaaac    6000
ttgtaaattc tgctagaccc tctgtaaatt ccgctagacc tttgtgtgtt ttttttgttt    6060
atattcaagt ggttataatt tatagaataa agaaagaata aaaaaagata aaagaatag    6120
atcccagccc tgtgtataac tcactacttt agtcagttcc gcagtattac aaaaggatgt    6180
cgcaaacgct gtttgctcct ctacaaaaca gaccttaaaa ccctaaaggc ttaagtagca    6240
ccctcgcaag ctcgggcaaa tcgctgaata ttccttttgt ctccgaccat caggcacctg    6300
agtcgctgtc ttttcgtga cattcagttc gctgcgctca cggctctggc agtgaatggg    6360
ggtaaatggc actacaggcg ccttttatgg attcatgcaa ggaaactacc cataatacaa    6420
gaaaagcccg tcacgggctt ctcagggcgt tttatggcgg gtctgctatg tggtgctatc    6480
tgacttttg ctgttcagca gttcctgccc tctgattttc cagtctgacc acttcggatt    6540
atcccgtgac aggtcattca gactggctaa tgcacccagt aaggcagcgg tatcatcaac    6600
aggcttaccc gtcttactgt cggggatcga cgctctccct tatgcgactc ctgca         6655
```

<210> SEQ ID NO 13
<211> LENGTH: 6680
<212> TYPE: DNA
<213> ORGANISM: Artificial Sequence
<220> FEATURE:
<223> OTHER INFORMATION: with pKO3 derivative pGR-3-46

<400> SEQUENCE: 13

```
cctttcgtct tcgaataaat acctgtgacg gaagatcact tcgcagaata aataaatcct    60
ggtgtccctg ttgataccgg gaagccctgg gccaacttttt ggcgaaaatg agacgttgat   120
cggcacgtaa gaggttccaa ctttcaccat aatgaaataa gatcactacc gggcgtattt   180
tttgagttat cgagattttc aggagctaag gaagctaaaa tggagaaaaa aatcactgga   240
tataccaccg ttgatatatc ccaatggcat cgtaaagaac attttgaggc atttcagtca   300
gttgctcaat gtacctataa ccagaccgtt cagctggata ttacggcctt tttaaagacc   360
gtaaagaaaa ataagcacaa gttttatccg gcctttattc acattcttgc ccgcctgatg   420
aatgctcatc cggaattccg tatggcaatg aaagacggtg agctggtgat atgggatagt   480
gttcacccttgttacaccgt tttccatgag caaactgaaa cgttttcatc gctctggagt   540
gaataccacg acgatttccg gcagtttcta cacatatatt cgcaagatgt ggcgtgttac   600
ggtgaaaacc tggcctatttccctaaaggg tttattgaga atatgttttt cgtctcagcc   660
aatccctggg tgagtttcac cagttttgat ttaaacgtgg ccaatatgga caacttcttc   720
gcccccgttt tcaccatggg caaatattat acgcaaggcg acaaggtgct gatgccgctg   780
gcgattcagg ttcatcatgc cgtttgtgat ggcttccatg tcggcagaat gcttaatgaa   840
ttacaacagt actgcgatga gtggcagggc ggggcgtaat tttttttaagg cagttattgg   900
tgcccttaaa cgcctggttg ctacgcctga ataagtgata taagcggat gaatggcaga   960
aattcgaaag caaattcgac ccggtcgtcg gttcagggca gggtcgttaa atagccgctt  1020
atgtctattg ctggtctcgg tacccgggga tcgcggccgc ccaaccgcct gctcatttttg  1080
ctcattaacg ttggttgtca gttccggtgc catcgagagc gcatgctcca ccagcacccg  1140
acctacgccg cagccgcgca catcaggatc gataaacagc gcatccatat gctgcccact  1200
tagcaacata aatccaaccg gctgatcccg ctcattaacc gcgacccaca acggcgcttc  1260
cggcaggaag gaacgaacta ggtcctccag ctcggtccga tactctgctg atagaaaatc  1320
gtgagtggca tcgacagaac gacaccaaat cgcaacgagt tcctccccttcctcatgccg  1380
tgagcggcga atactaataa ccattttctc tccttttagt cattcttata ttctaacgta  1440
gtctttttcct tgaaactttc tcaccttcaa catgcaggct cgacattggc aaattttctg  1500
gttatcttca gctatctgga tgtctaaacg tataagcgta tgtagtgagg taatcaggtt  1560
atgctcgagg tgaatccaac gctggattaa tcttctgtga tagtcgatcg ttaagcgatt  1620
cagcaccttaccctcaggcac cttcgggtgc cttttttatt tccgaaacgt acctcagcag  1680
gtgaataaat tttattcata ttgttatcaa caagttatca agtattttta attaaaatgg  1740
aaattgtttt tgattttgca ttttaaatga gtagtcttag ttgtgctgaa cgaaaagagc  1800
acaacgatcc ttcgttcaca gtggggaagt tttcggatcc atgacgagga gctgcacgat  1860
gactgaacag gcaacaacaa ccgatgaact ggctttcaca aggccgtatg gcgagcagga  1920
gaagcaaatt cttactgccg aagcggtaga atttctgact gagctggtga cgcatttttac  1980
gccacaacgc aataaacttc tggcagcgcg cattcagcag cagcaagata ttgataacgg  2040
```

```
aacgttgcct gattttatttt cggaaacagc ttccattcgc gatgctgatt gcggccgcga    2100
tcctctagag tcgaccggtg gcgaatggga cgcgccctgt agcggcgcat taagcgcggc    2160
gggtgtggtg gttacgcgca gcgtgaccgc tacacttgcc agcgccctag cgcccgctcc    2220
tttcgctttc ttcccttcct ttctcgccac gttcgccggc tttccccgtc aagctctaaa    2280 tcggggctc cctttagggt tccgatttag tgctttacgg cacctcgacc ccaaaaaact    2340
tgattagggt gatggttcac gtagtgggcc atcgccctga tagacggttt ttcgcccttt    2400
gacgttggag tccacgttct ttaatagtgg actcttgttc caaactggaa caacactcaa    2460
ccctatctcg gtctattctt ttgatttata agggattttg ccgatttcgg cctattggtt    2520
aaaaaatgag ctgatttaac aaaaatttaa cgcgaatttt aacaaaatat taacgcttac    2580
aatttaggtg gcacttttcg gggaaatgtg cgcggaaccc ctatttgttt atttttctaa    2640
atacattcaa atatgtatcc gctcaccgcg atccttttta acccatcaca tatacctgcc    2700
gttcactatt atttagtgaa atgagatatt atgatatttt ctgaattgtg attaaaaagg    2760
caactttatg cccatgcaac agaaactata aaaaatacag agaatgaaaa gaaacagata    2820
gattttttag ttcttaggc ccgtagtctg caaatccttt tatgattttc tatcaaacaa    2880
aagaggaaaa tagaccagtt gcaatccaaa cgagagtcta atagaatgag gtcgaaaagt    2940
aaatcgcgcg ggtttgttac tgataaagca ggcaagacct aaaatgtgta aagggcaaag    3000
tgtatacttt ggcgtcaccc cttacatatt ttaggtcttt ttttattgtg cgtaactaac    3060
ttgccatctt caaacaggag ggctggaaga agcagaccgc taacacagta cataaaaaag    3120
gagacatgaa cgatgaacat caaaaagttt gcaaacaag caacagtatt aacctttact    3180
accgcactgc tggcaggagg cgcaactcaa gcgtttgcga agaaacgaa ccaaaagcca    3240 tataaggaaa catacggcat ttcccatatt acacgccatg atatgctgca aatccctgaa    3300
cagcaaaaaa atgaaaaata tcaagttcct gagttcgatt cgtccacaat taaaaatatc    3360
tcttctgcaa aaggcctgga cgtttgggac agctggccat tacaaaacgc tgacggcact    3420
gtcgcaaact atcacggcta ccacatcgtc tttgcattag ccggagatcc taaaaatgcg    3480
gatgacacat cgatttacat gttctatcaa aaagtcggcg aaacttctat tgacagctgg    3540
aaaaacgctg gccgcgtctt taaagacagc gacaaattcg atgcaaatga ttctatccta    3600
aaagaccaaa cacaagaatg gtcaggttca gccacattta catctgacgg aaaaatccgt    3660
ttattctaca ctgatttctc cggtaaacat tacggcaaac aaaacactgac aactgcacaa    3720 gttaacgtat cagcatcaga cagctctttg aacatcaacg gtgtagagga ttataaatca    3780
atctttgacg gtgacggaaa aacgtatcaa aatgtacagc agttcatcga tgaaggcaac    3840
tacagctcag gcgacaacca tacgctgaga gatcctcact acgtagaaga taaaggccac    3900
aaatacttag tatttgaagc aaacactgga actgaagatg gctaccaagg cgaagaatct    3960
ttatttaaca aagcatacta tggcaaaagc acatcattct tccgtcaaga aagtcaaaaa    4020
cttctgcaaa gcgataaaaa acgcacggct gagttagcaa acggcgctct cggtatgatt    4080
gagctaaacg atgattacac actgaaaaaa gtgatgaaac cgctgattgc atctaacaca    4140
gtaacagatg aaattgaacg cgcgaacgtc tttaaaatga acggcaaatg gtacctgttc    4200
actgactccc gcggatcaaa aatgacgatt gacggcatta cgtctaacga tatttacatg    4260
cttggttatg tttctaattc tttaactggc ccatacaagc cgctgaacaa actggccttt    4320
gtgttaaaaa tggatcttga tcctaacgat gtaacccttta cttactcaca cttcgctgta    4380
cctcaagcga aaggaaacaa tgtcgtgatt acaagctata tgacaaacag aggattctac    4440
```

```
gcagacaaac aatcaacgtt tgcgccaagc ttcctgctga acatcaaagg caagaaaaca      4500
tctgttgtca aagacagcat ccttgaacaa ggacaattaa cagttaacaa ataaaaacgc      4560
aaaagaaaat gccgatattg actaccggaa gcagtgtgac cgtgtgcttc tcaaatgcct      4620
gattcaggct gtctatgtgt gactgttgag ctgtaacaag ttgtctcagg tgttcaattt      4680
catgttctag ttgctttgtt ttactggttt cacctgttct attaggtgtt acatgctgtt      4740
catctgttac attgtcgatc tgttcatggt gaacagcttt aaatgcacca aaaactcgta      4800
aaagctctga tgtatctatc ttttttacac cgttttcatc tgtgcatatg gacagttttc      4860
cctttgatat gtaacggtga acagttgttc tacttttgtt tgttagtctt gatgcttcac      4920
tgatagatac aagagccata agaacctcag atccttccgt atttagccag tatgttctct      4980
agtgtggttc gttgttttg cgtgagccat gagaacgaac cattgagatc atacttactt      5040
tgcatgtcac tcaaaaattt tgcctcaaaa ctggtgagct gaattttgc agttaaagca      5100 tcgtgtagtg ttttcttag tccgttatgt aggtaggaat ctgatgtaat ggttgttggt      5160
attttgtcac cattcatttt tatctggttg ttctcaagtt cggttacgag atccatttgt      5220
ctatctagtt caacttggaa aatcaacgta tcagtcgggc ggcctcgctt atcaaccacc      5280
aatttcatat tgctgtaagt gtttaaatct ttacttattg gtttcaaaac ccattggtta      5340 agcctttaa actcatggta gttattttca agcattaaca tgaacttaaa ttcatcaagg      5400
ctaatctcta tatttgcctt gtgagttttc ttttgtgtta gttcttttaa taaccactca      5460
taaatcctca tagagtattt gttttcaaaa gacttaacat gttccagatt atattttatg      5520 aatttttta actggaaaag ataaggcaat atctcttcac taaaaactaa ttctaatttt      5580
tcgcttgaga acttggcata gtttgtccac tggaaaatct caaagccttt aaccaaagga      5640
ttcctgattt ccacagttct cgtcatcagc tctctggttg ctttagctaa tacaccataa      5700
gcattttccc tactgatgtt catcatctga acgtattggt tataagtgaa cgataccgtc      5760
cgttctttcc ttgtagggtt ttcaatcgtg gggttgagta gtgccacaca gcataaaatt      5820
agcttggttt catgctccgt taagtcatag cgactaatcg ctagttcatt tgctttgaaa      5880
acaactaatt cagacataca tctcaattgg tctaggtgat tttaatcact ataccaattg      5940
agatgggcta gtcaatgata attactagtc cttttccttt gagttgtggg tatctgtaaa      6000
ttctgctaga ccttttgctgg aaacttgta aattctgcta gaccctctgt aaattccgct      6060 agaccttgt gtgttttttt tgtttatatt caagtggtta taatttatag aataagaaa      6120 gaataaaaa agataaaaag aatagatccc agccctgtgt ataactcact actttagtca      6180
gttccgcagt attacaaaag gatgtcgcaa acgctgtttg ctcctctaca aaacagacct      6240
taaaacccta aaggcttaag tagcaccctc gcaagctcgg gcaaatcgct gaatattcct      6300
tttgtctccg accatcaggc acctgagtcg ctgtctttt cgtgacattc agttcgctgc      6360
gctcacggct ctggcagtga atgggggtaa atggcactac aggcgccttt tatggattca      6420
tgcaaggaaa ctacccataa tacaagaaaa gcccgtcacg ggcttctcag ggcgttttat      6480
ggcgggtctg ctatgtggtg ctatctgact ttttgctgtt cagcagttcc tgccctctga      6540
ttttccagtc tgaccacttc ggattatccc gtgacaggtc attcagactg gctaatgcac      6600
ccagtaaggc agcggtatca tcaacaggct tacccgtctt actgtcgggg atcgacgctc      6660
tcccttatgc gactcctgca                                                 6680
```

<210> SEQ ID NO 14

<211> LENGTH: 6665
<212> TYPE: DNA
<213> ORGANISM: Artificial Sequence
<220> FEATURE:
<223> OTHER INFORMATION: pKO3 derivative pJAG-4-47

<400> SEQUENCE: 14

```
cctttcgtct tcgaataaat acctgtgacg gaagatcact tcgcagaata aataaatcct      60
ggtgtccctg ttgataccgg gaagccctgg gccaacttttt ggcgaaaatg agacgttgat    120
cggcacgtaa gaggttccaa cttttcaccat aatgaaataa gatcactacc gggcgtattt    180
tttgagttat cgagattttc aggagctaag gaagctaaaa tggagaaaaa aatcactgga    240
tataccaccg ttgatatatc ccaatggcat cgtaaagaac attttgaggc atttcagtca    300
gttgctcaat gtacctataa ccagaccgtt cagctggata ttacggcctt tttaaagacc    360
gtaaagaaaa ataagcacaa gttttatccg gcctttattc acattcttgc ccgcctgatg    420
aatgctcatc cggaattccg tatggcaatg aaagacggtg agctggtgat atgggatagt    480
gttcacccctt gttacaccgt tttccatgag caaactgaaa cgttttcatc gctctggagt    540
gaataccacg acgatttccg gcagtttcta cacatatatt cgcaagatgt ggcgtgttac    600
ggtgaaaacc tggcctatttt ccctaaaggg tttattgaga atatgttttt cgtctcagcc    660
aatccctggg tgagtttcac cagttttgat ttaaacgtgg ccaatatgga caacttcttc    720
gccccccgttt tcaccatggg caaatattat acgcaaggcg acaaggtgct gatgccgctg    780
gcgattcagg ttcatcatgc cgtttgtgat ggcttccatg tcggcagaat gcttaatgaa    840
ttacaacagt actgcgatga gtggcagggc ggggcgtaat ttttttaagg cagttattgg    900
tgcccttaaa cgcctggttg ctacgcctga ataagtgata taagcggat gaatggcaga    960
aattcgaaag caaattcgac ccggtcgtcg gttcagggca gggtcgttaa atagccgctt   1020
atgtctattg ctggtctcgg tacccgggga tcgctcaccc agggatttat cggtagcgaa   1080
aataaaggtc gtacaacgac gcttggccgt ggaggcagcg attatacggc agccttgctg   1140
gcggaggctt tacacgcatc tcgtgttgat atctggaccg acgtcccggg catctacacc   1200
accgatccac gcgtagtttc cgcagcaaaa cgcattgatg aaatcgcgtt tgccgaagcg   1260
gcagagatgg caactttttgg tgcaaaagta ctgcatccgg caacgttgct acccgcagta   1320
cgcagcgata tcccggtctt tgtcggctcc agcaaagacc cacgcgcagg tggtacgctg   1380
gtgtgcaata aaactgaaaa tccgccgctg ttccgcgctc tggcgcttcg tcgcaatcag   1440
actctgctca ctttgcacag cctgaatatg ctgcattctc gcggtttcct cgcggaagtt   1500
ttcggcatcc tcgcgcggca taatatttcg gtagacttaa tcaccacgtc agaagtgagc   1560
gtggcattaa tccttgatac caccggttca acctccactg gcgatacgtt gctgacgcaa   1620
tctctgctga tggagctttc cgcactgtgt cgggtggagg tggaagaagg tctggcgctg   1680
gtcgcgttga ttggcaatga cctgtcaaaa gcctgcggcg ttggcaaaga ggtattcggc   1740
gtactggaac cgttcaacat cgcatgatt tgttatggcg catccagcca taacctgtgc   1800
ttcctggtgc ccggcgaaga tgccgagcag gtggtgcaaa aactgcatag taatttgttt   1860
gagtaaatac tgtatggcct ggaagctata tttcggccg tattgatttt cttgtcacta   1920
tgctcatcaa taaacgagcc tgtactctgt taaccagcgt ctttatcgga gaataattgc   1980
ctttaattttt tttatctgca tctctaatta attatcgaaa gagataaaata gttaagagaa   2040
ggcaaaatga atattatcag ttctgctcgc aaacgaattc cgcgatcctc tagagtcgac   2100
cggtggcgaa tgggacgcgc cctgtagcgg cgcattaagc gcggcgggtg tggtggttac   2160
```

```
gcgcagcgtg accgctacac ttgccagcgc cctagcgccc gctcctttcg ctttcttccc    2220
ttcctttctc gccacgttcg ccggcttcc ccgtcaagct ctaaatcggg ggctcccttt    2280
agggttccga tttagtgctt tacggcacct cgaccccaaa aaacttgatt agggtgatgg    2340
ttcacgtagt gggccatcgc cctgatagac ggtttttcgc cctttgacgt tggagtccac    2400
gttctttaat agtggactct tgttccaaac tggaacaaca ctcaacccta tctcggtcta    2460
ttcttttgat ttataaggga ttttgccgat ttcggcctat tggttaaaaa atgagctgat    2520
ttaacaaaaa tttaacgcga attttaacaa aatattaacg cttacaattt aggtggcact    2580
tttcggggaa atgtgcgcgg aacccctatt tgtttatttt tctaaataca ttcaaatatg    2640
tatccgctca ccgcgatcct ttttaaccca tcacatatac ctgccgttca ctattattta    2700
gtgaaatgag atattatgat attttctgaa ttgtgattaa aaaggcaact ttatgcccat    2760
gcaacagaaa ctataaaaaa tacagagaat gaaagaaac agatagattt tttagttctt    2820
taggcccgta gtctgcaaat ccttttatga ttttctatca aacaaagag gaaaatagac    2880 cagttgcaat ccaaacgaga gtctaataga atgaggtcga aaagtaaatc gcgcgggttt    2940
gttactgata aagcaggcaa gacctaaaat gtgtaaaggg caaagtgtat actttggcgt    3000
caccccttac atattttagg tcttttttta ttgtgcgtaa ctaacttgcc atcttcaaac    3060
aggagggctg gaagaagcag accgctaaca cagtacataa aaaaggagac atgaacgatg    3120
aacatcaaaa agtttgcaaa acaagcaaca gtattaacct ttactaccgc actgctggca    3180
ggaggcgcaa ctcaagcgtt tgcgaaagaa acgaaccaaa agccatataa ggaaacatac    3240
ggcatttccc atattacacg ccatgatatg ctgcaaatcc ctgaacagca aaaaaatgaa    3300
aaatatcaag ttcctgagtt cgattcgtcc acaattaaaa atatctcttc tgcaaaaggc    3360
ctggacgttt gggacagctg gccattacaa aacgctgacg gcactgtcgc aaactatcac    3420
ggctaccaca tcgtctttgc attagccgga gatcctaaaa atgcggatga cacatcgatt    3480
tacatgttct atcaaaaagt cggcgaaact tctattgaca gctggaaaaa cgctggccgc    3540
gtctttaaag acagcgacaa attcgatgca aatgattcta tcctaaaaga ccaaacacaa    3600
gaatggtcag gttcagccac atttacatct gacggaaaaa tccgtttatt ctacactgat    3660
ttctccggta acattacgg caaacaaaca ctgacaactg cacaagttaa cgtatcagca    3720
tcagacagct ctttgaacat caacggtgta gaggattata atcaatctt tgacggtgac    3780 ggaaaaacgt atcaaaatgt acagcagttc atcgatgaag gcaactacag ctcaggcgac    3840
aaccatacgc tgagagatcc tcactacgta gaagataaag gccacaaata cttagtattt    3900
gaagcaaaca ctggaactga agatggctac caaggcgaag aatctttatt taacaaagca    3960
tactatggca aaagcacatc attcttccgt caagaaagtc aaaaacttct gcaaagcgat    4020
aaaaaacgca cggctgagtt agcaaacggc gctctcggta tgattgagct aaacgatgat    4080
tacacactga aaaagtgat gaaaccgctg attgcatcta acacagtaac agatgaaatt    4140
gaacgcgcga acgtctttaa aatgaacggc aaatggtacc tgttcactga ctcccgcgga    4200
tcaaaaatga cgattgacgg cattacgtct aacgatattt acatgcttgg ttatgtttct    4260
aattctttaa ctggcccata caagccgctg aacaaaactg gccttgtgtt aaaaatggat    4320
cttgatccta acgatgtaac ctttacttac tcacacttcg ctgtacctca agcgaaagga    4380
aacaatgtcg tgattacaag ctatatgaca aacagaggat tctacgcaga caaacaatca    4440
acgtttgcgc caagcttcct gctgaacatc aaaggcaaga aacatctgt tgtcaaagac    4500
```

```
agcatccttg aacaaggaca attaacagtt aacaaataaa aacgcaaaag aaaatgccga    4560
tattgactac cggaagcagt gtgaccgtgt gcttctcaaa tgcctgattc aggctgtcta    4620
tgtgtgactg ttgagctgta acaagttgtc tcaggtgttc aatttcatgt tctagttgct    4680
ttgttttact ggtttcacct gttctattag gtgttacatg ctgttcatct gttacattgt    4740
cgatctgttc atggtgaaca gctttaaatg caccaaaaac tcgtaaaagc tctgatgtat    4800
ctatcttttt tacaccgttt tcatctgtgc atatggacag ttttcccttt gatatgtaac    4860
ggtgaacagt tgttctactt tgtttgtta gtcttgatgc ttcactgata gatacaagag     4920
ccataagaac ctcagatcct tccgtattta gccagtatgt tctctagtgt ggttcgttgt    4980
ttttgcgtga gccatgagaa cgaaccattg agatcatact tactttgcat gtcactcaaa    5040
aattttgcct caaaactggt gagctgaatt tttgcagtta agcatcgtg tagtgttttt      5100 cttagtccgt tatgtaggta ggaatctgat gtaatggttg ttggtatttt gtcaccattc    5160
atttttatct ggttgttctc aagttcggtt acgagatcca tttgtctatc tagttcaact    5220
tggaaaatca acgtatcagt cgggcggcct cgcttatcaa ccaccaattt catattgctg    5280
taagtgttta aatctttact tattggtttc aaaacccatt ggttaagcct tttaaactca    5340
tggtagttat tttcaagcat taacatgaac ttaaattcat caaggctaat ctctatattt    5400
gccttgtgag ttttcttttg tgttagttct tttaataacc actcataaat cctcatagag    5460
tatttgtttt caaaagactt aacatgttcc agattatatt ttatgaattt ttttaactgg    5520
aaaagataag gcaatatctc ttcactaaaa actaattcta attttttcgct tgagaacttg   5580 gcatagtttg tccactggaa aatctcaaag ccttttaacca aaggattcct gatttccaca   5640
gttctcgtca tcagctctct ggttgcttta gctaatacac cataagcatt ttccctactg    5700
atgttcatca tctgaacgta ttggttataa gtgaacgata ccgtccgttc tttccttgta    5760
gggttttcaa tcgtggggtt gagtagtgcc acacagcata aaattagctt ggtttcatgc    5820
tccgttaagt catagcgact aatcgctagt tcatttgctt tgaaaacaac taattcagac    5880
atacatctca attggtctag gtgattttaa tcactatacc aattgagatg ggctagtcaa    5940
tgataattac tagtccttttt cctttgagtt gtgggtatct gtaaattctg ctagacctttt  6000 gctggaaaac ttgtaaattc tgctagaccc tctgtaaatt ccgctagacc tttgtgtgtt    6060
ttttttgttt atattcaagt ggttataatt tatagaataa agaagaata aaaaagata      6120 aaagaatag atcccagccc tgtgtataac tcactacttt agtcagttcc gcagtattac     6180
aaaaggatgt cgcaaacgct gttttgctcct ctacaaaaca gaccttaaaa ccctaaaggc   6240
ttaagtagca ccctcgcaag ctcgggcaaa tcgctgaata ttccttttgt ctccgaccat    6300
caggcacctg agtcgctgtc ttttcgtga cattcagttc gctgcgctca cggctctggc     6360
agtgaatggg ggtaaatggc actacaggcg cctttatgg attcatgcaa ggaaactacc     6420
cataatacaa gaaaagcccg tcacgggctt ctcagggcgt tttatggcgg gtctgctatg    6480
tggtgctatc tgactttttg ctgttcagca gttcctgccc tctgattttc cagtctgacc    6540
acttcggatt atcccgtgac aggtcattca gactggctaa tgcacccagt aaggcagcgg    6600
tatcatcaac aggcttaccc gtcttactgt cggggatcga cgctctccct tatgcgactc    6660
ctgca                                                                6665
```

<210> SEQ ID NO 15
<211> LENGTH: 6686
<212> TYPE: DNA
<213> ORGANISM: Artificial Sequence
<220> FEATURE:
<223> OTHER INFORMATION: with pKO3 derivative 4-49

<400> SEQUENCE: 15

```
cctttcgtct tcgaataaat acctgtgacg gaagatcact tcgcagaata aataaatcct      60
ggtgtccctg ttgataccgg gaagccctgg gccaacttt ggcgaaaatg agacgttgat     120
cggcacgtaa gaggttccaa cttctcaccat aatgaaataa gatcactacc gggcgtattt     180
tttgagttat cgagattttc aggagctaag gaagctaaaa tggagaaaaa aatcactgga     240
tataccaccg ttgatatatc ccaatggcat cgtaaagaac attttgaggc atttcagtca     300
gttgctcaat gtacctataa ccagaccgtt cagctggata ttacggcctt tttaaagacc     360
gtaaagaaaa ataagcacaa gttttatccg cctttattc acattcttgc ccgcctgatg     420
aatgctcatc cggaattccg tatggcaatg aaagacggtg agctggtgat atgggatagt     480
gttcacccttt gttacaccgt tttccatgag caaactgaaa cgttttcatc gctctggagt     540
gaataccacg acgatttccg gcagtttcta cacatatatt cgcaagatgt ggcgtgttac     600
ggtgaaaacc tggcctattt ccctaaaggg tttattgaga atatgttttt cgtctcagcc     660
aatccctggg tgagtttcac cagttttgat ttaaacgtgg ccaatatgga caacttcttc     720
gccccgtttt tcaccatggg caaatattat acgcaaggcg acaaggtgct gatgccgctg     780
gcgattcagg ttcatcatgc cgtttgtgat ggcttccatg tcggcagaat gcttaatgaa     840
ttacaacagt actgcgatga gtggcagggc ggggcgtaat ttttttaagg cagttattgg     900
tgcccttaaa cgcctggttg ctacgcctga taagtgata taagcggat gaatggcaga     960
aattcgaaag caaattcgac ccggtcgtcg gttcagggca gggtcgttaa atagccgctt    1020
atgtctattg ctggtctcgg tacccgggga tcgccattcc ggctgatcac atggtgctga    1080
tggcaggttt caccgccggt aatgaaaaag gcgaactggt ggtgcttgga cgcaacggtt    1140
ccgactactc tgctgcggtg ctggctgcct gtttacgcgc cgattgttgc gagatttgga    1200
cggacgttga cggggtctat acctgcgacc cgcgtcaggt gcccgatgcg aggttgttga    1260
agtcgatgtc ctaccaggaa gcgatggagc tttcctactt cggcgctaaa gttcttcacc    1320
cccgcaccat taccccatc gcccagttcc agatcccttg cctgattaaa aataccggaa    1380
atcctcaagc accaggtacg ctcattggtg ccagccgtga tgaagacgaa ttaccggtca    1440
agggcatttc caatctgaat aacatggcaa tgttcagcgt ttctggtccg gggatgaaag    1500
ggatggtcgg catggcggcg cgcgtctttg cagcgatgtc acgcgcccgt attttcgtgg    1560
tgctgattac gcaatcatct tccgaataca gcatcagttt ctgcgttcca caaagcgact    1620
gtgtgcgagc tgaacgggca atgcaggaag agttctacct ggaactgaaa gaaggcttac    1680
tggagccgct ggcagtgacg gaacggctgg ccattatctc ggtggtaggt gatggtatgc    1740
gcaccttgcg tgggatctcg gcgaaattct ttgccgcact ggcccgcgcc aatatcaaca    1800
ttgtcgccat tgctcaggga tcttctgaac gctcaatctc tgtcgtggta aataacgatg    1860
atgcgaccac tggcgtgcgc gttactcatc agatgctgtt caataccgat caggttatcg    1920
aagtgtttgt gattggcgtc ggtggcgttg gcggtgcgct gctggagcaa ctgaagcgtc    1980
agcaaagctg gctgaagaat aaacatatcg acttacgtgt ctgcggtgtt gccaactcga    2040
aggctctgct caccaatgta catggcctta atctggaaaa ctggcaggaa gaactggcgc    2100
aagcgatcct ctagagtcga ccggtggcga atgggacgcg ccctgtagcg gcgcattaag    2160
cgcggcgggt gtggtggtta cgcgcagcgt gaccgctaca cttgccagcg ccctagcgcc    2220
```

-continued

```
cgctcctttc gctttcttcc cttcctttct cgccacgttc gccggctttc cccgtcaagc    2280
tctaaatcgg gggctcccct tagggttccg atttagtgct ttacggcacc tcgaccccaa    2340
aaaacttgat tagggtgatg gttcacgtag tgggccatcg ccctgataga cggttttcg     2400 cccttgacg ttggagtcca cgttctttaa tagtggactc ttgttccaaa ctggaacaac    2460
actcaaccct atctcggtct attcttttga tttataaggg attttgccga tttcggccta    2520
ttggttaaaa aatgagctga tttaacaaaa attttaacgcg aattttaaca aaatattaac   2580
gcttacaatt taggtggcac ttttcgggga aatgtgcgcg gaaccccctat ttgtttattt   2640 ttctaaatac attcaaatat gtatccgctc accgcgatcc ttttaaccc atcacatata    2700 cctgccgttc actattattt agtgaaatga gatattatga tattttctga attgtgatta   2760
aaaaggcaac tttatgccca tgcaacagaa actataaaaa atacagagaa tgaaaagaaa   2820
cagatagatt ttttagttct ttaggcccgt agtctgcaaa tccttttatg attttctatc   2880
aaacaaaaga ggaaaataga ccagttgcaa tccaaacgag agtctaatag aatgaggtcg   2940
aaaagtaaat cgcgcgggtt tgttactgat aaagcaggca agacctaaaa tgtgtaaagg   3000
gcaaagtgta tactttggcg tcacccctta catattttag gtcttttttt attgtgcgta   3060
actaacttgc catcttcaaa caggagggct ggaagaagca gaccgctaac acagtacata   3120
aaaaaggaga catgaacgat gaacatcaaa aagtttgcaa aacaagcaac agtattaacc   3180
tttactaccg cactgctggc aggaggcgca actcaagcgt tgcgaaaga acgaaccaa    3240 aagccatata aggaaacata cggcatttcc catattacac gccatgatat gctgcaaatc   3300
cctgaacagc aaaaaaatga aaatatcaa gttcctgagt tcgattcgtc cacaattaaa    3360
aatatctctt ctgcaaaagg cctggacgtt tgggacagct ggccattaca aaacgctgac   3420
ggcactgtcg caaactatca cggctaccac atcgtctttg cattagccgg agatcctaaa   3480
aatgcggatg acacatcgat ttacatgttc tatcaaaaag tcggcgaaac ttctattgac   3540
agctggaaaa acgctggccg cgtctttaaa gacagcgaca aattcgatgc aaatgattct   3600
atcctaaaag accaaacaca agaatggtca ggttcagcca catttacatc tgacggaaaa   3660
atccgtttat tctacactga tttctccggt aaacattacg gcaaacaaac actgacaact   3720
gcacaagtta acgtatcagc atcagacagc tctttgaaca tcaacggtgt agaggattat   3780
aaatcaatct tgacggtga cggaaaaacg tatcaaaatg tacagcagtt catcgatgaa   3840
ggcaactaca gctcaggcga caaccatacg ctgagagatc ctcactacgt agaagataaa   3900
ggccacaaat acttagtatt tgaagcaaac actggaactg aagatggcta ccaaggcgaa   3960
gaatctttat ttaacaaagc atactatggc aaaagcacat cattcttccg tcaagaaagt   4020
caaaaacttc tgcaaagcga taaaaaacgc acggctgagt tagcaaacgg cgctctcggt   4080
atgattgagc taaacgatga ttacacactg aaaaaagtga tgaaaccgct gattgcatct   4140
aacacagtaa cagatgaaat tgaacgcgcg aacgtcttta aaatgaacgg caaatggtac   4200
ctgttcactg actcccgcgg atcaaaaatg acgattgacg gcattacgtc taacgatatt   4260
tacatgcttg gttatgtttc taattctttta actggcccat acaagccgct gaacaaaact   4320
ggccttgtgt taaaaatgga tcttgatcct aacgatgtaa cctttactta ctcacacttc   4380
gctgtacctc aagcgaaagg aaacaatgtc gtgattacaa gctatatgac aaacagagga   4440
ttctacgcag acaaacaatc aacgtttgcg ccaagcttcc tgctgaacat caaaggcaag   4500
aaaacatctg ttgtcaaaga cagcatcctt gaacaaggca aattaacagt taacaaataa   4560
aaacgcaaaa gaaaatgccg atattgacta ccggaagcag tgtgaccgtg tgcttctcaa   4620
```

```
atgcctgatt caggctgtct atgtgtgact gttgagctgt aacaagttgt ctcaggtgtt    4680
caatttcatg ttctagttgc tttgttttac tggtttcacc tgttctatta ggtgttacat    4740
gctgttcatc tgttacattg tcgatctgtt catggtgaac agctttaaat gcaccaaaaa    4800
ctcgtaaaag ctctgatgta tctatctttt ttacaccgtt ttcatctgtg catatggaca    4860
gttttccctt tgatatgtaa cggtgaacag ttgttctact tttgtttgtt agtcttgatg    4920
cttcactgat agatacaaga gccataagaa cctcagatcc ttccgtattt agccagtatg    4980
ttctctagtg tggttcgttg tttttgcgtg agccatgaga acgaaccatt gagatcatac    5040
ttactttgca tgtcactcaa aaattttgcc tcaaaactgg tgagctgaat ttttgcagtt    5100
aaagcatcgt gtagtgtttt tcttagtccg ttatgtaggt aggaatctga tgtaatggtt    5160
gttggtattt tgtcaccatt cattttatc tggttgttct caagttcggt tacgagatcc    5220
atttgtctat ctagttcaac ttggaaaatc aacgtatcag tcgggcggcc tcgcttatca    5280
accaccaatt tcatattgct gtaagtgttt aaatctttac ttattggttt caaaacccat    5340
tggttaagcc ttttaaactc atggtagtta ttttcaagca ttaacatgaa cttaaattca    5400
tcaaggctaa tctctatatt tgccttgtga gttttctttt gtgttagttc ttttaataac    5460
cactcataaa tcctcataga gtatttgttt tcaaaagact taacatgttc cagattatat    5520
tttatgaatt ttttaactg gaaaagataa ggcaatatct cttcactaaa aactaattct    5580 aattttttcgc ttgagaactt ggcatagttt gtccactgga aaatctcaaa gcctttaacc    5640
aaaggattcc tgatttccac agttctcgtc atcagctctc tggttgcttt agctaataca    5700
ccataagcat tttccctact gatgttcatc atctgaacgt attggttata agtgaacgat    5760
accgtccgtt ctttccttgt agggttttca atcgtggggt tgagtagtgc cacacagcat    5820
aaaattagct tggtttcatg ctccgttaag tcatagcgac taatcgctag ttcatttgct    5880
ttgaaaacaa ctaattcaga catacatctc aattggtcta ggtgatttta atcactatac    5940
caattgagat gggctagtca atgataatta ctagtccttt tcctttgagt tgtgggtatc    6000
tgtaaattct gctagacctt tgctggaaaa cttgtaaatt ctgctagacc ctctgtaaat    6060
tccgctagac ctttgtgtgt ttttttttgtt tatattcaag tggttataat ttatagaata    6120
aagaaagaat aaaaaaagat aaaaagaata gatcccagcc ctgtgtataa ctcactactt    6180
tagtcagttc cgcagtatta caaaggatg tcgcaaacgc tgtttgctcc tctacaaaac    6240
agaccttaaa accctaaagg cttaagtagc accctcgcaa gctcgggcaa atcgctgaat    6300
attccttttg tctccgacca tcaggcacct gagtcgctgt cttttttcgtg acattcagtt    6360 cgctgcgctc acggctctgg cagtgaatgg gggtaaatgg cactacaggc gccttttatg    6420
gattcatgca aggaaactac ccataataca agaaaagccc gtcacgggct ctcagggcg    6480 ttttatggcg ggtctgctat gtggtgctat ctgactttt gctgttcagc agttcctgcc    6540
ctctgatttt ccagtctgac cacttcggat tatcccgtga caggtcattc agactggcta    6600
atgcacccag taaggcagcg gtatcatcaa caggcttacc cgtcttactg tcggggatcg    6660
acgctctccc ttatgcgact cctgca                                          6686
```

<210> SEQ ID NO 16
<211> LENGTH: 50
<212> TYPE: DNA
<213> ORGANISM: Artificial Sequence
<220> FEATURE:
<223> OTHER INFORMATION: primer_metA_up_fp

<400> SEQUENCE: 16
ctggtctcgg tacccgggga tcgcggccgc ccaaccgcct gctcattttg    50

<210> SEQ ID NO 17
<211> LENGTH: 45
<212> TYPE: DNA
<213> ORGANISM: Artificial Sequence
<220> FEATURE:
<223> OTHER INFORMATION: primer_metA_up_rp

<400> SEQUENCE: 17
gcgttggatt cacctcgagc ataacctgat tacctcacta catac    45

<210> SEQ ID NO 18
<211> LENGTH: 36
<212> TYPE: DNA
<213> ORGANISM: Artificial Sequence
<220> FEATURE:
<223> OTHER INFORMATION: primer_metA_down_fp

<400> SEQUENCE: 18
tatgctcgag gtgaatccaa cgctggatta atcttc    36

<210> SEQ ID NO 19
<211> LENGTH: 54
<212> TYPE: DNA
<213> ORGANISM: Artificial Sequence
<220> FEATURE:
<223> OTHER INFORMATION: primer_metA_up_rp

<400> SEQUENCE: 19
cgccaccggt cgactctaga ggatcgcggc cgcaatcagc atcgcgaatg gaag    54

<210> SEQ ID NO 20
<211> LENGTH: 42
<212> TYPE: DNA
<213> ORGANISM: Artificial Sequence
<220> FEATURE:
<223> OTHER INFORMATION: primer_MW_15_62_fw

<400> SEQUENCE: 20
tctcggtacc cggggatcgc tttaagctga catcgggata ac    42

<210> SEQ ID NO 21
<211> LENGTH: 32
<212> TYPE: DNA
<213> ORGANISM: Artificial Sequence
<220> FEATURE:
<223> OTHER INFORMATION: primer_MW_15_63_rv

<400> SEQUENCE: 21
cataacaaac tccagataag tgcttttta tg    32

<210> SEQ ID NO 22
<211> LENGTH: 50
<212> TYPE: DNA
<213> ORGANISM: Artificial Sequence
<220> FEATURE:
<223> OTHER INFORMATION: primer_MW_15_64_fw

<400> SEQUENCE: 22
cttatctgga gtttgttatg ctcgaggaat tgctttaact gcggttagtc    50

<210> SEQ ID NO 23
<211> LENGTH: 42

<210> SEQ ID NO 23
<211> LENGTH: 42
<212> TYPE: DNA
<213> ORGANISM: Artificial Sequence
<220> FEATURE:
<223> OTHER INFORMATION: primer_MW_15_65_rv

<400> SEQUENCE: 23
ggtcgactct agaggatcgc atacccgcat tggttatctg tg                42

<210> SEQ ID NO 24
<211> LENGTH: 42
<212> TYPE: DNA
<213> ORGANISM: Artificial Sequence
<220> FEATURE:
<223> OTHER INFORMATION: primer_MW_15_66_fw

<400> SEQUENCE: 24
tctcggtacc cggggatcgc tcacccaggg atttatcggt ag                42

<210> SEQ ID NO 25
<211> LENGTH: 22
<212> TYPE: DNA
<213> ORGANISM: Artificial Sequence
<220> FEATURE:
<223> OTHER INFORMATION: primer_MW_15_67_rv

<400> SEQUENCE: 25
caaggattaa tgccacgctc ac                                      22

<210> SEQ ID NO 26
<211> LENGTH: 22
<212> TYPE: DNA
<213> ORGANISM: Artificial Sequence
<220> FEATURE:
<223> OTHER INFORMATION: primer_MW_15_68_fw

<400> SEQUENCE: 26
gtgagcgtgg cattaatcct tg                                      22

<210> SEQ ID NO 27
<211> LENGTH: 42
<212> TYPE: DNA
<213> ORGANISM: Artificial Sequence
<220> FEATURE:
<223> OTHER INFORMATION: primer_MW_15_69_rv

<400> SEQUENCE: 27
ggtcgactct agaggatcgc ggaattcgtt tgcgagcaga ac                42

<210> SEQ ID NO 28
<211> LENGTH: 45
<212> TYPE: DNA
<213> ORGANISM: Artificial Sequence
<220> FEATURE:
<223> OTHER INFORMATION: primer_JC-15-009_fw

<400> SEQUENCE: 28
gctggtctcg gtacccgggg atcgccattc ggctgatca catgg              45

<210> SEQ ID NO 29
<211> LENGTH: 25
<212> TYPE: DNA
<213> ORGANISM: Artificial Sequence
<220> FEATURE:
<223> OTHER INFORMATION: primer_JC-15-006_rv

<400> SEQUENCE: 29

```
gtaatcagca ccacgaaaat acggg                                            25

<210> SEQ ID NO 30
<211> LENGTH: 25
<212> TYPE: DNA
<213> ORGANISM: Artificial Sequence
<220> FEATURE:
<223> OTHER INFORMATION: primer_JC-15-007_fw

<400> SEQUENCE: 30 cccgtattt cgtggtgctg attac                                             25

<210> SEQ ID NO 31
<211> LENGTH: 45
<212> TYPE: DNA
<213> ORGANISM: Artificial Sequence
<220> FEATURE:
<223> OTHER INFORMATION: primer_JC-15-010_rv

<400> SEQUENCE: 31
ccaccggtcg actctagagg atcgcttgcg ccagttcttc ctgcc                      45

<210> SEQ ID NO 32
<211> LENGTH: 167
<212> TYPE: DNA
<213> ORGANISM: Artificial Sequence
<220> FEATURE:
<223> OTHER INFORMATION: tac promoter

<400> SEQUENCE: 32
ggatccaatt gtgagcggat aacaattacg agcttcatgc acagtgatcg acgctgttga      60
caattaatca tcggctcgta taatgtgtgg atgtggaatt gtgagcgctc acaattccac     120
aacggtttcc ctctagaaat aattttgttt aacaggaggt aaaacat                   167

<210> SEQ ID NO 33
<211> LENGTH: 45
<212> TYPE: DNA
<213> ORGANISM: Artificial Sequence
<220> FEATURE:
<223> OTHER INFORMATION: primer_JC-15-001

<400> SEQUENCE: 33
ggatctagga accaaggaga gtggcatgcc caccctcgcg ccttc                      45

<210> SEQ ID NO 34
<211> LENGTH: 34
<212> TYPE: DNA
<213> ORGANISM: Artificial Sequence
<220> FEATURE:
<223> OTHER INFORMATION: primer_JC-15-002

<400> SEQUENCE: 34
caattggatc cgtttatccg gagggttgcc tgtg                                  34

<210> SEQ ID NO 35
<211> LENGTH: 38
<212> TYPE: DNA
<213> ORGANISM: Artificial Sequence
<220> FEATURE:
<223> OTHER INFORMATION: primer_JC-15-003

<400> SEQUENCE: 35
accctccgga taaacggatc caattgtgag cggataac                              38
```

```
<210> SEQ ID NO 36
<211> LENGTH: 31
<212> TYPE: DNA
<213> ORGANISM: Artificial Sequence
<220> FEATURE:
<223> OTHER INFORMATION: primer_JC-15-004

<400> SEQUENCE: 36
acactcgcat atgttttacc tcctgttaaa c                              31

<210> SEQ ID NO 37
<211> LENGTH: 35
<212> TYPE: DNA
<213> ORGANISM: Artificial Sequence
<220> FEATURE:
<223> OTHER INFORMATION: primer_JC-15-005

<400> SEQUENCE: 37
caggaggtaa aacatatgcg agtgttgaag ttcgg                          35

<210> SEQ ID NO 38
<211> LENGTH: 25
<212> TYPE: DNA
<213> ORGANISM: Artificial Sequence
<220> FEATURE:
<223> OTHER INFORMATION: primer_JC-15-006

<400> SEQUENCE: 38
gtaatcagca ccacgaaaat acggg                                     25

<210> SEQ ID NO 39
<211> LENGTH: 25
<212> TYPE: DNA
<213> ORGANISM: Artificial Sequence
<220> FEATURE:
<223> OTHER INFORMATION: primer_JC-15-007

<400> SEQUENCE: 39
cccgtatttt cgtggtgctg attac                                     25

<210> SEQ ID NO 40
<211> LENGTH: 50
<212> TYPE: DNA
<213> ORGANISM: Artificial Sequence
<220> FEATURE:
<223> OTHER INFORMATION: primer_JC-15-008

<400> SEQUENCE: 40
ggtgcgccag gagagttgtt gatttatcag actcctaact tccatgagag          50

<210> SEQ ID NO 41
<211> LENGTH: 4347
<212> TYPE: DNA
<213> ORGANISM: Artificial Sequence
<220> FEATURE:
<223> OTHER INFORMATION: pJ281_Placuv5

<400> SEQUENCE: 41
gtataggaac ttctgaagtg gggggatccg gccggcccaa aaaggccggg aaatacccag    60
cctcgctttg taacggagta gagacgaaag tgattgcgcc tacccggata ttatcgtgag   120
gatgcgtcat cgccattaat tcactgatca gtgataagct gtcaaacatg agaattaatt   180
ccggcgatcc gtcgacttgc agcaattccc gaggctgtag ccgacgatgg tgcgccagga   240
gagttgttga tctagactga gtcaatggca tatgccactc tccttggttc ctagatcctg   300
```

```
tgtgaaattg ttattgttat ccgctcacaa ttccacacat tatacgagcc ggaagcataa    360
agtgtcaagc ctggggtgcc taatgagtga gctaacttac attaattgcg ttgcgctcac    420
tgcccgcata tctatgagcc gggctgaatg atcgaccgag acaggccctg cggggctgca    480
ggccggccgg atccaaaatg aagtgaagtt cctatactta ctagagaata ggaacttcta    540
tagtgagtcg aataagggcg acacaaaatt tattctaaat gcataataaa tactgataac    600
atcttatagt ttgtattata ttttgtatta tcgttgacat gtaattttt gatatcaaaa     660 actgattttc cctttattat tttcgagatt tattttctta attctcttta acaaactaga    720
aatattgtat atacaaaaaa tcataaataa tagatgaata gtttaattat aggtgttcat    780
caatcgaaaa agcaacgtat cttatttaaa gtgcgttgct tttttctcat ttataaggtt    840
aaataattct catatatcaa gcaaagtgac aggcgccctt aaatattctg acaaatgctc    900
tttccctaaa ctccccccat aaaaaaaccc gccgaagcgg ttttttacgt tatttgcgga    960
ttaacgatta ctcgttatca gaaccgccca ggggcccga gcttaagact ggccgtcgtt    1020
ttacaacaca gaaagagttt gtagaaacgc aaaaaggcca tccgtcaggg gccttctgct    1080
tagtttgatg cctggcagtt ccctactctc gccttccgct tcctcgctca ctgactcgct    1140
gcgctcggtc gttcggctgc ggcgagcggt atcagctcac tcaaaggcgg taatacggtt    1200
atccacagaa tcaggggata acgcaggaaa gaacatgtga gcaaaaggcc agcaaaaggc    1260
caggaaccgt aaaaaggccg cgttgctggc gttttccat aggctccgcc ccctgacga     1320 gcatcacaaa aatcgacgct caagtcagag gtggcgaaac ccgacaggac tataaagata    1380
ccaggcgttt ccccctggaa gctccctcgt gcgctctcct gttccgaccc tgccgcttac    1440
cggatacctg tccgcctttc tcccttcggg aagcgtggcg ctttctcata gctcacgctg    1500
taggtatctc agttcggtgt aggtcgttcg ctccaagctg ggctgtgtgc acgaaccccc    1560
cgttcagccc gaccgctgcg ccttatccgg taactatcgt cttgagtcca acccggtaag    1620
acacgactta tcgccactgg cagcagccac tggtaacagg attagcagag cgaggtatgt    1680
aggcggtgct acagagttct tgaagtggtg gcctaactac ggctacacta agaacagt     1740 atttggtatc tgcgctctgc tgaagccagt taccttcgga aaaagagttg gtagctcttg    1800
atccggcaaa caaaccaccg ctggtagcgg tggtttttt gtttgcaagc agcagattac    1860
gcgcagaaaa aaggatctc aagaagatcc tttgatcttt tctacggggt ctgacgctca    1920
gtggaacgac gcgcgcgtaa ctcacgttaa gggattttgg tcatgagtca ctgcccgctt    1980
tccagtcggg aaacctgtcg tgccagctgc attaatgaat cggccaacgc gcggggagag    2040
gcggtttgcg tattgggcgc cagggtggtt tttcttttca ccagtgagac tggcaacagc    2100
tgattgccct tcaccgcctg gccctgagag agttgcagca agcggtccac gctggtttgc    2160
cccagcaggc gaaaatcctg tttgatggtg gttaacggcg ggatataaca tgagctatct    2220
tcggtatcgt cgtatcccac taccgagata tccgcaccaa cgcgcagccc ggactcggta    2280
atggcgcgca ttgcgcccag cgccatctga tcgttgcaa ccagcatcgc agtgggaacg    2340
atgccctcat tcagcatttg catggttgt tgaaaccgg acatggcact ccagtcgcct     2400
tcccgttccg ctatcggctg aatttgattg cgagtgagat atttatgcca gccagccaga    2460
cgcagacgcg ccgagacaga acttaatggg cccgctaaca gcgcgatttg ctggtgaccc    2520
aatgcgacca gatgctccac gcccagtcgc gtaccgtcct catgggagaa aataatactg    2580
ttgatgggtg tctggtcaga gacatcaaga aataacgccg aacattagt gcaggcagct     2640 tccacagcaa tggcatcctg gtcatccagc ggatagttaa tgatcagccc actgacgcgt    2700
```

```
tgcgcgagaa gattgtgcac cgccgcttta caggcttcga cgccgcttcg ttctaccatc   2760
gacaccacca cgctggcacc cagttgatcg gcgcgagatt taatcgccgc gacaatttgc   2820
gacggcgcgt gcagggccag actggaggtg gcaacgccaa tcagcaacga ctgtttgccc   2880
gccagttgtt gtgccacgcg gttgggaatg taattcagct ccgccatcgc cgcttccact   2940 tttcccgcg ttttcgcaga aacgtggctg gcctggttca ccacgcggga acggtctga    3000 taagagacac cggcatactc tgcgacatcg tataacgtta ctggtttcat attcaccacc   3060
ctgaattgac tctcttccgg gcgctatcat gccataccgc gaaaggtttt gcgccattcg   3120
atggcgcgcc gcttttagaa aaactcatcg agcatcaaat gaaactgcaa tttattcata   3180
tcaggattat caataccata tttttgaaaa agccgtttct gtaatgaagg agaaaactca   3240
ccgaggcagt tccataggat ggcaagatcc tggtatcggt ctgcgattcc gactcgtcca   3300
acatcaatac aacctattaa tttcccctcg tcaaaaataa ggttatcaag tgagaaatca   3360
ccatgagtga cgactgaatc cggtgagaat ggcaaaagtt tatgcatttc tttccagact   3420
tgttcaacag gccagccatt acgctcgtca tcaaaatcac tcgcatcaac caaaccgtta   3480
ttcattcgtg attgcgcctg agcgaggcga atacgcgat cgctgttaaa aggacaatta   3540
caaacaggaa tcgagtgcaa ccggcgcagg aacactgcca gcgcatcaac aatattttca   3600
cctgaatcag gatattcttc taatacctgg aacgctgttt ttccggggat cgcagtggtg   3660
agtaaccatg catcatcagg agtacggata aaatgcttga tggtcggaag tggcataaat   3720
tccgtcagcc agtttagtct gaccatctca tctgtaacat cattggcaac gctacctttg   3780
ccatgtttca gaaacaactc tggcgcatcg ggcttcccat acaagcgata gattgtcgca   3840
cctgattgcc cgacattatc gcgagcccat ttatacccat ataaatcagc atccatgttg   3900
gaatttaatc gcggcctcga cgtttcccgt tgaatatggc tcatattctt cctttttcaa   3960
tattattgaa gcatttatca gggttattgt ctcatgagcg gatacatatt tgaatgtatt   4020
tagaaaaata aacaaatagg ggtcagtgtt acaaccaatt aaccaattct gaacattatc   4080
gcgagcccat ttatacctga atatggctca taacacccct tgtttgcctg gcggcagtag   4140
cgcggtggtc ccacctgacc ccatgccgaa ctcagaagtg aaacgccgta cgccgatgg    4200 tagtgtgggg actccccatg cgagagtagg gaactgccag gcatcaaata aaacgaaagg   4260
ctcagtcgaa agactgggcc tttcgcccgg gctaattagg gggtgtcgcc cttattcgac   4320
tctatagtga agttcctatt ctctagt                                      4347
```

<210> SEQ ID NO 42
<211> LENGTH: 8155
<212> TYPE: DNA
<213> ORGANISM: Artificial Sequence
<220> FEATURE:
<223> OTHER INFORMATION: pJAG-4-48

<400> SEQUENCE: 42

```
actagagaat aggaacttca ctatagagtc gaataagggc gacacccct aattagcccg     60 ggcgaaaggc ccagtctttc gactgagcct ttcgttttat ttgatgcctg gcagttccct   120
actctcgcat ggggagtccc cacactacca tcggcgctac ggcgtttcac ttctgagttc   180
ggcatggggt caggtgggac caccgcgcta ctgccgccag gcaaacaagg ggtgttatga   240
gccatattca ggtataaatg ggctcgcgat aatgttcaga attggttaat tggttgtaac   300 actgaccct atttgtttat ttttctaaat acattcaaat atgtatccgc tcatgagaca   360
```

-continued

| | |
|---|---|
| ataaccctga taaatgcttc aataatattg aaaaggaag aatatgagcc atattcaacg | 420 |
| ggaaacgtcg aggccgcgat taaattccaa catggatgct gatttatatg ggtataaatg | 480 |
| ggctcgcgat aatgtcgggc aatcaggtgc gacaatctat cgcttgtatg ggaagcccga | 540 |
| tgcgccagag ttgtttctga acatggcaa aggtagcgtt gccaatgatg ttacagatga | 600 |
| gatggtcaga ctaaactggc tgacggaatt tatgccactt ccgaccatca agcattttat | 660 |
| ccgtactcct gatgatgcat ggttactcac cactgcgatc cccggaaaaa cagcgttcca | 720 |
| ggtattagaa gaatatcctg attcaggtga aaatattgtt gatgcgctgg cagtgttcct | 780 |
| gcgccggttg cactcgattc ctgtttgtaa ttgtcctttt aacagcgatc gcgtatttcg | 840 |
| cctcgctcag gcgcaatcac gaatgaataa cggtttggtt gatgcgagtg attttgatga | 900 |
| cgagcgtaat ggctggcctg ttgaacaagt ctggaaagaa atgcataaac ttttgccatt | 960 |
| ctcaccggat tcagtcgtca ctcatggtga tttctcactt gataaccttat tttttgacga | 1020 |
| ggggaaatta ataggttgta ttgatgttgg acgagtcgga atcgcagacc gataccagga | 1080 |
| tcttgccatc ctatggaact gcctcggtga gttttctcct tcattacaga aacggctttt | 1140 |
| tcaaaaatat ggtattgata atcctgatat gaataaattg cagtttcatt tgatgctcga | 1200 |
| tgagtttttc taaaagcggc gcgccatcga atggcgcaaa accttcgcg gtatggcatg | 1260 |
| atagcgcccg gaagagagtc aattcagggt ggtgaatatg aaaccagtaa cgttatacga | 1320 |
| tgtcgcagag tatgccggtg tctcttatca gaccgtttcc cgcgtggtga accaggccag | 1380 |
| ccacgtttct gcgaaaacgc gggaaaaagt ggaagcggcg atggcggagc tgaattacat | 1440 |
| tcccaaccgc gtggcacaac aactggcggg caaacagtcg ttgctgattg gcgttgccac | 1500 |
| ctccagtctg gccctgcacg cgccgtcgca aattgtcgcg gcgattaaat ctcgcgccga | 1560 |
| tcaactgggt gccagcgtgg tggtgtcgat ggtagaacga agcggcgtcg aagcctgtaa | 1620 |
| agcggcggtg cacaatcttc tcgcgcaacg cgtcagtggg ctgatcatta actatccgct | 1680 |
| ggatgaccag gatgccattg ctgtggaagc tgcctgcact aatgttccgg cgttatttct | 1740 |
| tgatgtctct gaccagacac ccatcaacag tattattttc tcccatgagg acggtacgcg | 1800 |
| actgggcgtg gagcatctgg tcgcattggg tcaccagcaa atcgcgctgt tagcgggccc | 1860 |
| attaagttct gtctcggcgc gtctgcgtct ggctggctgg cataaatatc tcactcgcaa | 1920 |
| tcaaattcag ccgatagcgg aacgggaagg cgactgagt gccatgtccg gttttcaaca | 1980 |
| aaccatgcaa atgctgaatg agggcatcgt tcccactgcg atgctggttg ccaacgatca | 2040 |
| gatggcgctg ggcgcaatgc gcgccattac cgagtccggg ctgcgcgttg gtgcggatat | 2100 |
| ctcggtagtg ggatacgacg ataccgaaga tagctcatgt tatatcccgc cgttaaccac | 2160 |
| catcaaacag gattttcgcc tgctggggca accagcgtg gaccgcttgc tgcaactctc | 2220 |
| tcagggccag gcggtgaagg gcaatcagct gttgccagtc tcactggtga aaagaaaaac | 2280 |
| caccctggcg cccaatacgc aaaccgcctc tccccgcgcg ttggccgatt cattaatgca | 2340 |
| gctggcacga caggtttccc gactggaaag cgggcagtga ctcatgacca aaatccctta | 2400 |
| acgtgagtta cgcgcgcgtc gttccactga gcgtcagacc ccgtagaaaa gatcaaagga | 2460 |
| tcttcttgag atcctttttt tctgcgcgta atctgctgct tgcaaacaaa aaaaccaccg | 2520 |
| ctaccagcgg tggtttgttt gccggatcaa gagctaccaa ctcttttttcc gaaggtaact | 2580 |
| ggcttcagca gagcgcagat accaaatact gttcttctag tgtagccgta gttagcccac | 2640 |
| cacttcaaga actctgtagc accgcctaca tacctcgctc tgctaatcct gttaccagtg | 2700 |
| gctgctgcca gtggcgataa gtcgtgtctt accgggttgg actcaagacg atagttaccg | 2760 |

```
gataaggcgc agcggtcggg ctgaacgggg ggttcgtgca cacagcccag cttggagcga    2820
acgacctaca ccgaactgag atacctacag cgtgagctat gagaaagcgc cacgcttccc    2880
gaagggagaa aggcggacag gtatccggta agcggcaggg tcggaacagg agagcgcacg    2940
agggagcttc caggggggaaa cgcctggtat ctttatagtc ctgtcgggtt cgccacctc    3000 tgacttgagc gtcgattttt gtgatgctcg tcagggggc ggagcctatg gaaaaacgcc    3060
agcaacgcgg ccttttttacg gttcctggcc ttttgctggc cttttgctca catgttcttt    3120
cctgcgttat cccctgattc tgtggataac cgtattaccg cctttgagtg agctgatacc    3180
gctcgccgca gccgaacgac cgagcgcagc gagtcagtga gcgaggaagc ggaaggcgag    3240
agtagggaac tgccaggcat caaactaagc agaaggcccc tgacggatgg ccttttttgcg    3300 tttctacaaa ctcttttctgt gttgtaaaac gacggcagt cttaagctcg gcccccctgg    3360
gcggttctga taacgagtaa tcgttaatcc gcaaataacg taaaaacccg cttcggcggg    3420
tttttttatg gggggagttt agggaaagag catttgtcag aatatttaag ggcgcctgtc    3480
actttgcttg atatatgaga attatttaac cttataaatg agaaaaaagc aacgcacttt    3540
aaataagata cgttgctttt tcgattgatg aacacctata attaaactat tcatctatta    3600
tttatgattt tttgtatata caatatttct agtttgttaa agagaattaa gaaaataaat    3660
ctcgaaaata ataaagggaa aatcagtttt tgatatcaaa attatacatg tcaacgataa    3720
tacaaaatat aatacaaact ataagatgtt atcagtattt attatgcatt tagaataaat    3780
tttgtgtcgc ccttattcga ctcactatag aagttcctat tctctagtaa gtataggaac    3840
ttcacttcat tttggatccg gccggcctgc agccccgcag ggcctgtctc ggtcgatcat    3900
tcagcccggc tcatagatat gcgggcagtg agcgcaacgc aattaatgta agttagctca    3960
ctcattaggc accccaggct tgacacttta tgcttccggc tcgtataatg tgtggaattg    4020
tgagcggata acaataacaa tttcacacag gatctaggaa ccaaggagag tggcatgccc    4080
accctcgcgc cttcaggtca acttgaaatc caagcgatcg gtgatgtctc caccgaagcc    4140
ggagcaatca ttacaaacgc tgaaatcgct tatcaccgct ggggtgaata ccgcgtagat    4200
aaagaaggac gcagcaatgt cgttctcatc gaacacgccc tcactggaga ttccaacgca    4260
gccgattggt gggctgactt gctcggtccc ggcaaagcca tcaacactga tatttactgc    4320
gtgatctgta ccaacgtcat cggtggttgc aacggttcca ccggacctgg ctccatgcat    4380
ccagatggaa atttctgggg taatcgcttc cccgccacgt ccattcgtga tcaggtaaac    4440
gccgaaaaac aattcctcga cgcactcggc atcaccacgg tcgccgcagt acttggtggt    4500
tccatgggtg gtgcccgcac cctagagtgg gccgcaatgt acccagaaac tgttggcgca    4560
gctgctgttc ttgcagtttc tgcacgcgcc agcgcctggc aaatcggcat tcaatccgcc    4620
caaattaagg cgattgaaaa cgaccaccac tggcacgaag gcaactacta cgaatccggc    4680
tgcaacccag ccaccggact cggcgccgcc cgacgcatcg cccacctcac ctaccgtggc    4740
gaactagaaa tcgacgaacg cttcggcacc aaagcccaaa agaacgaaaa cccactcggt    4800
ccctaccgca agcccgacca gcgcttcgcc gtggaatcct acttggacta ccaagcagac    4860
aagctagtac agcgtttcga cgccggctcc tacgtcttgc tcaccgacgc cctcaaccgc    4920
cacgacattg gtcgcgaccg cggaggcctc aacaaggcac tcgaatccat caaagttcca    4980
gtccttgtcg caggcgtaga taccgatatt ttgtaccccct accaccagca agaacacctc    5040
tccagaaacc tgggaaatct actggcaatg gcaaaaatcg tatcccctgt cggccacgat    5100
```

```
gctttcctca ccgaaagccg ccaaatggat cgcatcgtga ggaacttctt cagcctcatc    5160
tccccagacg aagacaaccc ttcgacctac atcgagttct acatctaata ggtatttacg    5220
acaaatagac agggatctct aaacaactca caggcaaccc tccggataaa cggatccaat    5280
tgtgagcgga taacaattac gagcttcatg cacagtgatc gacgctgttg acaattaatc    5340
atcggctcgt ataatgtgtg gatgtggaat tgtgagcgct cacaattcca caacggtttc    5400
cctctagaaa taattttgtt taacaggagg taaaacatat gcgagtgttg aagttcggcg    5460
gtacatcagt ggcaaatgca gaacgttttc tgcgtgttgc cgatattctg gaaagcaatg    5520
ccaggcaggg gcaggtggcc accgtcctct ctgcccccgc caaatcacc aaccacctgg     5580 tggcgatgat tgaaaaaacc attagcggcc aggatgcttt acccaatatc agcgatgccg    5640
aacgtatttt tgccgaactt ttgacggac tcgccgccgc ccagccgggg ttcccgctgg     5700
cgcaattgaa aactttcgtc gatcaggaat ttgcccaaat aaacatgtc ctgcatggca     5760 ttagtttgtt ggggcagtgc ccggatagca tcaacgctgc gctgatttgc cgtggcgaga    5820
aaatgtcgat cgccattatg gccggcgtat tagaagcgcg cggtcacaac gttactgtta    5880
tcgatccggt cgaaaaactg ctggcagtgg ggcattacct cgaatctacc gtcgatattg    5940
ctgagtccac ccgccgtatt gcggcaagcc gcattccggc tgatcacatg gtgctgatgg    6000
caggtttcac cgccggtaat gaaaaaggcg aactggtggt gcttggacgc aacggttccg    6060
actactctgc tgcggtgctg gctgcctgtt tacgcgccga ttgttgcgag atttggacgg    6120
acgttgacgg ggtctatacc tgcgacccgc gtcaggtgcc cgatgcgagg ttgttgaagt    6180
cgatgtccta ccaggaagcg atggagcttt cctacttcgg cgctaaagtt cttcaccccc    6240
gcaccattac ccccatcgcc cagttccaga tcccttgcct gattaaaaat accggaaatc    6300
ctcaagcacc aggtacgctc attggtgcca gccgtgatga agacgaatta ccggtcaagg    6360
gcatttccaa tctgaataac atggcaatgt tcagcgtttc tggtccgggg atgaaaggga    6420
tggtcggcat ggcggcgcgc gtcttttgcag cgatgtcacg cgcccgtatt ttcgtggtgc    6480
tgattacgca atcatcttcc gaatacagca tcagtttctg cgttccacaa agcgactgtg    6540
tgcgagctga acgggcaatg caggaagagt tctacctgga actgaaagaa ggcttactgg    6600
agccgctggc agtgacggaa cggctggcca ttatctcggt ggtaggtgat ggtatgcgca    6660
ccttgcgtgg gatctcggcg aaattctttg ccgcactggc ccgcgccaat atcaacattg    6720
tcgccattgc tcagggatct tctgaacgct caatctctgt cgtggtaaat aacgatgatg    6780
cgaccactgg cgtgcgcgtt actcatcaga tgctgttcaa taccgatcag gttatcgaag    6840
tgtttgtgat tggcgtcggt ggcgttggcg gtgcgctgct ggagcaactg aagcgtcagc    6900
aaagctggct gaagaataaa catatcgact acgtgtctg cggtgttgcc aactcgaagg     6960
ctctgctcac caatgtacat ggccttaatc tggaaaactg gcaggaagaa ctggcgcaag    7020
ccaaagagcc gtttaatctc gggcgcttaa ttcgcctcgt gaaagaatat catctgctga    7080
acccggtcat tgttgactgc acttccagcc aggcagtggc ggatcaatat gccgacttcc    7140
tgcgcgaagg tttccacgtt gtcacgccga caaaaaggc caacacctcg tcgatggatt    7200
actaccatca gttgcgttat gcggcggaaa atcgcggcg taaattcctc tatgacacca    7260 acgttgggc tggattaccg gttattgaga acctgcaaaa tctgctcaat gcaggtgatg    7320
aattgatgaa gttctccggc attctttctg gttcgctttc ttatatcttc ggcaagttag    7380
acgaaggcat gagtttctcc gaggcgacca cgctggcgcg ggaaatgggt tataccgaac    7440
cggacccgcg agatgatctt tctggtatgg atgtggcgcg taaactattg attctcgctc    7500
```

```
gtgaaacggg acgtgaactg gagctggcgg atattgaaat tgaacctgtg ctgcccgcag    7560
agtttaacgc cgagggtgat gttgccgctt ttatggcgaa tctgtcacaa ctcgacgatc    7620
tctttgccgc gcgcgtggcg aaggcccgtg atgaaggaaa agttttgcgc tatgttggca    7680
atattgatga agatggcgtc tgccgcgtga agattgccga agtggatggt aatgatccgc    7740
tgttcaaagt gaaaaatggc gaaaacgccc tggccttcta tagccactat tatcagccgc    7800
tgccgttggt actgcgcgga tatggtgcgg gcaatgacgt tacagctgcc ggtgtctttg    7860
ctgatctgct acgtaccctc tcatggaagt taggagtctg ataaatcaac aactctcctg    7920
gcgcaccatc gtcggctaca gcctcgggaa ttgctgcaag tcgacggatc gccggaatta    7980
attctcatgt ttgacagctt atcactgatc agtgaattaa tggcgatgac gcatcctcac    8040
gataatatcc gggtaggcgc aatcactttc gtctctactc cgttacaaag cgaggctggg    8100
tatttcccgg ccttttgggg ccggccggat ccccccactt cagaagttcc tatac         8155
```

<210> SEQ ID NO 43  
<211> LENGTH: 4039  
<212> TYPE: DNA  
<213> ORGANISM: Artificial Sequence  
<220> FEATURE:  
<223> OTHER INFORMATION: pCDF_Ptac

<400> SEQUENCE: 43

```
cgggatctcg acgctctccc ttatgcgact cctgcgttta gggaaagagc atttgtcaga      60
atatttaagg gcgcctgtca ctttgcttga tatatgagaa ttatttaacc ttataaatga     120
gaaaaaagca acgcacttta aataagatac gttgcttttt cgattgatga acacctataa     180
ttaaactatt catctattat ttatgatttt ttgtatatac aatatttcta gtttgttaaa     240
gagaattaag aaaataaatc tcgaaaataa taagggaaa  atcagttttt gatatcaaaa     300
ttatacatgt caacgataat acaaaatata atacaaacta aagatgtta tcagtattta      360 ttatgcattt agaataccct ttgtgtcgcc cttattcgac tccctataga agttcctatt     420
ctctagaaag tataggaact tcccttcatt ttggatccaa ttgtgagcgg ataacaatta     480
cgagcttcat gcacagtgat cgacgctgtt gacaattaat catcggctcg tataatgtgt     540
ggatgtggaa ttgtgagcgc tcacaattcc acaacggttt ccctctagaa ataattttgt     600
ttaacaggag gtaaaacata tggcagatct caattggata tcggccggcc acgcgatcgc     660
tgacgtcggt accctcgagt ctggtaaaga accgctgctg cgaaatttg aacgccagca     720 catggactcg tctactagcg cagcttaatt aacctaggct gctgccaccg ctgagcaata    780
actagcataa ccccttgggg cctctaaacg ggtcttgagg ggttttttgc tgaaacctca     840
ggcatttgag aagcacacgg tcacactgct tccggtagtc aataaaccgg taaaccagca    900
atagacataa gcggctattt aacgaccctg ccctgaaccg acgaccgggt catcgtggcc     960
ggatcttgcg gcccctcggc ttgaacgaat tgttagacat tatttgccga ctaccttggt    1020
gatctcgcct ttcacgtagt ggacaaattc ttccaactga tctgcgcgcg aggccaagcg    1080
atcttcttct tgtccaagat aagcctgtct agcttcaagt atgacgggct gatactgggc    1140
cggcaggcgc tccattgccc agtcggcagc gacatccttc ggcgcgattt tgccggttac    1200
tgcgctgtac caaatgcggg acaacgtaag cactacattt cgctcatcgc cagcccagtc    1260
gggcggcgag ttccatagcg ttaaggtttc atttagcgcc tcaaatagat cctgttcagg    1320
aaccggatca aagagttcct ccgccgctgg acctaccaag gcaacgctat gttctcttgc    1380
```

-continued

```
ttttgtcagc aagatagcca gatcaatgtc gatcgtggct ggctcgaaga tacctgcaag    1440
aatgtcattg cgctgccatt ctccaaattg cagttcgcgc ttagctggat aacgccacgg    1500
aatgatgtcg tcgtgcacaa caatggtgac ttctacagcg cggagaatct cgctctctcc    1560
aggggaagcc gaagtttcca aaaggtcgtt gatcaaagct cgccgcgttg tttcatcaag    1620
ccttacggtc accgtaacca gcaaatcaat atcactgtgt ggcttcaggc cgccatccac    1680
tgcggagccg tacaaatgta cggccagcaa cgtcggttcg agatggcgct cgatgacgcc    1740
aactacctct gatagttgag tcgatacttc ggcgatcacc gcttccctca tactcttcct    1800
ttttcaatat tattgaagca tttatcaggg ttattgtctc atgagcggat acatatttga    1860
atgtatttag aaaaataaac aaatagctag ctcactcggt cgctacgctc cgggcgtgag    1920
actgcggcgg gcgctgcgga cacatacaaa gttacccaca gattccgtgg ataagcaggg    1980
gactaacatg tgaggcaaaa cagcagggcc gcgccggtgg cgttttttcca taggctccgc   2040 cctcctgcca gagttcacat aaacagacgc ttttccggtg catctgtggg agccgtgagg    2100
ctcaaccatg aatctgacag tacgggcgaa acccgacagg acttaaagat ccccaccgtt    2160
tccggcgggt cgctcccctct tgcgctctcc tgttccgacc ctgccgttta ccggatacct    2220
gttccgcctt tctcccttac gggaagtgtg gcgctttctc atagctcaca cactggtatc    2280
tcggctcggt gtaggtcgtt cgctccaagc tgggctgtaa gcaagaactc cccgttcagc    2340
ccgactgctg cgccttatcc ggtaactgtt cacttgagtc caacccggaa aagcacggta    2400
aaacgccact ggcagcagcc attggtaact gggagttcgc agaggatttg tttagctaaa    2460
cacgcggttg ctcttgaagt gtgcgccaaa gtccggctac actggaagga cagatttggt    2520
tgctgtgctc tgcgaaagcc agttaccacg gttaagcagt cccccaactg acttaacctt    2580
cgatcaaacc acctccccag gtggtttttt cgtttacagg gcaaaagatt acgcgcagaa    2640
aaaaaggatc tcaagaagat cctttgatct tttctactga accgctctag atttcagtgc    2700
aatttatctc ttcaaatgta gcacctgaag tcagccccat acgatataag ttgtaattct    2760
catgttagtc atgccccgcg cccaccggaa ggagctgact gggttgaagg ctctcaaggg    2820
catcggtcga gatcccggtg cctaatgagt gagctaactt acattaattg cgttgcgctc    2880
actgcccgct ttccagtcgg gaaacctgtc gtgccagctg cattaatgaa tcggccaacg    2940
cgcggggaga ggcggtttgc gtattgggcg ccagggtggt ttttcttttc accagtgaga    3000
cgggcaacag ctgattgccc ttcaccgcct ggccctgaga gagttgcagc aagcggtcca    3060
cgctggtttg cccagcagg cgaaaatcct gtttgatggt ggttaacggc gggatataac    3120
atgagctgtc ttcggtatcg tcgtatccca ctaccgagat gtccgcacca acgcgcagcc    3180
cggactcggt aatggcgcgc attgcgccca gcgccatctg atcgttggca accagcatcg    3240
cagtgggaac gatgccctca ttcagcattt gcatggtttg ttgaaaaccg gacatggcac    3300
tccagtcgcc ttcccgttcc gctatcggct gaatttgatt gcgagtgaga tatttatgcc    3360
agccagccag acgcagacgc gccgagacag aacttaatgg gcccgctaac agcgcgattt    3420
gctggtgacc caatgcgacc agatgctcca cgcccagtcg cgtaccgtct tcatgggaga    3480
aaataatact gttgatgggt gtctggtcag agacatcaag aaataacgcc ggaacattag    3540
tgcaggcagc ttccacagca atggcatcct ggtcatccag cggatagtta atgatcagcc    3600
cactgacgcg ttgcgcgaga agattgtgca ccgccgcttt acaggcttcg acgccgcttc    3660
gttctaccat cgacaccacc acgctggcac ccagttgatc ggcgcgagat taatcgccg    3720 cgacaatttg cgacggcgcg tgcagggcca gactggaggt ggcaacgcca atcagcaacg    3780
```

```
actgtttgcc cgccagttgt tgtgccacgc ggttgggaat gtaattcagc tccgccatcg    3840
ccgcttccac ttttcccgc gttttcgcag aaacgtggct ggcctggttc accacgcggg     3900
aaacggtctg ataagagaca ccggcatact ctgcgacatc gtataacgtt actggtttca    3960
cattcaccac cctgaattga ctctcttccg ggcgctatca tgccataccg cgaaaggttt    4020
tgcgccattc gatggtgtc                                                 4039
```

<210> SEQ ID NO 44
<211> LENGTH: 25
<212> TYPE: DNA
<213> ORGANISM: Artificial Sequence
<220> FEATURE:
<223> OTHER INFORMATION: primer_thrAfbr_fw

<400> SEQUENCE: 44

```
gtttaacagg aggtaaaaca tatgc                                          25
```

<210> SEQ ID NO 45
<211> LENGTH: 33
<212> TYPE: DNA
<213> ORGANISM: Artificial Sequence
<220> FEATURE:
<223> OTHER INFORMATION: primer_thrAfbr_rev

<400> SEQUENCE: 45

```
gctcactgcc ttatcagact cctaacttcc atg                                 33
```

<210> SEQ ID NO 46
<211> LENGTH: 35
<212> TYPE: DNA
<213> ORGANISM: Artificial Sequence
<220> FEATURE:
<223> OTHER INFORMATION: primer_Placuv5_fw

<400> SEQUENCE: 46

```
agtctgataa ggcagtgagc gcaacgcaat taatg                               35
```

<210> SEQ ID NO 47
<211> LENGTH: 48
<212> TYPE: DNA
<213> ORGANISM: Artificial Sequence
<220> FEATURE:
<223> OTHER INFORMATION: primer_metX_rev

<400> SEQUENCE: 47

```
cagcggtttc tttaccagac ctattagatg tagaactcga tgtaggtc                 48
```

<210> SEQ ID NO 48
<211> LENGTH: 7734
<212> TYPE: DNA
<213> ORGANISM: Artificial Sequence
<220> FEATURE:
<223> OTHER INFORMATION: pJAG-4-50

<400> SEQUENCE: 48

```
cgggatctcg acgctctccc ttatgcgact cctgcgttta gggaaagagc atttgtcaga    60
atatttaagg gcgcctgtca ctttgcttga tatatgagaa ttatttaacc ttataaatga    120 gaaaaagca acgcacttta ataagatac gttgcttttt cgattgatga cacctataa      180 ttaaactatt catctattat ttatgatttt ttgtatatac aatatttcta gtttgttaaa    240
gagaattaag aaaataaatc tcgaaaataa taaagggaaa atcagttttt gatatcaaaa    300
```

```
ttatacatgt caacgataat acaaaatata atacaaacta taagatgtta tcagtattta    360
ttatgcattt agaataccct ttgtgtcgcc cttattcgac tccctataga agttcctatt    420
ctctagaaag tataggaact tcccttcatt ttggatccaa ttgtgagcgg ataacaatta    480
cgagcttcat gcacagtgat cgacgctgtt gacaattaat catcggctcg tataatgtgt    540
ggatgtggaa ttgtgagcgc tcacaattcc acaacggttt ccctctagaa ataattttgt    600
ttaacaggag gtaaaacata tgcgagtgtt aagttcggc ggtacatcag tggcaaatgc     660
agaacgtttt ctgcgtgttg ccgatattct ggaaagcaat gccaggcagg ggcaggtggc    720
caccgtcctc tctgccccg ccaaaatcac caaccacctg gtggcgatga ttgaaaaaac     780
cattagcggc caggatgctt tacccaatat cagcgatgcc gaacgtattt ttgccgaact    840
tttgacggga ctcgccgccg cccagccggg gttcccgctg gcgcaattga aaactttcgt    900
cgatcaggaa tttgcccaaa taaaacatgt cctgcatggc attagtttgt tggggcagtg    960
cccggatagc atcaacgctg cgctgatttg ccgtggcgag aaaatgtcga tcgccattat   1020
ggccggcgta ttagaagcgc gcggtcacaa cgttactgtt atcgatccgg tcgaaaaact   1080
gctggcagtg gggcattacc tcgaatctac cgtcgatatt gctgagtcca cccgccgtat   1140
tgcggcaagc cgcattccgg ctgatcacat ggtgctgatg caggtttca ccgccggtaa    1200
tgaaaaaggc gaactggtgg tgcttggacg caacggttcc gactactctg ctgcggtgct   1260
ggctgcctgt ttacgcgccg attgttgcga gatttggacg gacgttgacg gggtctatac   1320
ctgcgacccg cgtcaggtgc ccgatgcgag gttgttgaag tcgatgtcct accaggaagc   1380
gatggagctt tcctacttcg gcgctaaagt tcttcacccc cgcaccatta cccccatcgc   1440
ccagttccag atcccttgcc tgattaaaaa taccggaaat cctcaagcac caggtacgct   1500
cattggtgcc agccgtgatg aagacgaatt accggtcaag gcatttccaa atctgaataa   1560
catggcaatg ttcagcgttt ctggtccggg gatgaaaggg atggtcggca tggcggcgcg   1620
cgtctttgca gcgatgtcac gcgcccgtat tttcgtggtg ctgattacgc aatcatcttc   1680
cgaatacagc atcagtttct gcgttccaca aagcgactgt gtgcgagctg aacgggcaat   1740
gcaggaagag ttctacctgg aactgaaaga aggcttactg gagccgctgg cagtgacgga   1800
acggctggcc attatctcgg tggtaggtga tggtatgcgc accttgcgtg ggatctcggc   1860
gaaattcttt gccgcactgg cccgcgccaa tatcaacatt gtcgccattg ctcagggatc   1920
ttctgaacgc tcaatctctg tcgtggtaaa taacgatgat gcgaccactg gcgtgcgcgt   1980
tactcatcag atgctgttca ataccgatca ggttatcgaa gtgtttgtga ttggcgtcgg   2040
tggcgttggc ggtgcgctgc tggagcaact gaagcgtcag caaagctggc tgaagaataa   2100
acatatcgac ttacgtgtct gcggtgttgc caactcgaag gctctgctca ccaatgtaca   2160
tggccttaat ctggaaaact ggcaggaaga actggcgcaa gccaaagagc cgtttaatct   2220
cgggcgctta attcgcctcg tgaaagaata tcatctgctg aacccggtca ttgttgactg   2280
cacttccagc caggcagtgg cggatcaata tgccgacttc ctgcgcgaag gtttccacgt   2340
tgtcacgccg aacaaaaagg ccaacacctc gtcgatggat tactaccatc agttgcgtta   2400
tgcggcggaa aaatcgcggc gtaaattcct ctatgacacc aacgttgggg ctggattacc   2460
ggttattgag aacctgcaaa atctgctcaa tgcaggtgat gaattgatga gttctccgg    2520
cattcttcct ggttcgcttt cttatatctt cggcaagtta gacgaaggca tgagtttctc   2580
cgaggcgacc acgctggcgc gggaaatggg ttataccgaa ccggaccgc gagatgatct    2640
ttctggtatg gatgtggcgc gtaaactatt gattctcgct cgtgaaacgg gacgtgaact   2700
```

```
ggagctggcg atattgaaa ttgaacctgt gctgcccgca gagtttaacg ccgagggtga   2760
tgttgccgct tttatggcga atctgtcaca actcgacgat ctctttgccg cgcgcgtggc   2820
gaaggcccgt gatgaaggaa aagttttgcg ctatgttggc aatattgatg aagatggcgt   2880
ctgccgcgtg aagattgccg aagtggatgg taatgatccg ctgttcaaag tgaaaaatgg   2940
cgaaaacgcc ctggccttct atagccacta ttatcagccg ctgccgttgg tactgcgcgg   3000
atatggtgcg ggcaatgacg ttacagctgc cggtgtcttt gctgatctgc tacgtaccct   3060
ctcatggaag ttaggagtct gataaggcag tgagcgcaac gcaattaatg taagttagct   3120
cactcattag caccccagg cttgacactt tatgcttccg gctcgtataa tgtgtggaat   3180
tgtgagcgga taacaataac aatttcacac aggatctagg aaccaaggag agtggcatgc   3240
ccaccctcgc gccttcaggt caacttgaaa tccaagcgat cggtgatgtc tccaccgaag   3300
ccggagcaat cattacaaac gctgaaatcg cctatcaccg ctggggtgaa taccgcgtag   3360
ataaagaagg acgcagcaat gtcgttctca tcgaacacgc cctcactgga gattccaacg   3420
cagccgattg gtgggctgac ttgctcggtc ccggcaaagc catcaacact gatatttact   3480
gcgtgatctg taccaacgtc atcggtggtt gcaacggttc caccggacct ggctccatgc   3540
atccagatgg aaatttctgg ggtaatcgct tccccgccac gtccattcgt gatcaggtaa   3600
acgccgaaaa acaattcctc gacgcactcg gcatcaccac ggtcgccgca gtacttggtg   3660
gttccatggg tggtgcccgc accctagagt gggccgcaat gtacccagaa actgttggcg   3720
cagctgctgt tcttgcagtt ctgcacgcg ccagcgcctg gcaaatcggc attcaatccg   3780
cccaaattaa ggcgattgaa aacgaccacc actggcacga aggcaactac tacgaatccg   3840
gctgcaaccc agccaccgga ctcggcgccg cccgacgcat cgcccacctc acctaccgtg   3900
gcgaactaga aatcgacgaa cgcttcggca ccaaagccca aaagaacgaa aacccactcg   3960
gtccctaccg caagcccgac cagcgcttcg ccgtggaatc ctacttggac taccaagcag   4020
acaagctagt acagcgtttc gacgccggct cctacgtctt gctcaccgac gccctcaacc   4080
gccacgacat tggtcgcgac cgcggaggcc tcaacaaggc actcgaatcc atcaaagttc   4140
cagtccttgt cgcaggcgta gataccgata ttttgtaccc ctaccaccag caagaacacc   4200
tctccagaaa cctgggaaat ctactggcaa tggcaaaaat cgtatcccct gtcggccacg   4260
atgctttcct caccgaaagc cgccaaatgg atcgcatcgt gaggaacttc ttcagcctca   4320
tctccccaga cgaagacaac ccttcgacct acatcgagtt ctacatctaa taggtctggt   4380
aaagaaaccg ctgctgcgaa atttgaacgc cagcacatgg actcgtctac tagcgcagct   4440
taattaacct aggctgctgc caccgctgag caataactag cataacccct tggggcctct   4500
aaacgggtct tgaggggttt tttgctgaaa cctcaggcat tgagaagca cacggtcaca   4560 ctgcttccgg tagtcaataa accggtaaac cagcaataga cataagcggc tatttaacga   4620
ccctgccctg aaccgacgac cgggtcatcg tggccggatc ttgcgccccc tcggcttgaa   4680
cgaattgtta gacattattt gccgactacc ttggtgatct cgccttcac gtagtggaca   4740 aattcttcca actgatctgc gcgcgaggcc aagcgatctt cttcttgtcc aagataagcc   4800
tgtctagctt caagtatgac gggctgatac tgggccggca ggcgctccat tgcccagtcg   4860
gcagcgacat ccttcggcgc gattttgccg gttactgcgc tgtaccaaat gcgggacaac   4920
gtaagcacta catttcgctc atcgccagcc cagtcgggcg gcgagttcca tagcgttaag   4980
gtttcattta gcgcctcaaa tagatcctgt tcaggaaccg gatcaaagag ttcctccgcc   5040
```

```
gctggaccta ccaaggcaac gctatgttct cttgcttttg tcagcaagat agccagatca    5100
atgtcgatcg tggctggctc gaagatacct gcaagaatgt cattgcgctg ccattctcca    5160
aattgcagtt cgcgcttagc tggataacgc cacggaatga tgtcgtcgtg cacaacaatg    5220
gtgacttcta cagcgcggag aatctcgctc tctccagggg aagccgaagt ttccaaaagg    5280
tcgttgatca aagctcgccg cgttgtttca tcaagcctta cggtcaccgt aaccagcaaa    5340
tcaatatcac tgtgtggctt caggccgcca tccactgcgg agccgtacaa atgtacggcc    5400
agcaacgtcg gttcgagatg gcgctcgatg acgccaacta cctctgatag ttgagtcgat    5460
acttcggcga tcaccgcttc cctcatactc ttccttttc aatattattg aagcatttat    5520
cagggttatt gtctcatgag cggatacata tttgaatgta tttagaaaaa taaacaaata    5580
gctagctcac tcggtcgcta cgctccgggc gtgagactgc ggcgggcgct gcggacacat    5640
acaaagttac ccacagattc cgtggataag caggggacta acatgtgagg caaaacagca    5700
gggccgcgcc ggtggcgttt ttccataggc tccgccctcc tgccagagtt cacataaaca    5760
gacgcttttc cggtgcatct gtgggagccg tgaggctcaa ccatgaatct gacagtacgg    5820
gcgaaacccg acaggactta aagatcccca ccgtttccgg cgggtcgctc cctcttgcgc    5880
tctcctgttc cgaccctgcc gtttaccgga tacctgttcc gcctttctcc cttacgggaa    5940
gtgtggcgct ttctcatagc tcacacactg gtatctcggc tcggtgtagg tcgttcgctc    6000
caagctgggc tgtaagcaag aactccccgt tcagcccgac tgctgcgcct tatccggtaa    6060
ctgttcactt gagtccaacc cggaaaagca cggtaaaacg ccactggcag cagccattgg    6120
taactgggag ttcgcagagg atttgtttag ctaaacacgc ggttgctctt gaagtgtgcg    6180
ccaaagtccg gctacactgg aaggacagat ttggttgctg tgctctgcga agccagtta    6240 ccacggttaa gcagttcccc aactgactta accttcgatc aaaccacctc cccaggtggt    6300 ttttcgttt acagggcaaa agattacgcg cagaaaaaaa ggatctcaag aagatccttt    6360
gatcttttct actgaaccgc tctagatttc agtgcaattt atctcttcaa atgtagcacc    6420
tgaagtcagc cccatacgat ataagttgta attctcatgt tagtcatgcc ccgcgcccac    6480
cggaaggagc tgactgggtt gaaggctctc aagggcatcg gtcgagatcc cggtgcctaa    6540
tgagtgagct aacttacatt aattgcgttg cgctcactgc ccgctttcca gtcgggaaac    6600
ctgtcgtgcc agctgcatta tgaatcggc caacgcgcgg ggagaggcgg tttgcgtatt    6660
gggcgccagg gtggtttttc ttttcaccag tgagacgggc aacagctgat tgcccttcac    6720
cgcctggccc tgagagagtt gcagcaagcg gtccacgctg gtttgcccca gcaggcgaaa    6780
atcctgtttg atggtggtta acggcgggat ataacatgag ctgtcttcgg tatcgtcgta    6840
tcccactacc gagatgtccg caccaacgcg cagcccggac tcggtaatgg cgcgcattgc    6900
gcccagcgcc atctgatcgt tggcaaccag catcgcagtg gaacgatgc cctcattcag    6960 catttgcatg gtttgttgaa aaccggacat ggcactccag tcgccttccc gttccgctat    7020
cggctgaatt tgattgcgag tgagatattt atgccagcca ccagacgca gacgcgccga    7080 gacagaactt aatgggcccg ctaacagcgc gatttgctgg tgacccaatg cgaccagatg    7140
ctccacgccc agtcgcgtac cgtcttcatg ggagaaaata atactgttga tgggtgtctg    7200
gtcagagaca tcaagaaata cgccggaac attagtgcag gcagcttcca cagcaatggc    7260
atcctggtca tccagcggat agttaatgat cagcccactg acgcgttgcg cgagaagatt    7320
gtgcaccgcc gctttacagg cttcgacgcc gcttcgttct accatcgaca ccaccacgct    7380
ggcacccagt tgatcggcgc gagatttaat cgccgcgaca atttgcgacg cgcgtgcag    7440
```

| | | | | |
|---|---|---|---|---|
| ggccagactg | gaggtggcaa | cgccaatcag | caacgactgt | ttgcccgcca | gttgttgtgc | 7500 |
| cacgcggttg | ggaatgtaat | tcagctccgc | catcgccgct | tccactttt | cccgcgtttt | 7560 |
| cgcagaaacg | tggctggcct | ggttcaccac | gcgggaaacg | gtctgataag | agacaccggc | 7620 |
| atactctgcg | acatcgtata | acgttactgg | tttcacattc | accaccctga | attgactctc | 7680 |
| ttccgggcgc | tatcatgcca | taccgcgaaa | ggttttgcgc | cattcgatgg | tgtc | 7734 |

<210> SEQ ID NO 49
<211> LENGTH: 8174
<212> TYPE: DNA
<213> ORGANISM: Artificial Sequence
<220> FEATURE:
<223> OTHER INFORMATION: pECXC99E-[metX_Cg]

<400> SEQUENCE: 49

| | | | | | |
|---|---|---|---|---|---|
| gtttgacagc | ttatcatcga | ctgcacggtg | caccaatgct | tctggcgtca | ggcagccatc | 60 |
| ggaagctgtg | gtatggctgt | gcaggtcgta | aatcactgca | taattcgtgt | cgctcaaggc | 120 |
| gcactcccgt | tctggataat | gttttttgcg | ccgacatcat | aacggttctg | gcaaatattc | 180 |
| tgaaatgagc | tgttgacaat | taatcatccg | gctcgtataa | tgtgtggaat | tgtgagcgga | 240 |
| taacaatttc | acacaggaaa | cagaccatgg | aattcgagct | cggtaccgg | gatcctagtc | 300 |
| ttgtccaccc | agaacaggcg | gttatttca | tgcccaccct | cgcgccttca | ggtcaacttg | 360 |
| aaatccaagc | gatcggtgat | gtctccaccg | aagccgagc | aatcattaca | aacgctgaaa | 420 |
| tcgcctatca | ccgctggggt | gaataccgcg | tagataaaga | aggacgcagc | aatgtcgttc | 480 |
| tcatcgaaca | cgccctcact | ggagattcca | acgcagccga | ttggtgggct | gacttgctcg | 540 |
| gtcccggcaa | agccatcaac | actgatattt | actgcgtgat | ctgtaccaac | gtcatcggtg | 600 |
| gttgcaacgg | ttccaccgga | cctggctcca | tgcatccaga | tggaaatttc | tggggtaatc | 660 |
| gcttccccgc | cacgtccatt | cgtgatcagg | taaacgccga | aaaacaattc | ctcgacgcac | 720 |
| tcggcatcac | cacggtcgcc | gcagtacttg | gtggttccat | gggtggtgcc | cgcacctag | 780 |
| agtgggccgc | aatgtaccca | gaaactgttg | gcgcagctgc | tgttcttgca | gtttctgcac | 840 |
| gcgccagcgc | ctggcaaatc | ggcattcaat | ccgcccaaat | taaggcgatt | gaaaacgacc | 900 |
| accactggca | cgaaggcaac | tactacgaat | ccggctgcaa | cccagccacc | ggactcggcg | 960 |
| ccgcccgacg | catcgcccac | ctcacctacc | gtggcgaact | agaaatcgac | gaacgcttcg | 1020 |
| gcaccaaagc | ccaaaagaac | gaaaacccac | tcggtcccta | ccgcaagccc | gaccagcgct | 1080 |
| tcgccgtgga | atcctacttg | gactaccaag | cagacaagct | agtacagcgt | ttcgacgccg | 1140 |
| gctcctacgt | cttgctcacc | gacgccctca | accgccacga | cattggtcgc | gaccgcggag | 1200 |
| gcctcaacaa | ggcactcgaa | tccatcaaag | ttccagtcct | tgtcgcaggc | gtagataccg | 1260 |
| atatttttgta | cccctaccac | cagcaagaac | acctctccag | aaacctggga | aatctactgg | 1320 |
| caatggcaaa | aatcgtatcc | cctgtcggcc | acgatgcttt | cctcaccgaa | agccgccaaa | 1380 |
| tggatcgcat | cgtgaggaac | ttcttcagcc | tcatctcccc | agacgaagac | aacccttcga | 1440 |
| cctacatcga | gttctacatc | taataggtat | ttacgacaaa | tagacaggga | tctctaaaca | 1500 |
| actcacaggc | aaccctccgg | ataaaccaac | tgcaggcatg | caagcttggc | tgttttggcg | 1560 |
| gatgagagaa | gattttcagc | ctgatacaga | ttaaatcaga | acgcagaagc | ggtctgataa | 1620 |
| aacagaatt | gcctggcggc | agtagcgcgg | tggtcccacc | tgaccccatg | ccgaactcag | 1680 |
| aagtgaaacg | ccgtagcgcc | gatggtagtg | tggggtctcc | ccatgcgaga | gtagggaact | 1740 |

```
gccaggcatc aaataaaacg aaaggctcag tcgaaagact gggcctttcg ttttatctgt   1800
tgtttgtcgg tgaacgctct cctgagtagg acaaatccgc cgggagcgga tttgaacgtt   1860
gcgaagcaac ggcccggagg gtggcgggca ggacgcccgc cataaactgc caggcatcaa   1920
attaagcaga aggccatcct gacggatggc cttttttgcgt ttctacaaac tcttttgttt   1980 attttttctaa atacattcaa atatgtatcc gctcatgaat taattccgct agatccccat   2040
caatcctgcc tatttgccac gtttaacaag gtagttaagc gttcatttac gaagaaaaca   2100
cgataagctg cacaaatacc tgaaaaagtt gaacgccccg tgagcgggaa ctcacagggc   2160
gtcggctaac ccccagtcat cagctgggag aaagcactca agacatgact ctagccgatc   2220
cgcaggacac agtcacagct agcgcgtgga aattttccgc cgatctgttc gacacccacc   2280
ccgaactagc gctgcggctc acgcggctgg acggcagaag atcgccgcga actgctcgct   2340
cacctgggac gcgaaagctt ccagggcagc aagacaagag atttcgcgag cgcctggatt   2400
aaaaacccgg ataccggcga aacccaacca aagctctacc gggctggctc aaaagcgctg   2460
acgcggtgcc agtacgttgc gctgacgcac gcgcaacatg ccgcggtgat cgtgcttgac   2520
atcgatgtgc ccagccacca ggccggcggg aagattgagc acgtaaaccc gcaggtctac   2580 gcgatttttag agaaatgggc acgcctagaa aaagcgccgg cttggatcgg cgtgaatccg   2640
ctgagcggga aatgccagct catctggctc attgacccgg tgtatgccgc agcaggtaaa   2700
accagcccaa atatgcgcct gctggctgca acgacgaag aaatgactcg tgttttcggc   2760
gctgaccagg cttttttcgca taggctgagc cggtggccgc tgcacgtctc agacgatccg   2820
acagcctata aatggcactg ccagcatgat cgtgtggatc ggctggccga cctaatggag   2880
attgctcgaa cgatgaccgg atcacagaag ccgaaaaagt acattgagca ggacttttcc   2940
agcggacgcg cccgcattga agcggcacaa cgcgccaccg cagaagccaa ggcgctagcg   3000
attttggacg cgagcctgcc gagcgccctg gacgcgtccg gcgacctgat cgacggcgtg   3060
cgagtgctct ggacaaatcc agagcgagcg cgcgacgaga ccgcgtttcg ccacgcgttg   3120
accgtgggat accagctcaa agctgctggt gagcgcctaa aagatgccaa gatcatcgac   3180
gcgtatgaag tggcgtacaa cgttgcccag gcggtcggtg cagacggccg ggagccggat   3240
cttcccgcca tgcgtgatcg cctgacgatg gcgcgtcgtg tgcgcggcta cgtggctaaa   3300
ggccagccag tcgtccctgc tcgtcgggtg gaaacgcaga gcagccgagg gcggaaagct   3360
ctagcgacga tgggcgacg gggcgcagct acatcgaatg cacgcagatg ggctgaccca   3420
gaaagtaagt atgcgcagga gacgcgcacg cgattagcgg aagcaaacaa acgccgagaa   3480
atgacaggcg agttgctcga acttcgcgtc aaaactgcga tcctggatgc ccgttctcaa   3540
tcggttgctg atccctcgac tcgtgagctt gcaggcgaac taggtgtcag tgaaaggcgc   3600
atccaacaag tcagaaaggc acttggaatg gaagctaaac gcggccgtcc acgggctgaa   3660
aactaataaa cgaaacaccg tcagcagaaa acggttcccc cctttagggg tcccgtcctt   3720
gctctggctc tcacttgccc tcaccctccg ctatccacgg gctgaaaact aataaacgaa   3780
acaccgtcag cagaaaacgg ttccccccct ttagggtgtc tcgctcctag ctctgatccc   3840
tccccggttc ctccccggcc tgattttaa gggggggctca cgctgtcggc agagaacggt   3900
tccccgcctt ctgctctggc tcttcctcga ctccctcccc ctcaaaaatc tcctcgagat   3960
cctggagacc ttttttggagc tagcgcgttg ctgcttcgca ccaacttgct catgatgatt   4020 ttcattttttg cttgtgtgct ttttttgggtt gaaccctcca aagaggggaa accagggggca   4080 cacctcatgc actaaagtgc cgcttcgctg gtcagggtga aatcacctgg aaaaaaagtg   4140
```

```
cggtaaccgc tgcgcttggc gttttttctg ggcaagaagt ctcgcaggtt ttcgcaggag    4200
tgccggaaga aattatcaga attggggcta gaattttaa cgaacgttcg ttataatggt     4260
gtcatgacct tcacgacgaa gtaccaaaac tggcctgaag catcagcggt ggatctctcc    4320
gatgtcgcgc tggagtccga cgcactcgat gccgccgtcg atttaaaaac ggtgatcgga    4380
tttttccgcg ccctcgatac gacagacgcg ccagcatcac gcgactgggc aagtgccgcg    4440
agcgacctag aaacgcttgt ggccgacctt gaagagctgg ccgacgagct gcgtgctcgg    4500
cagcgccagg aggacgcgca gtagtggagg atcgcatcag ctgcgcctac tgcggtggcc    4560
tgatcccacc ccgcctgac ccacgaggac ggcgcgcaaa atactgctca gacgcgtgtc     4620
gtgccgcagc cagccgcgag cgcgccaaca agcgccacgc ccaggaggtc gaagccgcac    4680
gtcatctagc gctgatgtcc ggcggtgctt ttgccgttac gcaccacccc gtcagtagct    4740
gaacaggagg gacagctgat agaaacagaa gccactggag cacctcaaaa acaccatcat    4800
acactaaatc agtaagttgg cagcatcacc cgacgcactt tgcgccgaat aaatacctgt    4860
gacggaagat cacttcgcag aataaataaa tcctggtgtc cctgttgata ccgggaagcc    4920
ctgggccaac ttttggcgaa aatgagacgt tgatcggcac gtaagaggtt ccaactttca    4980
ccataatgaa ataagatcac taccgggcgt attttttgag ttatcgagat tttcaggagc    5040
taaggaagct aaaatggaga aaaaaatcac tggatatacc accgttgata tatcccaatg    5100
gcatcgtaaa gaacattttg aggcatttca gtcagttgct caatgtacct ataaccagac    5160
cgttcagctg gatattacgg cctttttaaa gaccgtaaag aaaaataagc acaagtttta    5220
tccggccttt attcacattc ttgcccgcct gatgaatgct catccggaat tccgtatggc    5280
aatgaaagac ggtgagctgg tgatatggga tagtgttcac ccttgttaca ccgttttcca    5340
tgagcaaact gaaacgtttt catcgctctg gagtgaatac cacgacgatt tccggcagtt    5400
tctacacata tattcgcaag atgtggcgtg ttacggtgaa aacctggcct atttccctaa    5460
agggtttatt gagaatatgt ttttcgtctc agccaatccc tgggtgagtt tcaccagttt    5520
tgatttaaac gtggccaata tggacaactt cttcgccccc gttttcacca tgggcaaata    5580
ttatacgcaa ggcgacaagg tgctgatgcc gctggcgatt caggttcatc atgccgtctg    5640
tgatggcttc catgtcggca gaatgcttaa tgaattacaa cagtactgcg atgagtggca    5700
gggcggggcg taatttttt aaggcagtta ttggtgccct taaacgcctg gtgctacgcc    5760
tgaataagtg ataataagcg gatgaatggc agaaattcgc atgaccaaaa tcccttaacg    5820
tgagttttcg ttccactgag cgtcagaccc cgtagaaaag atcaaggat cttcttgaga    5880
tccttttttt ctgcgcgtaa tctgctgctt gcaaacaaaa aaaccaccgc taccagcggt    5940
ggtttgtttg ccggatcaag agctaccaac tcttttccg aagtaactg gcttcagcag    6000
agcgcagata ccaaatactg tccttctagt gtagccgtag ttaggccacc acttcaagaa    6060
ctctgtagca ccgcctacat acctcgctct gctaatcctg ttaccagtgg ctgctgccag    6120
tggcgataag tcgtgtctta ccgggttgga ctcaagacga tagttaccgg ataaggcgca    6180
gcggtcgggc tgaacggggg gttcgtgcac acagcccagc ttggagcgaa cgacctacac    6240
cgaactgaga tacctacagc gtgagctatg agaaagcgcc acgcttcccg aagggagaaa    6300
ggcggacagg tatccggtaa gcggcagggt cggaacagga gagcgcacga gggagcttcc    6360
agggggaaac gcctggtatc tttatagtcc tgtcgggttt cgccacctct gacttgagcg    6420
tcgatttttg tgatgctcgt cagggggggcg gagcctatgg aaaaacgcca gcaacgcggc    6480
```

```
cttttttacgg ttcctggcct tttgctggcc ttttgctcac atgttctttc ctgcgttatc    6540
ccctgattct gtggataacc gtattaccgc ctttgagtga gctgataccg ctcgccgcag    6600
ccgaacgacc gagcgcagcg agtcagtgag cgaggaagcg gaagagcgcc tgatgcggta    6660
ttttctcctt acgcatctgt gcggtatttc acaccgcata tggtgcactc tcagtacaat    6720
ctgctctgat gccgcatagt taagccagta tacactccgc tatcgctacg tgactgggtc    6780
atggctgcgc cccgacaccc gccaacaccc gctgacgcgc cctgacgggc ttgtctgctc    6840
ccggcatccg cttacagaca agctgtgacc gtctccggga gctgcatgtg tcagaggttt    6900
tcaccgtcat caccgaaacg cgcgaggcag cagatcaatt cgcgcgcgaa ggcgaagcgg    6960
catgcattta cgttgacacc atcgaatggt gcaaaacctt tcgcggtatg gcatgatagc    7020
gcccggaaga gagtcaattc agggtggtga atgtgaaacc agtaacgtta tacgatgtcg    7080
cagagtatgc cggtgtctct tatcagaccg tttcccgcgt ggtgaaccag gccagccacg    7140
tttctgcgaa aacgcgggaa aaagtggaag cggcgatggc ggagctgaat tacattccca    7200
accgcgtggc acaacaactg gcgggcaaac agtcgttgct gattggcgtt gccacctcca    7260
gtctggccct gcacgcgccg tcgcaaattg tcgcggcgat taaatctcgc gccgatcaac    7320
tgggtgccag cgtggtggtg tcgatggtag aacgaagcgg cgtcgaagcc tgtaaagcgg    7380
cggtgcacaa tcttctcgcg caacgcgtca gtgggctgat cattaactat ccgctggatg    7440
accaggatgc cattgctgtg gaagctgcct gcactaatgt tccggcgtta tttcttgatg    7500
tctctgacca gacacccatc aacagtatta ttttctccca tgaagacggt acgcgactgg    7560
gcgtggagca tctggtcgca ttgggtcacc agcaaatcgc gctgttagcg ggcccattaa    7620
gttctgtctc ggcgcgtctg cgtctggctg gctggcataa atatctcact cgcaatcaaa    7680
ttcagccgat agcggaacgg gaaggcgact ggagtgccat gtccggtttt caacaaacca    7740
tgcaaatgct gaatgagggc atcgttccca ctgcgatgct ggttgccaac gatcagatgg    7800
cgctgggcgc aatgcgcgcc attaccgagt ccgggctgcg cgttggtgcg gatatctcgg    7860
tagtgggata cgacgatacc gaagacagct catgttatat cccgccgtta accaccatca    7920
aacaggattt tcgcctgctg gggcaaacca gcgtggaccg cttgctgcaa ctctctcagg    7980
gccaggcggt gaagggcaat cagctgttgc ccgtctcact ggtgaaaaga aaaaccaccc    8040
tggcgcccaa tacgcaaacc gcctctcccc gcgcgttggc cgattcatta atgcagctgg    8100
cacgacaggt ttcccgactg gaaagcgggc agtgagcgca acgcaattaa tgtaagttag    8160
cgcgaattga tctg                                                      8174
```

<210> SEQ ID NO 50
<211> LENGTH: 46
<212> TYPE: DNA
<213> ORGANISM: Artificial Sequence
<220> FEATURE:
<223> OTHER INFORMATION: primer_MW_15_50_fw

<400> SEQUENCE: 50
attcgagctc ggtacccggg atcctagtct tgtccaccca gaacag        46

<210> SEQ ID NO 51
<211> LENGTH: 45
<212> TYPE: DNA
<213> ORGANISM: Artificial Sequence
<220> FEATURE:
<223> OTHER INFORMATION: primer_MW_15_51_rv

<400> SEQUENCE: 51
aacagccaag cttgcatgcc tgcagttggt ttatccggag ggttg    45

<210> SEQ ID NO 52
<211> LENGTH: 6956
<212> TYPE: DNA
<213> ORGANISM: Artificial Sequence
<220> FEATURE:
<223> OTHER INFORMATION: pECXC99E

<400> SEQUENCE: 52
gtttgacagc ttatcatcga ctgcacggtg caccaatgct tctggcgtca ggcagccatc    60
ggaagctgtg gtatggctgt gcaggtcgta atcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagaccatgg aattcgagct cggtacccgg ggatcctcta    300
gagtcgacct gcaggcatgc aagcttggct gttttggcgg atgagagaag atttcagcc    360
tgatacagat taaatcagaa cgcagaagcg gtctgataaa acagaatttg cctggcggca    420
gtagcgcggt ggtcccacct gaccccatgc cgaactcaga agtgaaacgc cgtagcgccg    480
atggtagtgt ggggtctccc catgcgagag tagggaactg ccaggcatca ataaaacga    540
aaggctcagt cgaaagactg ggcctttcgt tttatctgtt gtttgtcggt gaacgctctc    600
ctgagtagga caaatccgcc gggagcggat ttgaacgttg cgaagcaacg gcccggaggg    660
tggcgggcag gacgcccgcc ataaactgcc aggcatcaaa ttaagcagaa ggccatcctg    720
acggatggcc ttttttgcgt tctacaaact cttttttgttt attttttctaa atacattcaa    780
atatgtatcc gctcatgaat taattccgct agatccccat caatcctgcc tatttgccac    840
gtttaacaag gtagttaagc gttcatttac gaagaaaaca cgataagctg cacaaatacc    900
tgaaaaagtt gaacgccccg tgagcgggaa ctcacagggc gtcggctaac ccccagtcat    960
cagctgggag aaagcactca agacatgact ctagccgatc cgcaggacac agtcacagct    1020
agcgcgtgga aattgtccgc cgatctgttc gacacccacc ccgaagctat gcgctgcggc    1080
tcacgcggct ggacggcaga agatcgccgc gaactgctcg ctcacctggg acgcgaaagc    1140
ttccagggca gcaagacaag agatttcgcg agcgcctgga ttaaaaaccc ggataccggc    1200
gaaacccaac caaagctcta ccgggctggc tcaaaagcgc tgacgcggtg ccagtacgtt    1260
gcgctgacgc acgcgcaaca tgccgcggtg atcgtgcttg acatcgatgt gcccagccac    1320
caggccggcg ggaagattga gcacgtaaac ccgcaggtct acgcgatttt agagaaatgg    1380
gcacgcctag aaaaagcgcc ggcttggatc ggcgtgaatc cgctgagcgg gaaatgccag    1440
ctcatctggc tcattgaccc ggtgtatgcc gcagcaggta aaaccagccc aaatatgcgc    1500
ctgctggctg caacgacgga agaaatgact cgtgtttttcg gcgctgacca ggcttttttcg    1560
cataggctga gccggtggcc gctgcacgtc tcagacgatc gcacagccta taatgcac    1620
tgccagcatg atcgtgtgga tcggctggcc gacctaatgg agattgctcg aacgatgacc    1680
ggatcacaga agccgaaaaa gtacattgag caggacttt ccagcggacg cgcccgcatt    1740
gaagcggcac aacgcgccac cgcagaagcc aaggcgctag cgattttgga cgcgagcctg    1800
ccgagcgccc tggacgcgtc cggcgacctg atcgacggcg tgcgagtgct ctggacaaat    1860
ccagagcgag cgcgcgacga gaccgcgttt cgccacgcgt tgaccgtggg ataccagctc    1920
aaagctgctg gtgagcgcct aaaagatgcc aagatcatcg acgcgtatga agtggcgtac    1980

```
aacgttgccc aggcggtcgg tgcagacggc cgggagccgg atcttcccgc catgcgtgat   2040
cgcctgacga tggcgcgtcg tgtgcgcggc tacgtggcta aaggccagcc agtcgtccct   2100
gctcgtcggg tggaaacgca gagcagccga gggcggaaag ctctagcgac gatggggcga   2160
cggggcgcag ctacatcgaa tgcacgcaga tgggctgacc cagaaagtaa gtatgcgcag   2220
gagacgcgac agcgattagc ggaagcaaac aaacgccgag aaatgacagg cgagttgctc   2280
gaacttcgcg tcaaaactgc gatcctggat gcccgttctc aatcggttgc tgatccctcg   2340
actcgtgagc ttgcaggcga actaggtgtc agtgaaaggc gcatccaaca agtcagaaag   2400
gcacttggaa tggaagctaa acgcggccgt ccacgggctg aaaactaata acgaaacac    2460
cgtcagcaga aaacggttcc cccctttagg ggtcccgtcc ttgctctggc tctcacttgc   2520
cctcaccctc cgctatccac gggctgaaaa ctaataaacg aaacaccgtc agcagaaaac   2580
ggttcccccc ctttagggtg tctcgctcct agctctgatc cctccccggt tcctcccgg    2640
cctgattttt aaggggggct cacgctgtcg gcagagaacg gttccccgcc ttctgctctg   2700
gctcttcctc gactccctcc ccctcaaaaa tctcctcgag atcctggaga cctttttgga   2760
gctagcgcgt tgctgcttcg caccaacttg ctcatgatga ttttcatttt tgcttgtgtg   2820
cttttttggg ttgaaccctc caaagagggg aaaccagggg cacacctcat gcactaaagt   2880
gccgcttcgc tggtcagggt gaaatcacct ggaaaaaaag tgcggtaacc gctgcgcttg   2940
gcgtttttc tgggcaagaa gtctcgcagg ttttcgcagg agtgccggaa gaaattatca    3000
gaattggggc tagaattttt aacgaacgtt cgttataatg gtgtcatgac cttcacgacg   3060
aagtaccaaa actggcctga agcatcagcg gtggatctct ccgatgtcgc gctggagtcc   3120
gacgcactcg atgccgccgt cgatttaaaa acggtgatcg gatttttccg cgccctcgat   3180
acgacagacg cgccagcatc acgcgactgg gcaagtgccg cgagcgacct agaaacgctt   3240
gtggccgacc ttgaagagct ggccgacgag ctgcgtgctc ggcagcgcca ggaggacgcg   3300
cagtagtgga ggatcgcatc agctgcgcct actgcggtgg cctgatccca ccccggcctg   3360
acccacgagg acggcgcgca aaatactgct cagacgcgtg tcgtgccgca gccagccgcg   3420
agcgcgccaa caagcgccac gcccaggagg tcgaagccgc acgtcatcta gcgctgatgt   3480
ccggcggtgc ttttgccgtt acgcaccacc ccgtcagtag ctgaacagga gggacagctg   3540
atagaaacag aagccactgg agcacctcaa aaacaccatc atacactaaa tcagtaagtt   3600
ggcagcatca cccgacgcac tttgcgccga ataaatacct gtgacggaag atcacttcgc   3660
agaataaata aatcctggtg tccctgttga taccggaag ccctgggcca acttttggcg    3720
aaaatgagac gttgatcggc acgtaagagg ttccaacttt caccataatg aaataagatc   3780
actaccgggc gtattttttg agttatcgag attttcagga gctaaggaag ctaaaatgga   3840
gaaaaaaatc actggatata ccaccgttga tatatcccaa tggcatcgta aagaacattt   3900
tgaggcattt cagtcagttg ctcaatgtac ctataaccag accgttcagc tggatattac   3960
ggccttttta aagaccgtaa agaaaaataa gcacaagttt tatccggcct ttattcacat   4020
tcttgcccgc ctgatgaatg ctcatccgga attccgtatg gcaatgaaag acggtgagct   4080
ggtgatatgg gatagtgttc acccttgtta caccgttttc catgagcaaa ctgaaacgtt   4140
ttcatcgctc tggagtgaat accacgacga tttccggcag tttctacaca tatattcgca   4200
agatgtggcg tgttacggtg aaaacctggc ctatttccct aaagggttta ttgagaatat   4260
gttttttcgtc tcagccaatc cctgggtgag tttcaccagt tttgatttaa acgtggccaa   4320
tatggacaac ttcttcgccc ccgttttcac catgggcaaa tattatacgc aaggcgacaa   4380
```

```
ggtgctgatg ccgctggcga ttcaggttca tcatgccgtc tgtgatggct tccatgtcgg   4440
cagaatgctt aatgaattac aacagtactg cgatgagtgg cagggcgggg cgtaattttt   4500
ttaaggcagt tattggtgcc cttaaacgcc tggtgctacg cctgaataag tgataataag   4560
cggatgaatg gcagaaattc gcatgaccaa aatcccttaa cgtgagtttt cgttccactg   4620
agcgtcagac cccgtagaaa agatcaaagg atcttcttga tccttttt ttctgcgcgt   4680 aatctgctgc ttgcaaacaa aaaaaccacc gctaccagcg gtggtttgtt tgccggatca   4740
agagctacca actctttttc cgaaggtaac tggcttcagc agagcgcaga taccaaatac   4800
tgtccttcta gtgtagccgt agttaggcca ccacttcaag aactctgtag caccgcctac   4860
atacctcgct ctgctaatcc tgttaccagt ggctgctgcc agtggcgata agtcgtgtct   4920
taccgggttg gactcaagac gatagttacc ggataaggcg cagcggtcgg gctgaacggg   4980
gggttcgtgc acacagccca gcttggagcg aacgacctac accgaactga gatacctaca   5040
gcgtgagcta tgagaaagcg ccacgcttcc cgaagggaga aaggcggaca ggtatccggt   5100
aagcggcagg gtcggaacag gagagcgcac gagggagctt ccagggggaa acgcctggta   5160
tctttatagt cctgtcgggt ttcgccacct ctgacttgag cgtcgatttt tgtgatgctc   5220
gtcagggggg cggagcctat ggaaaaacgc cagcaacgcg gcctttttac ggttcctggc   5280
cttttgctgg ccttttgctc acatgttctt cctgcgtta ccctgatt ctgtggataa   5340 ccgtattacc gcctttgagt gagctgatac cgctcgccgc agccgaacga ccgagcgcag   5400
cgagtcagtg agcgaggaag cggaagagcg cctgatgcgg tattttctcc ttacgcatct   5460
gtgcggtatt tcacaccgca tatggtgcac tctcagtaca atctgctctg atgccgcata   5520
gttaagccag tatacactcc gctatcgcta cgtgactggg tcatggctgc gccccgacac   5580
ccgccaacac ccgctgacgc gccctgacgg gcttgtctgc tcccggcatc cgcttacaga   5640
caagctgtga ccgtctccgg gagctgcatg tgtcagaggt tttcaccgtc atcaccgaaa   5700
cgcgcgaggc agcagatcaa ttcgcgcgcg aaggcgaagc ggcatgcatt tacgttgaca   5760
ccatcgaatg gtgcaaaacc tttcgcggta tggcatgata gcgcccggaa gagagtcaat   5820
tcagggtggt gaatgtgaaa ccagtaacgt tatacgatgt cgcagagtat gccggtgtct   5880
cttatcagac cgtttcccgc gtggtgaacc aggccagcca cgtttctgcg aaaacgcggg   5940
aaaagtggaa gcggcgatg gcggagctga attacattcc caaccgcgtg gcacaacaac   6000
tggcgggcaa acagtcgttg ctgattggcg ttgccacctc cagtctggcc ctgcacgcgc   6060
cgtcgcaaat tgtcgcggcg attaaatctc gcgccgatca actgggtgcc agcgtggtgg   6120
tgtcgatggt agaacgaagc ggcgtcgaag cctgtaaagc ggcggtgcac aatcttctcg   6180
cgcaacgcgt cagtgggctg atcattaact atccgctgga tgaccaggat gccattgctg   6240
tggaagctgc ctgcactaat gttccggcgt tatttcttga tgtctctgac cagacaccca   6300
tcaacagtat tattttctcc catgaagacg gtacgcgact gggcgtggag catctggtcg   6360
cattgggtca ccagcaaatc gcgctgttag cgggcccatt aagttctgtc tcggcgcgtc   6420
tgcgtctggc tggctggcat aaatatctca ctcgcaatca aattcagccg atagcggaac   6480
gggaaggcga ctggagtgcc atgtccggtt ttcaacaaac catgcaaatg ctgaatgagg   6540
gcatcgttcc cactgcgatg ctggttgcca acgatcagat ggcgctgggc gcaatgcgcg   6600
ccattaccga gtccgggctg cgcgttgtg cggatatctc ggtagtggga tacgacgata   6660
ccgaagacag ctcatgttat atcccgccgt caaccaccat caaacaggat tttcgcctgc   6720
```

```
tggggcaaac cagcgtggac cgcttgctgc aactctctca gggccaggcg gtgaagggca    6780
atcagctgtt gcccgtctca ctggtgaaaa gaaaaaccac cctggcgccc aatacgcaaa    6840
ccgcctctcc ccgcgcgttg gccgattcat taatgcagct ggcacgacag gtttcccgac    6900
tggaaagcgg gcagtgagcg caacgcaatt aatgtgagtt agcgcgaatt gatctg        6956
```